(12) United States Patent
Nishino et al.

(10) Patent No.: US 8,867,702 B2
(45) Date of Patent: *Oct. 21, 2014

(54) RADIOGRAPHIC IMAGE CAPTURING SYSTEM AND RADIOGRAPHIC IMAGE CAPTURING METHOD

(75) Inventors: Naoyuki Nishino, Kanagawa-ken (JP); Yasunori Ohta, Kanagawa-ken (JP)

(73) Assignee: Fujifilm Corporation, Tokyo (JP)

( * ) Notice: Subject to any disclaimer, the term of this patent is extended or adjusted under 35 U.S.C. 154(b) by 397 days.

This patent is subject to a terminal disclaimer.

(21) Appl. No.: 13/137,532

(22) Filed: Aug. 24, 2011

(65) Prior Publication Data

US 2012/0051513 A1    Mar. 1, 2012

(30) Foreign Application Priority Data

Aug. 24, 2010 (JP) ................................. 2010-187302
Aug. 18, 2011 (JP) ................................. 2011-179093

(51) Int. Cl.
G01N 23/04 (2006.01)
A61B 6/00 (2006.01)

(52) U.S. Cl.
CPC ............. *A61B 6/4007* (2013.01); *A61B 6/4411* (2013.01)
USPC .............................................. 378/63; 378/92

(58) Field of Classification Search
USPC ................. 378/62, 63, 92, 193, 197
See application file for complete search history.

(56) References Cited

U.S. PATENT DOCUMENTS

| 7,050,532 B2 | 5/2006 | Gohno |
| 7,768,002 B2 | 8/2010 | Kitamura et al. |
| 7,847,258 B2 | 12/2010 | Yaegashi et al. |
| 7,978,816 B2 * | 7/2011 | Matsuura et al. ............... 378/62 |
| 8,345,820 B2 * | 1/2013 | Yoshida et al. ................. 378/62 |
| 2009/0224162 A1 | 9/2009 | Inuiya et al. |

FOREIGN PATENT DOCUMENTS

| CN | 1589745 | 3/2005 |
| JP | 2000-105297 | 4/2000 |
| JP | 2003-310599 | 11/2003 |
| JP | 2007-061386 | 3/2007 |
| JP | 2007-103016 | 4/2007 |
| JP | 2009-032854 | 2/2009 |
| JP | 2009-153589 | 7/2009 |
| JP | 2009-212377 | 9/2009 |
| JP | 2009-212389 | 9/2009 |

OTHER PUBLICATIONS

National Institute of Advanced Industrial Science & Technology, "Development of Portable X-ray Sources Using Carbon Nanostructures" [online], Mar. 19, 2009, pp. 1-4.
First Office Action issued by SIPO on Apr. 25, 2014 in connection with corresponding Chinese Patent No. 201110255485.5.
Rejection of the Application issued on Aug. 19, 2014 by Japanese Patent Office in connection with corresponding Japanese Patent Application No. 2011-179093.

* cited by examiner

*Primary Examiner* — Jurie Yun
(74) *Attorney, Agent, or Firm* — Jean C. Edwards, Esq.; Edwards Neils PLLC

(57) ABSTRACT

An optical image of a subject is acquired with a camera while the subject is disposed between a radiation output device housing at least two radiation sources and a radiation detecting device. Doses of radiation to be emitted from the at least two radiation sources are weighted based on the optical image, and weighted doses of radiation are applied from the at least two radiation sources to the subject. A radiographic image of the subject is acquired by detecting radiation that has passed through the subject with the radiation detecting device.

16 Claims, 29 Drawing Sheets

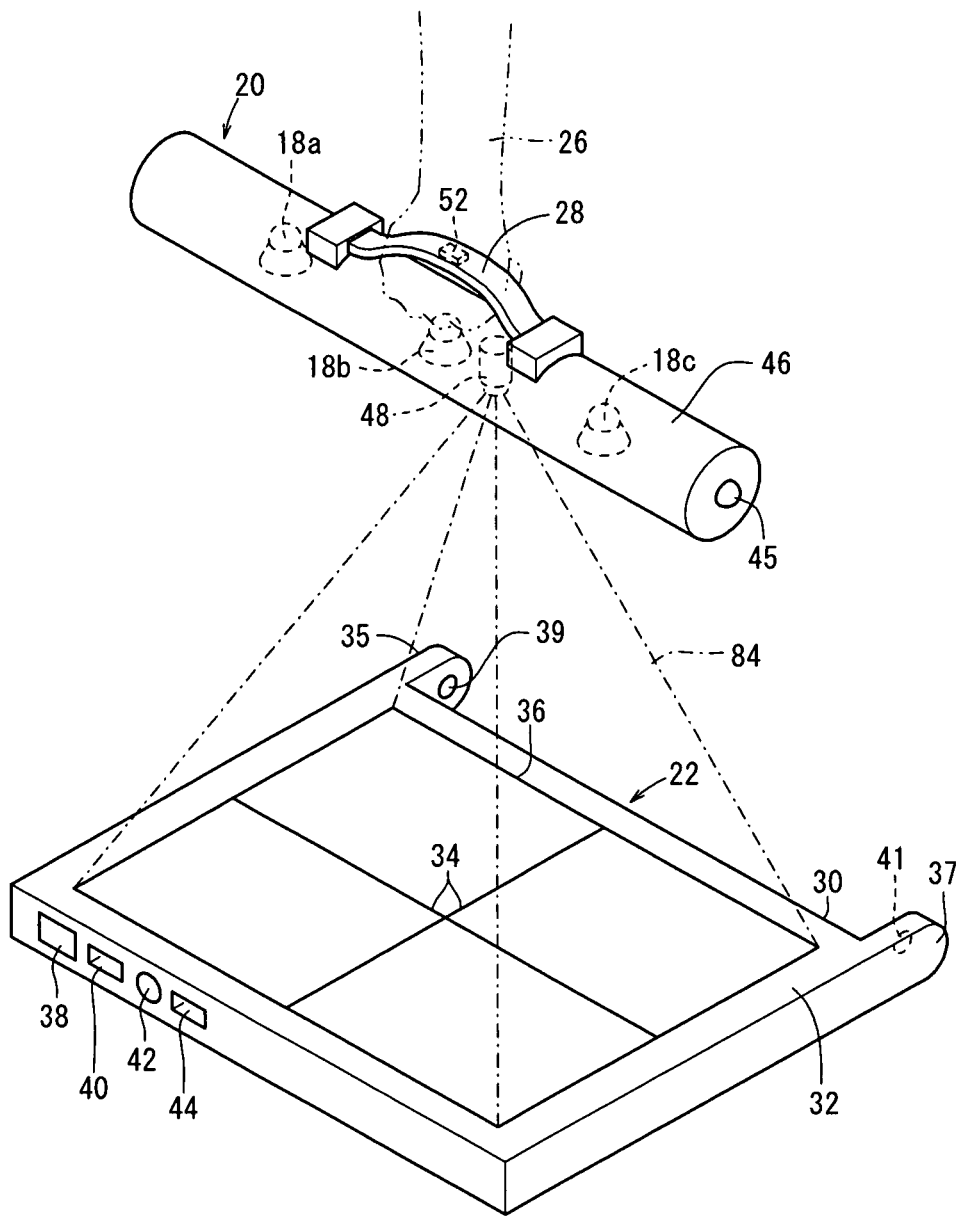

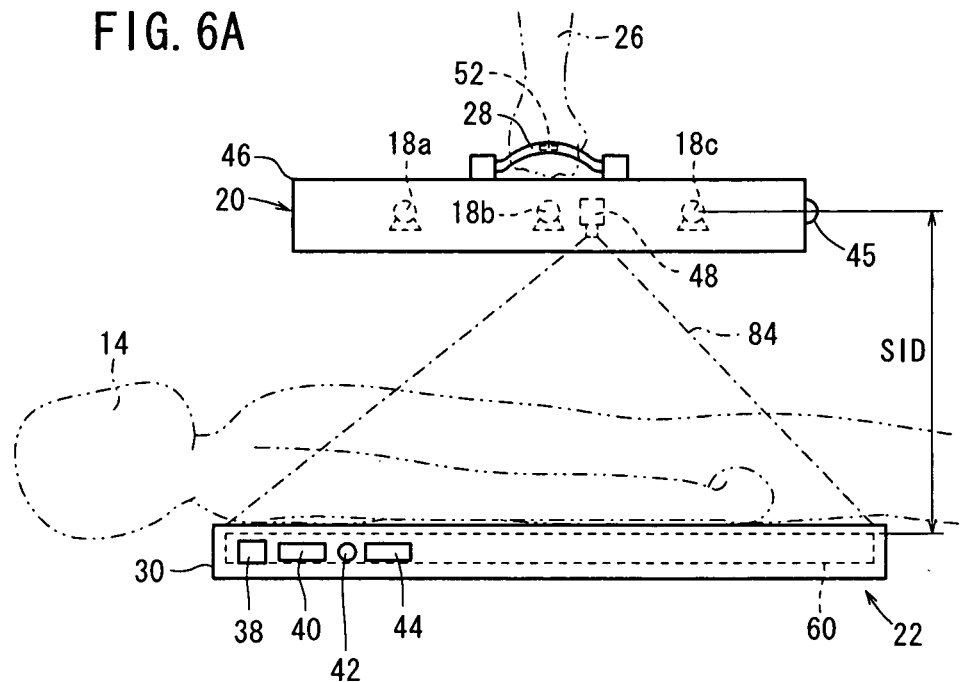
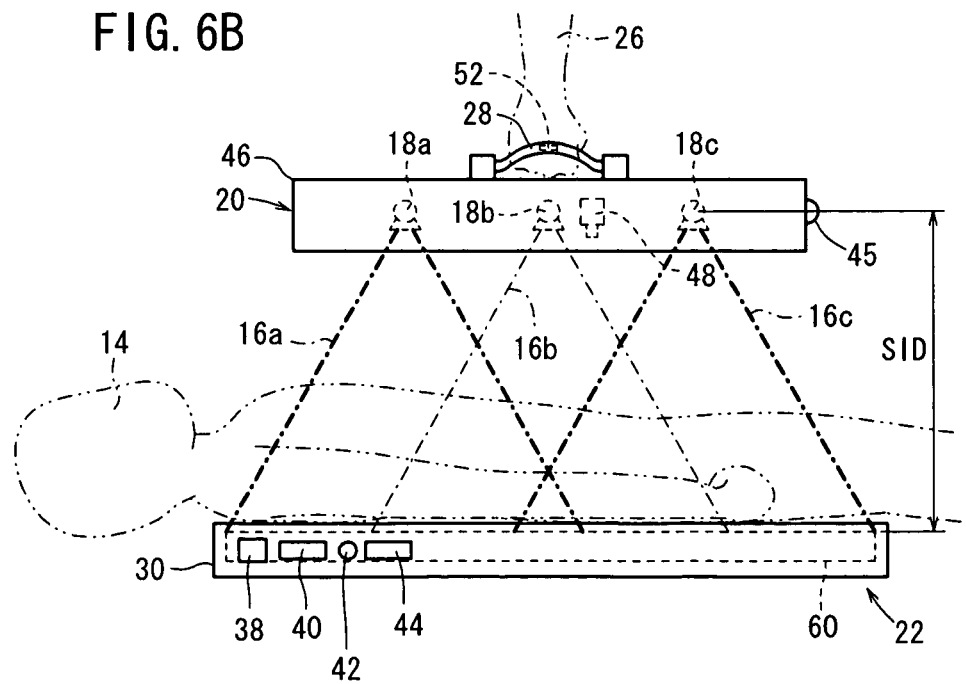

FIG. 12

| REGION TO BE IMAGED (TECHNIQUE) | THICKNESS [mm] | RADIATION DOSE [mR] | | |
|---|---|---|---|---|
| CHEST (CAPTURING IMAGE OF FRONTAL CHEST) | ▽▽ ...... | ◇◇ ...... | ...... | ... |
| HAND (CAPTURING IMAGE OF BACK OF HAND) | ▽▽▽ ...... | ◇◇◇ ...... | ...... | ... |
| ... | | | | |

FIG. 13

| REGION TO BE IMAGED (TECHNIQUE) | NUMBER OF RADIATION SOURCES | WEIGHTING OF RADIATION DOSE ||||
| --- | --- | --- | --- | --- | --- |
| | | A | B | C | ⋮ |
| CHEST | 2 | ○○ | △△ | — | ⋮ |
| (CAPTURING IMAGE OF FRONTAL CHEST) | 3 | □□ | ×× | □□ | ⋮ |
| ⋮ | ⋮ | ⋮ | ⋮ | ⋮ | ⋮ |
| HAND | 2 | ○○ | △△ | — | ⋮ |
| (CAPTURING IMAGE OF BACK OF HAND) | 3 | □□ | ×× | □□ | ⋮ |
| ⋮ | ⋮ | ⋯ | ⋯ | ⋯ | ⋯ |
| ⋮ | ⋮ | ⋯ | ⋯ | ⋯ | ⋯ |

RADIOGRAPHIC IMAGE CAPTURING SYSTEM AND RADIOGRAPHIC IMAGE CAPTURING METHOD

CROSS-REFERENCE TO RELATED APPLICATION

This application is based upon and claims the benefit of priority from Japanese Patent Applications No. 2010-187302 filed on Aug. 24, 2010 and No. 2011-179093 filed on Aug. 18, 2011, of which the contents are incorporated herein by reference.

BACKGROUND OF THE INVENTION

1. Field of the Invention:

The present invention relates to a radiographic image capturing system and a radiographic image capturing method for applying radiation from a plurality of radiation sources housed in a radiation output device to a subject, detecting radiation that has passed through the subject with a radiation detecting device, and converting the detected radiation into radiographic images.

2. Description of the Related Art:

In the medical field, there have widely been used radiographic image capturing systems, which apply radiation from a radiation source to a subject and detect the radiation that has passed through the subject with a radiation detecting device in order to acquire a radiographic image of the subject. Radiographic image capturing systems that are installed in hospitals (medical organizations), for example, usually employ a thermionic emission radiation source, which is relatively large and heavy.

If such a radiographic image capturing system is directly used to capture radiographic images within hospitals while making rounds, or outside of hospitals, e.g., in medical checkup cars, at sites suffering from natural disasters, or at sites receiving home care services, then a large and heavy radiation source needs to be carried to such sites for capturing radiographic images. The process of carrying the radiation source to the site and setting up the radiation source at the site is quite burdensome for the doctor or radiological technician in charge. To solve this problem, Japanese Laid-Open Patent Publication No. 2007-103016 discloses a field-emission radiation source, which is smaller and lighter than a thermionic emission radiation source.

SUMMARY OF THE INVENTION

If a field-emission radiation source is operated at a site, it is highly likely that difficulties will be experienced in preparing an appropriate external power supply. Therefore, the field-emission radiation source should preferably be of a battery-powered design. However, a battery-powered field-emission radiation source, although it is small and lightweight, emits a small dose of radiation. It is customary for the doctor or radiological technician to keep the field-emission radiation source as closely to the subject as possible while capturing a radiographic image of the subject at a site, in order to reduce the source-to-image distance (SID) between the field-emission radiation source and the radiation detecting device. As a result, radiation emitted from the field-emission radiation source has a small irradiation range. Because of the small irradiation range, and also due to the small dose (exposure dose) of radiation applied to the subject, the field-emission radiation source may fail to capture a radiation image based on an exposure dose that is sufficiently large for a doctor to read radiation images correctly.

One solution is to install a plurality of field-emission radiation sources and to emit radiation from such field-emission radiation sources toward a subject in order to cover a desired irradiation range (a region to be imaged of the subject). According to another solution, while a single field-emission radiation source is being moved over the subject, radiation is emitted toward the subject from the field-emission radiation source, which has been moved to different positions in order to cover a desired irradiation range.

As long as a subject is irradiated with an optimum dose (exposure dose) of radiation depending on the subject, a radiographic image of the subject can be captured based on an exposure dose that is large enough for a doctor to read the resultant radiation image correctly, and the subject remains free of undue radiation exposure.

Stated simply, even if a field-emission radiation source applies radiation to a subject in order to cover a desired irradiation range, the subject may not necessarily be irradiated with an optimum dose of radiation.

An object of the present invention is to provide a radiographic image capturing system and a radiographic image capturing method, which are capable of easily increasing an irradiation range of radiation, and of applying an optimum dose of radiation to a subject at the time that a radiographic image of the subject is captured using a field-emission radiation source at a short SID.

To accomplish the above object, in accordance with the present invention, there is provided a radiographic image capturing system comprising a radiation output device housing therein at least two radiation sources for emitting radiation, a radiation detecting device for detecting the radiation that has passed through a subject and converting the detected radiation into a radiographic image, a camera for acquiring an optical image of the subject, and a control device for controlling the radiation output device and the radiation detecting device, wherein the control device weights doses of radiation emitted from the at least two radiation sources based on the optical image, and controls the radiation output device to apply the weighted doses of radiation from the at least two radiation sources to the subject.

According to the present invention, there also is provided a radiographic image capturing method comprising capturing an optical image of a subject with a camera while the subject is disposed between a radiation output device housing therein at least two radiation sources and a radiation detecting device, weighting doses of radiation emitted from the at least two radiation sources based on the optical image, and applying the weighted doses of radiation from the at least two radiation sources to the subject, and acquiring a radiographic image of the subject by detecting the radiation that has passed through the subject with the radiation detecting device.

According to the present invention, an optical image of the subject is captured with the camera, which is disposed between the radiation output device housing therein at least two radiation sources and the radiation detecting device, and doses of radiation are emitted from the at least two radiation sources based on the optical image.

As described above, rather than simply establishing an irradiation range of radiation so as to cover a region to be imaged of the subject, doses of radiation, which are emitted from the radiation sources for capturing a radiographic image of the subject (main exposure mode), are weighted based on the optical image captured with the camera prior to the main exposure mode. Since the region to be imaged of the subject is included within the optical image, the doses of radiation are weighted according to the region to be imaged of the subject.

According to the present invention, therefore, even if a radiographic image of the subject is captured (main exposure mode) at a short SID using field-emission radiation sources, the irradiation range of radiation can easily be increased, and the subject can be irradiated with optimal doses of radiation. Since the subject is irradiated with optimal doses of radiation depending on the subject, it is possible to produce an appropriate radiographic image (main exposure image) for the doctor to read, and to prevent the subject from suffering from undue radiation exposure.

If the radiation output device and the radiation detecting device face toward each other, then the radiation output device may house therein at least two radiation sources arranged in a linear array, or at least three radiation sources arranged in a two-dimensional matrix over an irradiated surface of the radiation detecting device, which is irradiated with radiation. This arrangement enables efficient capturing of radiographic images of any regions to be imaged of the subject.

The above and other objects, features, and advantages of the present invention will become more apparent from the following description when taken in conjunction with the accompanying drawings in which a preferred embodiment of the present invention is shown by way of illustrative example.

BRIEF DESCRIPTION OF THE DRAWINGS

FIG. 3 is a perspective view of the radiation output device and the radiation detecting device, which are in an operational layout;

FIG. 6A is a side elevational view showing the manner in which a region to be imaged of a subject is imaged by a web camera;

FIG. 6B is a side elevational view showing the manner in which the region to be imaged of the subject is irradiated;

FIG. 12 is a diagram showing, by way of example, a table that is stored in the database shown in FIG. 9;

FIG. 13 is a diagram showing, by way of example, a table that is stored in the database shown in FIG. 9;

DESCRIPTION OF THE PREFERRED EMBODIMENTS

A radiographic image capturing system according to a preferred embodiment of the present invention, in relation to a radiographic image capturing method, will be described in detail below with reference to FIGS. 1 through 29B.

Figure 1:
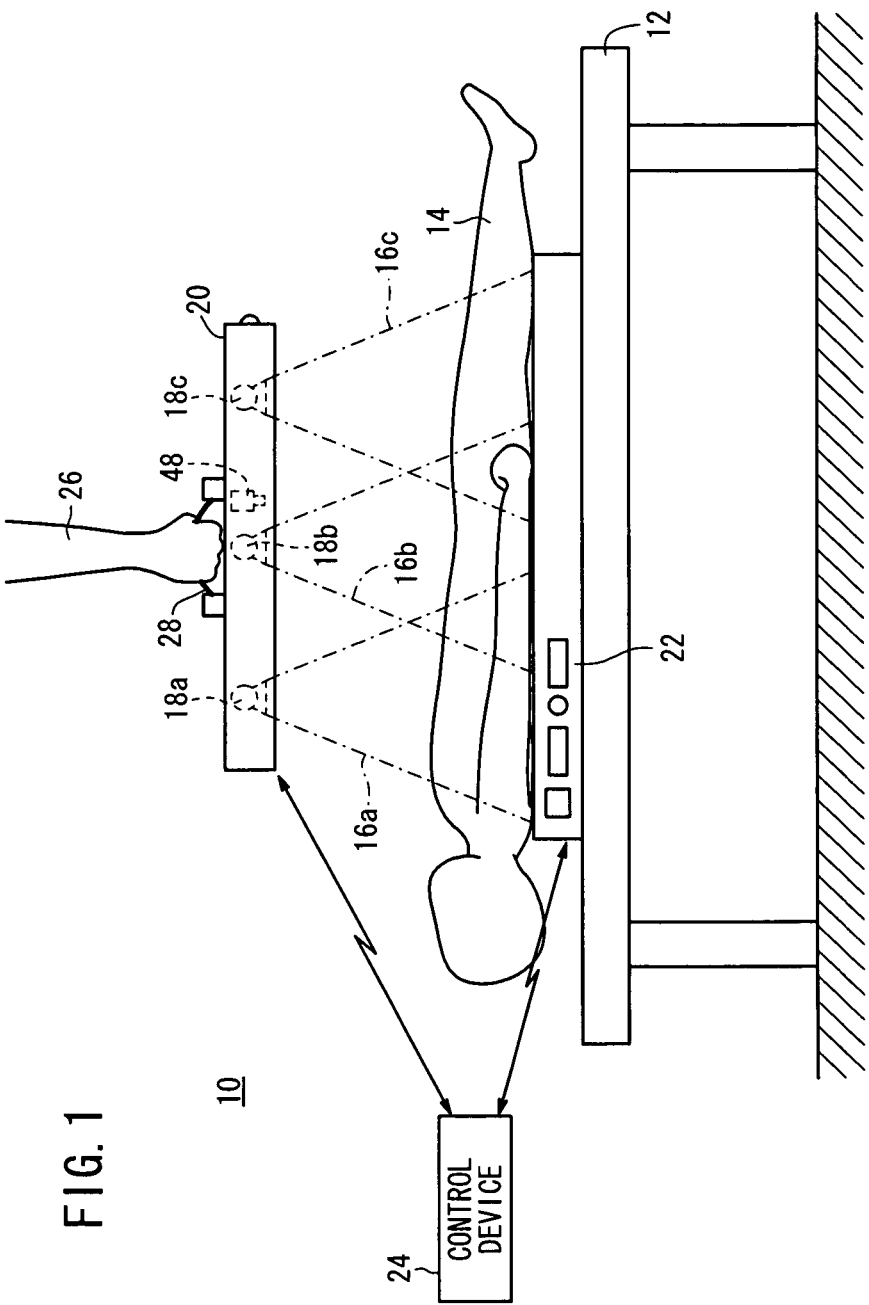
FIG. 1 is an elevational view of a radiographic image capturing system according to an embodiment of the present invention.

As shown in FIG. 1, a radiographic image capturing system 10 according to an embodiment of the present invention includes a radiation output device 20 housing therein a plurality (three in the present embodiment) of radiation sources 18a through 18c, which are capable of applying radiation 16a through 16c respectively to a subject 14 lying on an image capturing table 12 such as a bed or the like, a radiation detecting device 22 for detecting radiation that has passed through the subject 14 and converting the detected radiation into radiation images, and a control device 24 for controlling the radiation output device 20 and the radiation detecting device 22.

The radiation output device 20 also houses therein a web camera 48 for imaging a predetermined imaging range 84 (see FIG. 3) in order to acquire a camera image (optical image) thereof. In other words, the radiation output device 20 and the web camera 48 are integrally combined with each other.

Integral combination of the radiation output device 20 and the web camera 48 is not limited to an arrangement in which the web camera 48 is housed in the radiation output device 20, but refers to any arrangement in which the web camera 48 is integrally joined (connected) to the radiation output device 20, at least when the radiographic image capturing system 10 is in use. For example, integral combination of the radiation output device 20 and the web camera 48 includes (1) an arrangement in which the web camera 48 and the radiation output device 20 are connected to each other by a cable provided by the radiographic image capturing system 10, (2) an arrangement in which the web camera 48 and the radiation output device 20 are connected to each other by a cable provided by a doctor 26 (see FIG. 3), and (3) an arrangement in which the radiation output device 20 and the web camera 48 are joined to each other when the radiographic image capturing system 10 is in use, and wherein the radiation output device 20 and the web camera 48 can be disconnected (separable) from each other when the radiographic image capturing system 10 is undergoing maintenance or is not in use.

To make the web camera 48 disconnectable from the radiation output device 20 when the radiographic image capturing system 10 is undergoing maintenance or is not in use, the web camera 48 may be joined to the radiation output device 20 by a joining means such as a clip or the like. The web camera 48 may be joined to the radiation output device 20 by the joining means only when the radiographic image capturing system 10 is in use. The joining means may incorporate a ball joint for enabling the orientation of the web camera 48, which is joined to the radiation output device 20, to be freely changed. If the web camera 48 is joined to the radiation output device 20 by the joining means, then it is necessary for the web camera 48 and the radiation output device 20 to be electrically connected to each other via a wired link, e.g., a USB cable, or a wireless link.

If the radiation output device 20 and the web camera 48 are connected to each other by a cable, then since the web camera 48 can independently be placed in a desired position within a range defined by the length of the cable, the web camera 48 can be positioned with greater freedom than if the web camera 48 were housed in the radiation output device 20. The control device 24, the radiation output device 20, and the web camera 48 may send signals to each other and receive signals from each other by way of a wireless LAN according to standards such as UWB (Ultra-Wide Band), IEEE802.11.a/g/n. or the like, wireless communications using millimeter waves, or by wired communications using cables.

The radiographic image capturing system 10 may be applied in order to capture radiographic images of the subject 14 (patient) in an image capturing chamber of a radiological department of a hospital (medical organization), to capture radiographic images of the subject 14 (patient) in a patient's bedroom in a hospital at the time that the doctor 26 makes rounds, or to capture radiographic images of the subject 14 outside of the hospital. Capturing of radiographic images of the subject 14 outside of the hospital refers to capturing of radiographic images of the subject 14 (examinee) at the time that a medical checkup is carried out using a medical checkup car, capturing of radiographic images of the subject 14 (injured) at a disaster site such as a natural disaster site, or capturing of radiographic images of the subject 14 (resident) at a home medical care site.

To realize such applications, each of the radiation sources 18*a* through 18*c* of the radiographic image capturing system 10 according to the present embodiment should preferably be a field-emission radiation source, as disclosed in Japanese Laid-Open Patent Publication No. 2007-103016. The radiation output device 20, which houses therein the radiation sources 18*a* through 18*c*, has a grip 28 to be gripped by the doctor or radiological technician in charge (hereinafter simply referred to as "doctor"), on a side thereof remote from the side on which radiation 16*a* through 16*c* is emitted from the radiation sources 18*a* through 18*c*. Therefore, the radiation output device 20 comprises a portable device.

The radiation detecting device 22 comprises a portable electronic cassette incorporating either a radiation detector of an indirect conversion type including a scintillator for temporarily converting radiation that has passed through the subject 14 into visible light, and a solid-state detector (hereinafter also referred to as "pixels"), which is made of a substance such as amorphous silicon (a-Si) or the like, for converting visible light into electric signals, or alternatively, the radiation detecting device 22 comprises a radiation detector of a direct conversion type including a solid-state detector, which is made of a substance such as amorphous selenium (a-Se) or the like, for converting radiation that has passed through the subject 14 into electric signals.

The control device 24 should preferably be a portable information terminal such as a laptop personal computer (PC), a tablet PC, or a personal digital assistant (PDA), for example. If the radiographic image capturing system 10 is used in an image capturing chamber of the radiological department of a hospital, then the control device 24 may comprise a stationary console, while the radiation output device 20 and the radiation detecting device 22 may be portable devices.

Figure 2A:
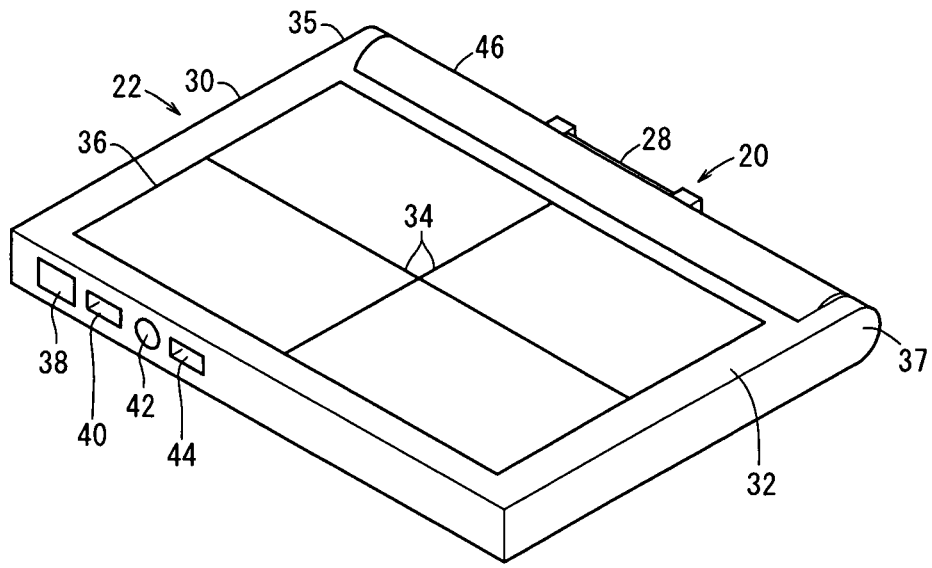
FIG. 2A is a perspective view of a radiation output device and a radiation detecting device shown in FIG. 1, which are integrally combined with each other.
Figure 2B:
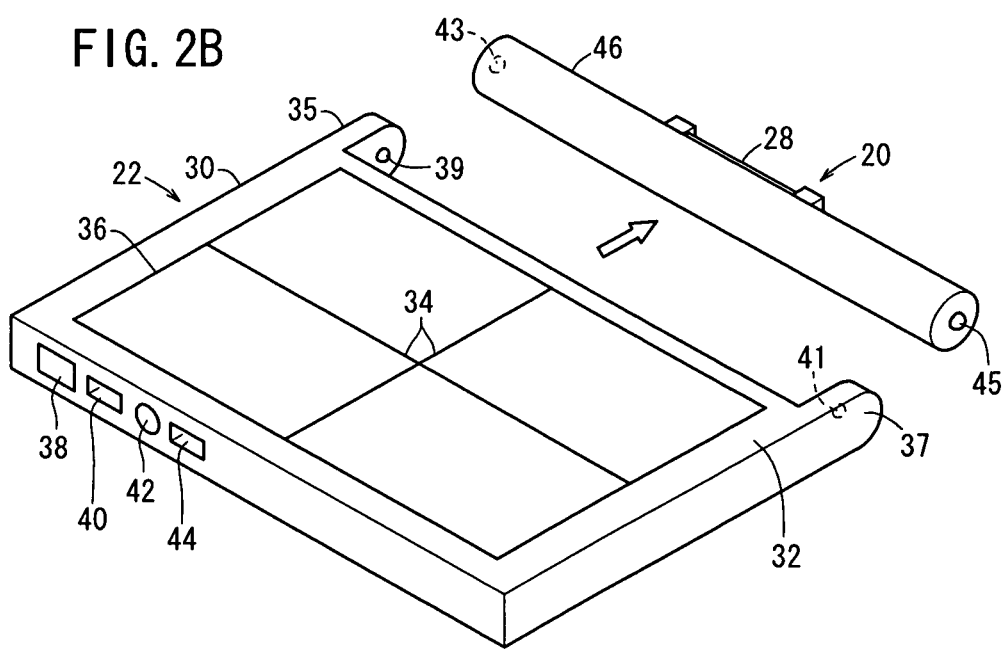
FIG. 2B is a perspective view of the radiation output device and the radiation detecting device, which are separated from each other.

As shown in FIGS. 2A through 3, the radiation detecting device 22 includes a rectangular housing 30 made of a material permeable to radiation 16*a* through 16*c* (see FIG. 1) and having a surface (upper surface) for positioning the subject 14 thereon, the surface serving as an irradiated surface 32, which is irradiated with radiation 16*a* through 16*c*. The irradiated surface 32 has guide lines 34 serving as a reference for an image capturing area and an image capturing position for the radiation 16*a* through 16*c*. The guide lines 34 provide an outer frame defining an imaging area 36, which can be irradiated with radiation 16*a* through 16*c*. One side of the housing 30 has a switch 38 for turning on and off the radiation detecting device 22, a card slot 40 for receiving a memory card (not shown) therein, an input terminal 42 for connection to an AC adapter, and a USB terminal 44 for connection to a USB cable (not shown).

The radiation detecting device 22 also includes a pair of holders 35, 37 projecting outwardly from a side of the housing 30 remote from the side having the switch 38, the card slot 40, the input terminal 42, and the USB terminal 44. The holder 35 has a convex connection terminal 39 facing the holder 37, and the holder 37 has a concave connection terminal 41 facing the holder 35 (see FIGS. 2B through 4B). The radiation output device 20 has a hollow cylindrical casing 46 including a concave connection terminal 43 on an end thereof for receiving therein the convex connection terminal 39 of the holder 35, and a convex connection terminal 45 on the other end thereof for being fitted into the concave connection terminal 41 of the holder 37 (see FIGS. 2B, 5A and 5B).

When the connection terminals 39, 43 and the connection terminals 41, 45 are held respectively in interfitting engagement with each other, the radiation output device 20 is held between the holders 35, 37, as shown in FIG. 2A, and the connection terminals 39, 43 and the connection terminals 41, 45 are electrically connected to each other. Once the radiation output device 20 and the radiation detecting device 22 are integrally combined with each other, the doctor 26 can grip the grip 28, for example, and carry the radiation output device 20 and the radiation detecting device 22. Further, while the radiation output device 20 and the radiation detecting device 22 are integrally combined with each other, the side of the radiation output device 20 where radiation 16a through 16c is emitted from the radiation sources 18a through 18c faces toward a side, which lies between the holders 35, 37 of the housing 30 of the radiation detecting device 22.

When the radiation output device 20 is released and separated from the holders 35, 37 and the connection terminals 39, 41 of the radiation detecting device 22, the radiation output device 20 and the radiation detecting device 22 are no longer integrally combined with each other, and the connection terminals 39, 43 and the connection terminals 41, 45 are electrically disconnected from each other, respectively.

Figure 4A:
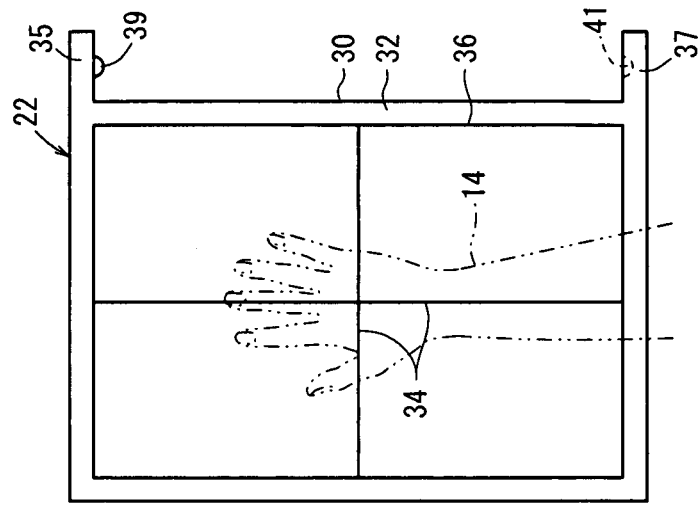
FIGS. 4A and 4B are plan views showing how regions to be imaged of a subject are positioned with respect to the radiation detecting device.
Figure 4B:
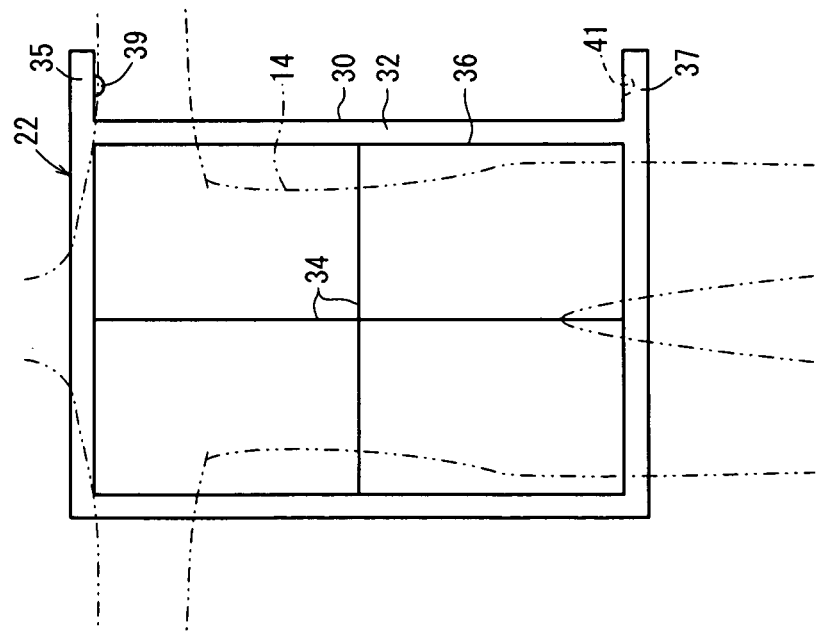

As shown in FIGS. 4A and 4B, for positioning the subject 14 on the radiation detecting device 22, a region to be imaged of the subject 14 is positioned such that a central position of the region to be imaged of the subject 14 and a central position (i.e., a point of intersection of the guide lines 34) of the imaging area 36 are kept in substantial alignment with each other, and the region to be imaged of the subject 14 falls within the imaging area 36. FIG. 4A shows the chest of the subject 14, which is positioned on the radiation detecting device 22 as a region to be imaged. FIG. 4B shows a right hand of the subject 14, which is positioned on the radiation detecting device 22 as a region to be imaged.

Figure 5A:
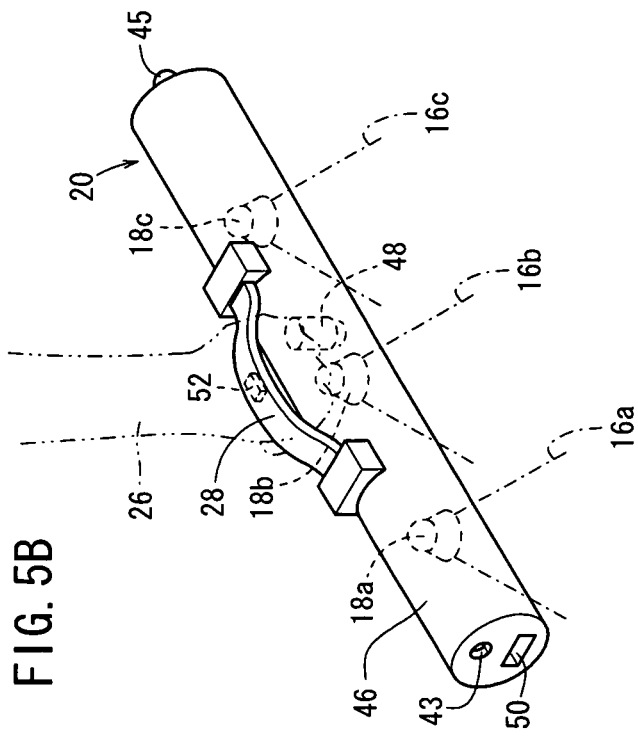
FIGS. 5A and 5B are perspective views of the radiation output device.
Figure 5B:
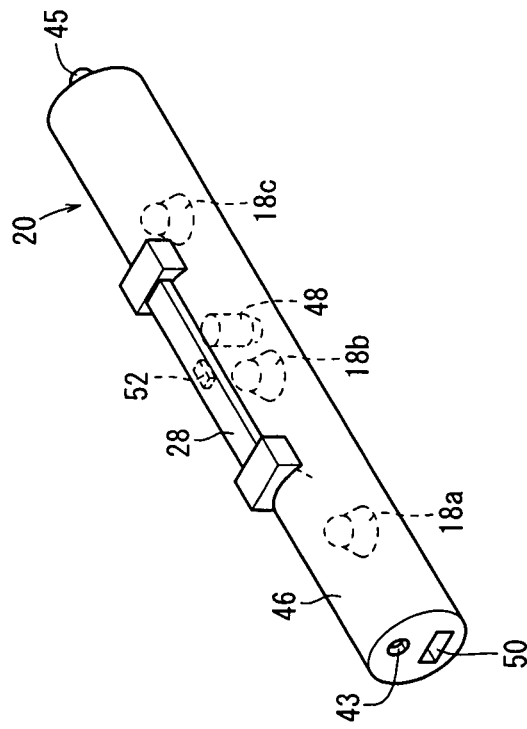

As shown in FIGS. 3, 5A and 5B, the radiation output device 20 includes the hollow cylindrical casing 46, which is made of a material permeable to radiation 16a through 16c. The three field-emission radiation sources 18a through 18c are arranged along one direction, i.e., arranged as a linear array, in the casing 46. The casing 46 also houses therein a web camera 48 disposed near the radiation source 18b. A USB terminal 50 for connection to a USB cable (not shown) and the connection terminal 43 are disposed on one end of the casing 46, whereas the connection terminal 45 is disposed on the other end of the casing 46. The grip 28 is disposed on an arcuate side surface of the casing 46 and incorporates therein a touch sensor (gripped state sensor) 52.

The touch sensor 52 comprises an electrostatic capacitance sensor or a resistance-film contact sensor. When the doctor 26 grips the grip 28 and contacts electrodes (not shown) of the touch sensor 52 with the hand, the touch sensor 52 outputs a detection signal indicating that the hand and the electrodes are held in contact with each other.

The touch sensor 52 may alternatively be a mechanical switch such as a push switch or the like. If the touch sensor 52 is a mechanical switch, then when the doctor 26 grips the grip 28 and contacts the mechanical switch, the touch sensor 52 outputs a detection signal indicating that the mechanical switch has been turned on or off.

When the doctor 26 grips the grip 28 and orients the radiation output device 20 toward the subject 14, the radiation output device 20 is ready to capture a camera image of the imaging range 84 with the web camera 48 (see FIG. 3), as well as to emit radiation 16a through 16c from the radiation sources 18a through 18c (see FIG. 5B). The radiation output device 20 can emit radiation 16a through 16c simultaneously or sequentially from the radiation sources 18a through 18c. While the radiation output device 20 and the radiation detecting device 22 are integrally combined with each other by the holders 35, 37 and the connection terminals 39, 41, 43, 45, the radiation output device 20 does not permit the radiation sources 18a through 18c to emit radiation, i.e., the radiation sources 18a through 18c are inhibited from emitting radiation 16a through 16c, even if the doctor 26 grips the grip 28.

When the doctor 26 grips the grip 28 and orients the radiation output device 20 toward the subject 14, the web camera 48 is capable of capturing an image of the imaging range 84 including the imaging area 36. If the region to be imaged of the subject 14 is positioned properly within the imaging area 36, then since the region to be imaged of the subject 14 is positioned within the imaging range 84, the web camera 48 can capture a camera image, which includes the region to be imaged of the subject 14. The web camera 48 is capable of capturing successive camera images (a moving image) or intermittent camera images (still images) at certain time intervals, or can capture a camera image (still image) at a certain time.

Figure 7A:
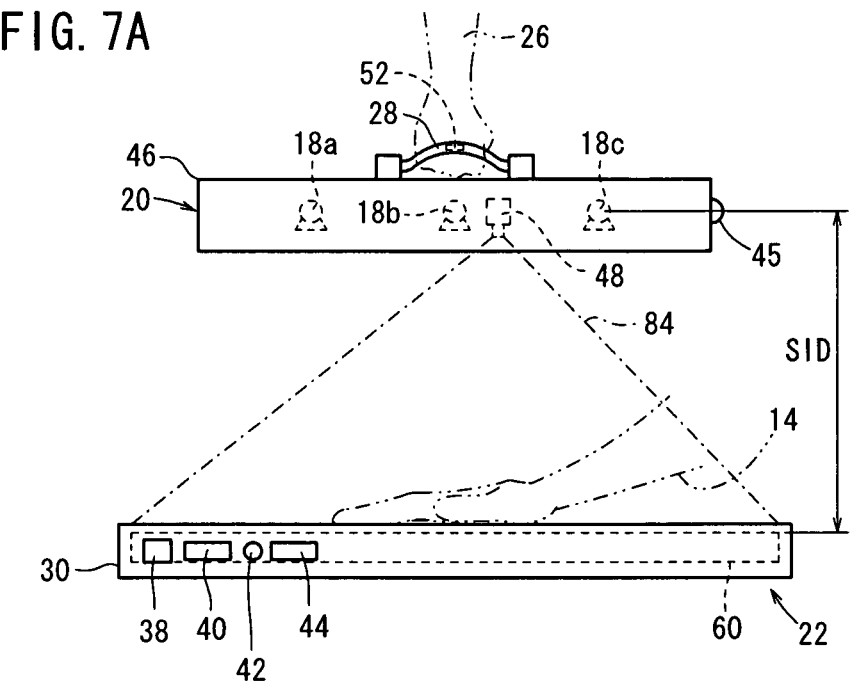
FIG. 7A is a side elevational view showing the manner in which a region to be imaged of the subject is imaged by the web camera.
Figure 7B:
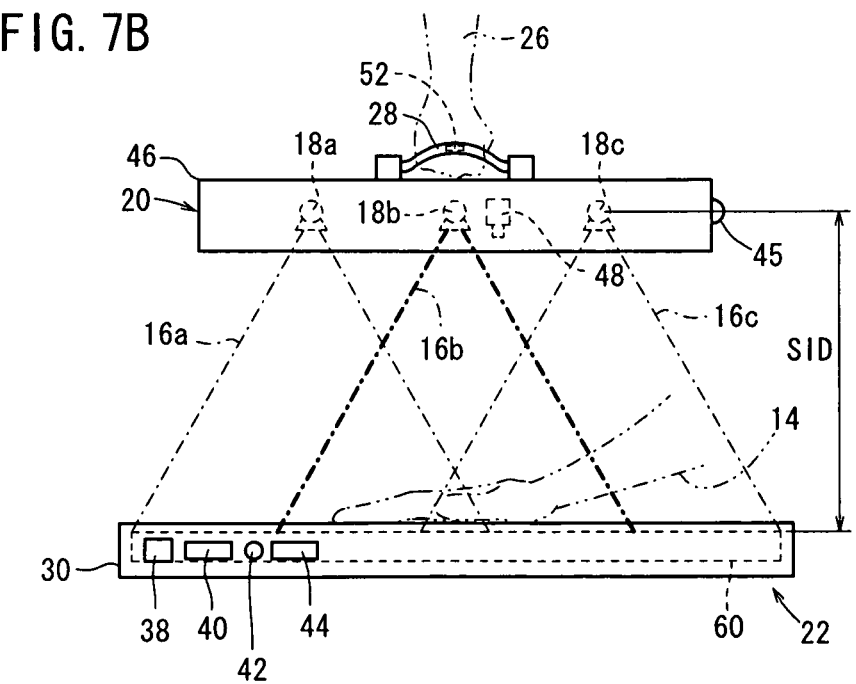
FIG. 7B is a side elevational view showing the manner in which the region to be imaged of the subject is irradiated.

FIG. 6A shows the manner in which the web camera 48 captures an image of the chest of the subject 14, which is a relatively large region to be imaged, whereas FIG. 6B shows the manner in which a radiographic image of the chest of the subject 14 is captured. FIG. 7A shows the manner in which the web camera 48 captures an image of a hand of the subject 14, which is a relatively small region to be imaged, whereas FIG. 7B shows the manner in which a radiographic image of the hand of the subject 14 is captured. The three radiation sources 18a through 18c are arranged in the casing 46 of the radiation output device 20 along a horizontal direction in FIGS. 6A through 7B, i.e., along the longitudinal direction of the casing 46. In a case where radiation 16a through 16c is applied from the respective radiation sources 18a through 18c to the region to be imaged of the subject 14, such radiation 16a through 16c passes through the region to be imaged and then through the surface (the imaging area 36 in FIGS. 3 through 4B) of the housing 30 of the radiation detecting device 22, and the radiation is led to a radiation detector 60 housed in the housing 30. The radiation detector 60, which is either a radiation detector of an indirect conversion type or a radiation detector of a direct conversion type, detects radiation 16a through 16c and converts such radiation 16a through 16c into a radiographic image.

If the portable radiation output device 20 is operated in a hospital or at a site outside of a hospital, then difficulty may be experienced in preparing an appropriate external power supply. Each of the radiation sources 18a through 18c of the radiation output device 20 should preferably be a battery-powered radiation source. Consequently, the field-emission radiation sources 18a through 18c should be small and light-weight radiation sources, for emitting a smaller dose of radiation than is possible with a thermionic emission radiation source, which typically is used in an image capturing chamber of the radiological department of the hospital.

At the site where the radiographic image capturing system 10 is used, the doctor 26 is required to keep the radiation output device 20 as close to the subject 14 as possible, thereby reducing the source-to-image distance (SID) between the radiation sources 18a through 18c and the radiation detector 60 in the radiation detecting device 22 when radiographic images of the subject 14 are captured. As a result, radiation 16a through 16c emitted from the respective radiation sources 18a through 18c is applied within a narrow irradiation range, and the doses (exposure doses) of radiation 16a through 16c applied to the subject 14 are small. Therefore, the radiographic image capturing system 10 may fail to capture radiation images based on an exposure dose, which is large enough to enable the doctor 26 to read radiation images correctly.

In the case where the subject 14 is irradiated with an optimum dose (exposure dose) of radiation depending on the region to be imaged of the subject 14 and the thickness of the region to be imaged, the radiographic image capturing system 10 can produce a radiographic image based on an exposure dose, which is large enough to enable the doctor 26 to read the resultant radiation image correctly, and the subject 14 can avoid undue exposure to radiation.

According to the present embodiment, the radiation output device 20 includes at least two radiation sources (three radiation sources 18a through 18c as shown in FIGS. 5A through 7B) together with the web camera 48. For capturing a radiographic image of the subject 14, a region to be imaged of the subject 14 is positioned between the radiation output device 20 and the radiation detecting device 22, and the web camera 48 is operated to image the imaging range 84, thereby capturing a camera image of the imaging range 84. Then, the region to be imaged of the subject 14, which is included within the captured camera image, is identified. As described above, since the region to be imaged of the subject 14 is positioned within the imaging area 36 of the radiation detecting device 22, and the web camera 48 captures a camera image of the imaging range 84 including the imaging area 36, and further since the region to be imaged of the subject 14 is properly positioned as shown in FIGS. 4A, 4B, 6A and 7A, the region to be imaged of the subject 14, which is positioned within the imaging range 84, is imaged, and hence a camera image, which includes therein the region to be imaged of the subject 14, is reliably captured.

Then, according to the present embodiment, doses of radiation emitted from all of the radiation sources 18a through 18c in the radiation output device 20 are weighted based on the region to be imaged of the subject 14, which has been identified from the camera image. Thereafter, the radiation sources 18a through 18c emit and apply radiation to the subject 14 based on the weighted doses (main exposure mode) in order to capture a radiographic image in the main exposure mode (main exposure image).

More specifically, for capturing a main exposure image of a relatively large region to be imaged (e.g., the chest) as shown in FIG. 6B (main exposure mode), a relatively wide range (overall imaging area 36) needs to be irradiated with radiation 16a through 16c so that the entire chest of the subject 14 will be irradiated with radiation 16a through 16c. In addition, the accumulated dose of radiation applied to the subject 14 in the main exposure mode needs to be an optimum dose depending on the chest and the thickness thereof, i.e., a dose of radiation that is appropriate for the doctor 26 to be able to read the resultant radiographic image.

According to the present embodiment, in the main exposure mode for imaging a relatively large region to be imaged of the subject 14, as shown in FIG. 6B, doses of radiation to be emitted from the radiation sources 18a through 18c are weighted such that such doses of radiation 16a, 16c emitted from the radiation sources 18a, 18c at the ends are of a maximum dose level, as indicated by the thick dot-and-dash lines in FIG. 6B, whereas the dose of radiation 16b emitted from the radiation source 18b at the center is of a lower dose level, just enough to make up for any shortage of the maximum dose level, as indicated by the thin dot-and-dash lines in FIG. 6B. Based on such weighted doses, the radiation sources 18a through 18c apply radiation 16a through 16c simultaneously and sequentially.

Radiation, which is emitted from adjacent ones of the radiation sources 18a through 18c, has respective irradiation ranges, which overlap with each other so as to irradiate a region to be imaged of the subject 14 with the radiation without any radiation-free gaps.

For capturing a main exposure image of a relatively small region to be imaged (right hand) shown in FIG. 7B (main exposure mode), since the right hand is placed in a central portion of the imaging area 36, only a relatively narrow range including the central portion is irradiated with radiation. In this case, the accumulated dose of radiation applied to the subject 14 in the main exposure mode needs to be an optimum dose depending on the right hand and the thickness thereof, i.e., a dose of radiation that is appropriate to enable the doctor 26 to be able to read the resultant radiographic image.

According to the present embodiment, in the main exposure mode for imaging a relatively small region to be imaged of the subject 14, as shown in FIG. 7B, doses of radiation emitted from the radiation sources 18a through 18c are weighted, such that the dose of radiation 16b emitted from the radiation source 18b at the center is of a maximum dose level, as indicated by the thick dot-and-dash lines in FIG. 7B, whereas the doses of radiation 16a, 16c emitted from the radiation sources 18a, 18c at the ends are of a lower dose level, just enough to make up for any shortage of the maximum dose level, as indicated by the thin dot-and-dash lines in FIG. 7B. Based on the weighted doses, the radiation sources 18a through 18c apply radiation 16a through 16c simultaneously and sequentially.

The maximum dose level refers to a dose that is relatively the highest among doses of the radiation 16a through 16c as compared with each other, whereas the low dose level is relatively the smallest among doses of the radiation 16a through 16c as compared with each other. Such dose levels should not exceed the optimum dose level referred to above. According to the present embodiment, in the main exposure mode shown in FIGS. 6B and 7B, the doses of radiation emitted from the radiation sources 18a through 18c are weighted, such that the accumulated dose of radiation applied to the subject 14 at the time that the subject 14 is irradiated with radiation 16a through 16c equals the optimum dose.

It is preferable for the radiation sources 18a through 18c to simultaneously apply radiation 16a through 16c respectively, due to the shorter time required to capture a radiographic image of the subject 14. However, it may be difficult for the radiation sources 18a through 18c to simultaneously apply radiation 16a through 16c respectively, depending on the ability to supply electric power to the radiation sources 18a through 18c (consumption of electric power by the radiation output device 20) and image capturing conditions of the subject 14 (the number of radiographic images to be captured of the subject 14).

If it is difficult for the radiation sources 18a through 18c to simultaneously apply radiation 16a through 16c respectively, then the radiation sources 18a through 18c may sequentially apply radiation 16a through 16c respectively, so as to reliably capture a radiographic image of the subject 14. If the radiation sources 18a through 18c sequentially apply radiation 16a through 16c respectively, then a central portion of the region to be imaged, which has been positioned, may be irradiated initially, and thereafter, other portions may be irradiated, for thereby reducing blurring of the radiographic image, which may be caused by movement of the region to be imaged during the image capturing process. Alternatively, the region to be imaged may be irradiated initially with radiation, indicated by the thick dot-and-dash lines in FIG. 6B or 7B, and then be irradiated with radiation, as indicated by the thin dot-and-dash lines in FIG. 6B or 7B.

According to the present embodiment, therefore, simultaneous or sequential application of radiation 16a through 16c may be selected depending on the ability to supply electric power to the radiation sources 18*a* through 18*c* and image capturing conditions of the subject 14.

As described above, while the region to be imaged of the subject 14 is included within the imaging range 84 of the web camera 48, the web camera 48 captures a camera image of the imaging range 84, and doses of radiation 16*a* through 16*c* to be emitted from the radiation sources 18*a* through 18*c* are weighted based on the camera image, which covers the region to be imaged. In other words, doses of radiation are weighted on the premise that the region to be imaged of the subject 14 is covered by the camera image. Consequently, if a camera image is captured in a state that the region to be imaged of the subject 14 is not included within the imaging range 84 due to a reduced SID, for example, then the doses of radiation are not weighted based on the camera image.

In a case where radiation 16*a* through 16*c*, the doses of which have been weighted, is applied to the region to be imaged of the subject 14, the radiation 16*a* through 16*c* is transmitted through the region to be imaged, detected by the radiation detector 60, and then the radiation 16*a* through 16*c* is converted into a radiographic image (main exposure image).

During the main exposure mode shown in FIGS. 6B and 7B, radiation 16*a* through 16*c* emitted from the radiation sources 18*a* through 18*c* is applied to the subject 14, whereas the web camera 48 does not capture a camera image. However, the web camera 48 may capture a camera image while radiation 16*a* through 16*c* is being applied to the subject 14.

Figure 8:
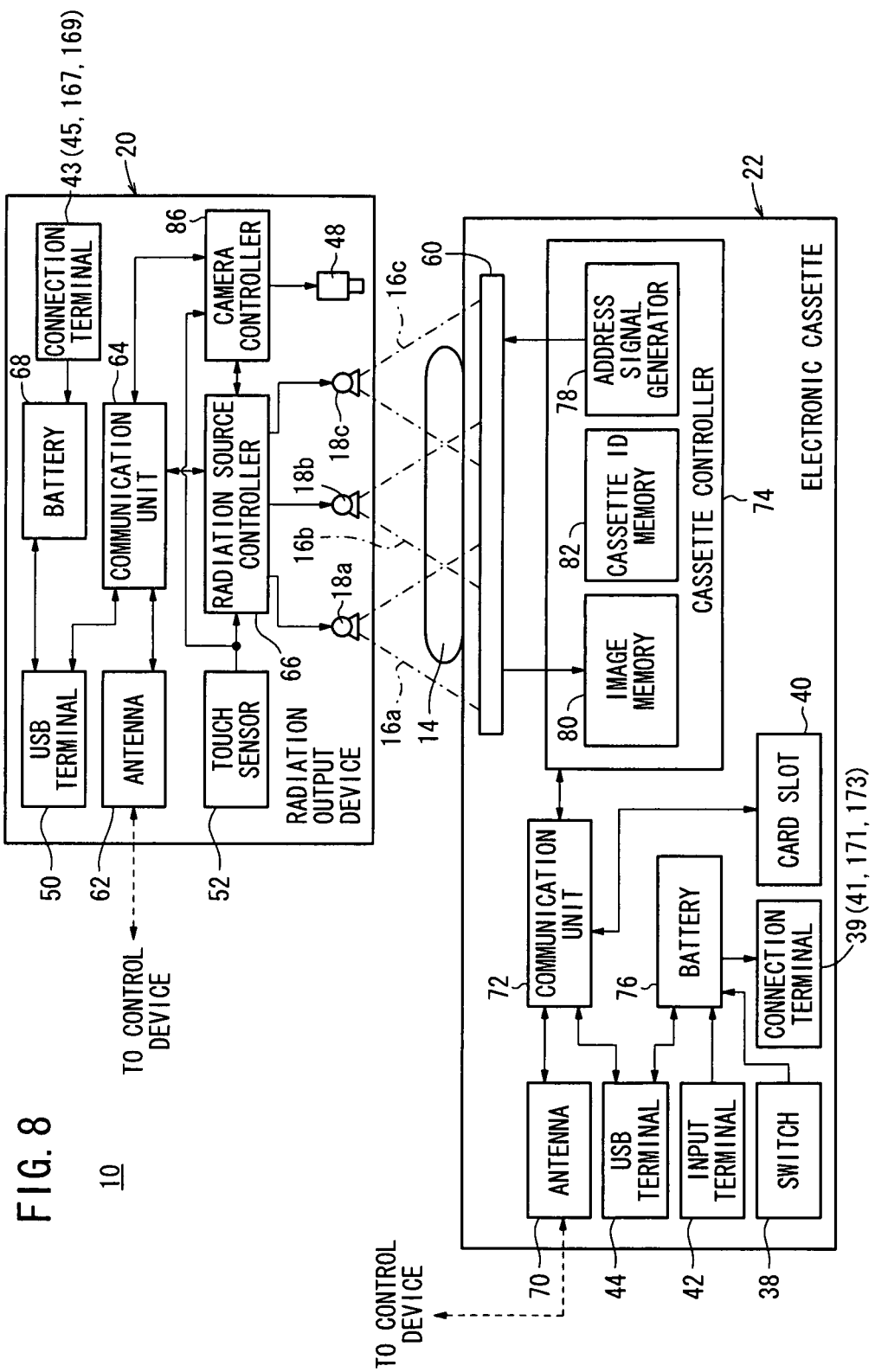
FIG. 8 is a block diagram of the radiation output device and the radiation detecting device shown in FIG. 8.

Internal details of the radiation output device 20, the radiation detecting device 22, and the control device 24 of the radiographic image capturing system 10 will be described in detail below with reference to the block diagrams shown in FIGS. 8, 9 and 10.

The radiation output device 20 further includes a communication unit 64 for sending signals to and receiving signals from the control device 24 by way of wireless communications through an antenna 62, a radiation source controller 66 for controlling the radiation sources 18*a* through 18*c*, a camera controller 86 for controlling the web camera 48, and a battery 68 for supplying electric power to various components of the radiation output device 20.

The battery 68 supplies electric power at all times to the touch sensor 52, the communication unit 64, and the radiation source controller 66. In a case where the touch sensor 52 outputs a detection signal to the radiation source controller 66, at a time that the doctor 26 grips the grip 28, the radiation source controller 66 controls the battery 68 in order to supply electric power to various components of the radiation output device 20. The touch sensor 52 also outputs the detection signal to the camera controller 86. In response to the detection signal from the touch sensor 52, the camera controller 86 controls the web camera 48 in order to start capturing a camera image of the imaging range 84, and then to send the captured camera image to the control device 24 wirelessly via the communication unit 64 and the antenna 62.

In a state that the connection terminals 39, 43 and the connection terminals 41, 45 are electrically connected to each other, and the radiation output device 20 and the radiation detecting device 22 are integrally combined with each other, the battery 68 can be charged by a battery 76 of the radiation detecting device 22. At this time, the radiation source controller 66 does not permit the battery 68 to supply, i.e., inhibits the battery 68 from supplying, electric power to the radiation sources 18*a* through 18*c*, even if a detection signal is received from the touch sensor 52. The radiation source controller 66 controls the battery 68 in order to start supply of electric power to the radiation sources 18*a* through 18*c*, in response to a detection signal received from the touch sensor 52 when the connection terminals 39, 43 and the connection terminals 41, 45 are electrically disconnected from each other, such that the radiation output device 20 and the radiation detecting device 22 are separated from each other.

If a cable (not shown) such as a communication cable, a USB cable, or a cable according to IEEE1394, is connected to the radiation output device 20, then the radiation output device 20 can send signals to and receive signals from an external circuit, or may be supplied with electric power via the cable. For example, if a USB cable (not shown) is connected to the USB terminal 50, for example, then the battery 68 can be charged by electric power supplied from an external circuit via the USB cable, and the communication unit 64 can send signals to and receive signals from an external circuit via the USB cable.

The radiation detecting device 22 further includes a communication unit 72 for sending signals to and receiving signals from the control device 24 by way of wireless communications through an antenna 70, a cassette controller 74 for controlling the radiation detector 60, and the battery 76 for supplying electric power to various components of the radiation detecting device 22.

The battery 76 supplies electric power at all times to the cassette controller 74 and the communication unit 72. If the doctor 26 operates (turns on) the switch 38, the battery 76 is capable of supplying electric power to various components of the radiation detecting device 22.

If a cable (not shown) such as a communication cable, a USB cable, or a cable according to IEEE1394, is connected to the radiation detecting device 22, then the radiation detecting device 22 can send signals to and receive signals from an external circuit, or can be supplied with electric power via the cable. For example, if a USB cable (not shown) is connected to the USB terminal 44, for example, then the battery 76 can be charged by electric power supplied from an external circuit via the USB cable, and the communication unit 72 can send signals to and receive signals from an external circuit via the USB cable.

The cassette controller 74 includes an address signal generator 78 for supplying address signals to the radiation detector 60 for reading a radiographic image, an image memory 80 for storing the radiographic image read from the radiation detector 60, and a cassette ID memory 82 for storing cassette ID information, which identifies the radiation detecting device 22.

A circuit arrangement of the radiation detecting device 22, wherein the radiation detector 60 is of an indirect conversion type, will be described in detail below with reference to FIG. 10.

The radiation detector 60 comprises an array of thin-film transistors (TFTs) 98 arranged in rows and columns, and a photoelectric conversion layer 96 including pixels 90 and made of a material such as amorphous silicon (a-Si) or the like for converting visible light into electric signals. The photoelectric conversion layer 96 is disposed on the array of TFTs 98. When radiation is applied to the radiation detector 60, the pixels 90, which are supplied with a bias voltage Vb from the battery 76 (see FIG. 8), generate electric charges by converting visible light into analog electric signals, and then store the generated electric charges. Then, when the TFTs 98 are turned on along each row at a time, the stored electric charges are read from the pixels 90 as an image signal.

The TFTs 98 are connected to respective pixels 90. Gate lines 92, which extend parallel to the rows, and signal lines 94, which extend parallel to the columns, are connected to the TFTs 98. The gate lines 92 are connected to a line scanning driver 100, and the signal lines 94 are connected to a multiplexer 102. The gate lines 92 are supplied with control signals Von, Voff for turning on and off the TFTs 98 along the rows from the line scanning driver 100. The line scanning driver 100 includes a plurality of switches SW1 for switching between the gate lines 92, and an address decoder 104 for outputting a selection signal for selecting one of the switches SW1 at a time. The address decoder 104 is supplied with an address signal from the address signal generator 78 (see FIG. 8) of the cassette controller 74.

The signal lines 94 are supplied with electric charges stored by the pixels 90 via the TFTs 98, which are arranged in columns. The electric charges supplied to the signal lines 94 are amplified by amplifiers 106, which are connected respectively to the signal lines 94. The amplifiers 106 are connected through respective sample and hold circuits 108 to the multiplexer 102. The multiplexer 102 includes a plurality of switches SW2 for successively switching between the signal lines 94, and an address decoder 110 for outputting a selection signal for selecting one of the switches SW2 at a time. The address decoder 110 is supplied with an address signal from the address signal generator 78 of the cassette controller 74. The multiplexer 102 has an output terminal connected to an A/D converter 112. A radiographic image signal, which is generated by the multiplexer 102 based on electric charges from the sample and hold circuits 108, is converted by the A/D converter 112 into a digital image signal representing radiographic image information, which is supplied to the cassette controller 74.

The TFTs 98, which function as switching devices, may be combined with another image capturing device, such as a CMOS (Complementary Metal-Oxide Semiconductor) image sensor or the like. Alternatively, the TFTs 98 may be replaced with a CCD (Charge-Coupled Device) image sensor for shifting and transferring electric charges with shift pulses, which correspond to gate signals in the TFTs.

Figure 9:
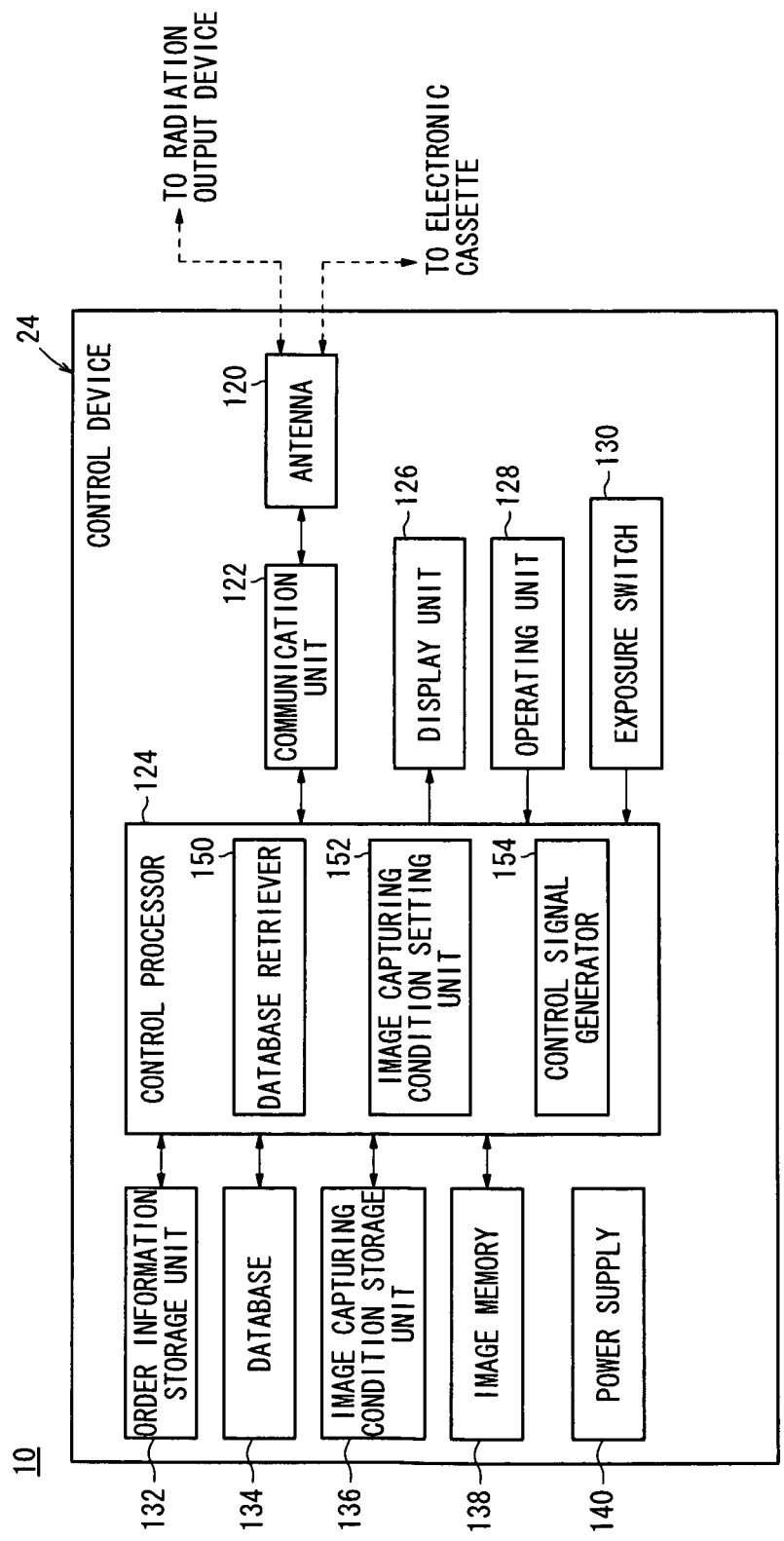
FIG. 9 is a block diagram of a control device of the radiographic image capturing system shown in FIG. 1.
Figure 10:
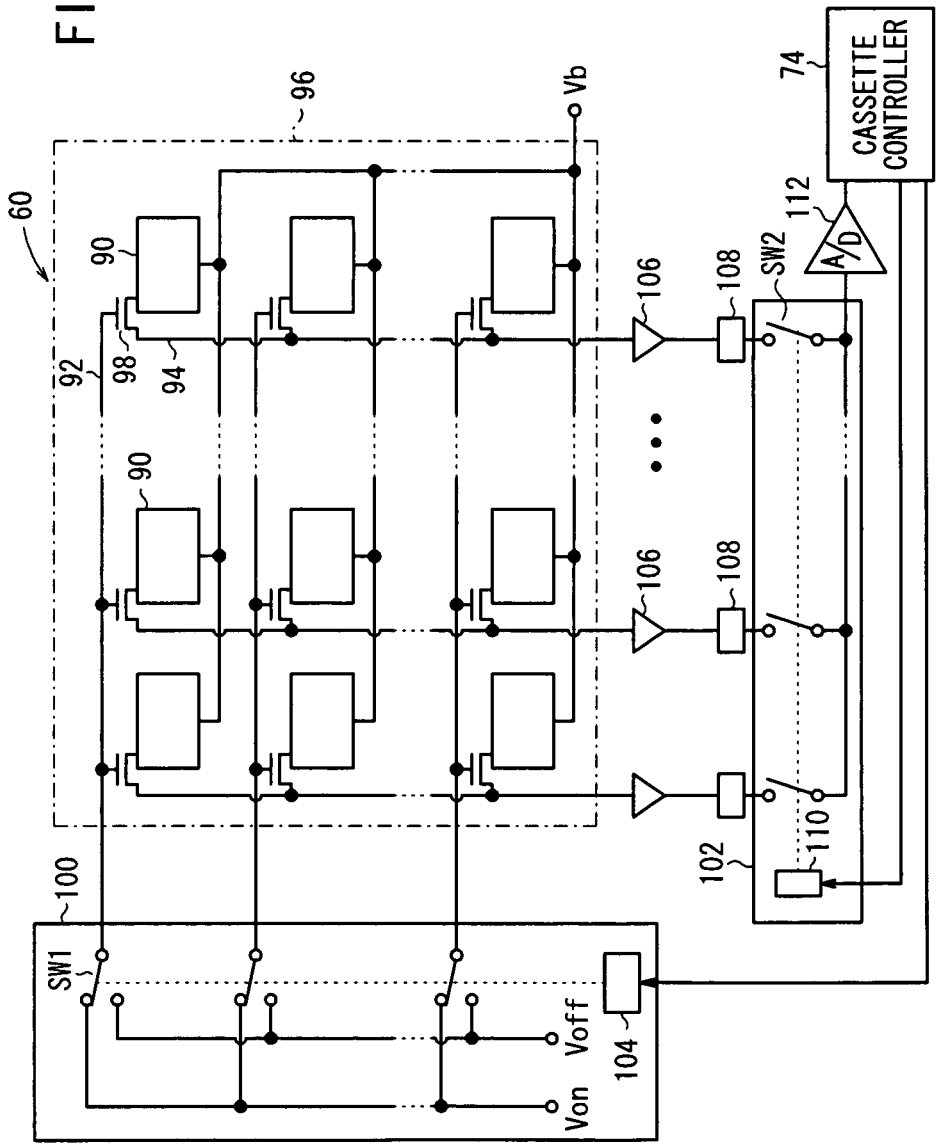
FIG. 10 is a block diagram of a circuit arrangement of the radiation detecting device shown in FIG. 8.

As shown in FIG. 9, the control device 24 includes a communication unit 122 for sending signals to and receiving signals from the communication unit 64 of the radiation output device 20 and the communication unit 72 of the radiation detecting device 22 by way of wireless communications through an antenna 120 and the antennas 62, 70, a control processor 124 for performing a prescribed control process on the radiation output device 20 and the radiation detecting device 22, a display unit 126 such as a display panel or the like, an operating unit 128 including a keyboard, a mouse, etc., an exposure switch 130, which can be turned on by the doctor 26 in order to start emitting radiation 16a through 16c from the radiation sources 18a through 18c, an order information storage unit 132 for storing order information requesting capture of a radiographic image of the subject 14, a database 134 for storing various data concerning weighting of doses of radiation 16a through 16c, an image capturing condition storage unit 136 for storing image capturing conditions (main exposure conditions) under which a region to be imaged of the subject 14 is to be irradiated with radiation 16a through 16c, an image memory 138 for storing radiographic images (main exposure images) transmitted from the radiation detecting device 22 by way of wireless communications, and a power supply 140 for supplying electric power to various components of the control device 24.

The order information is generated by the doctor 26 for a radiology information system (RIS), not shown, which generally manages radiographic images and other information that are handled in the radiological department of the hospital, or for a hospital information system (HIS), not shown, which generally manages medical information in the hospital. Such order information includes subject information for identifying the subject 14, including the name, age, gender, etc., information concerning the radiation output device 20 and the radiation detecting device 22, which are used to capture radiographic images, and information concerning a region to be imaged of the subject 14. Such image capturing conditions refer to various conditions under which a region to be imaged of the subject 14 is irradiated with radiation 16a through 16c, including tube voltages and tube currents of the radiation sources 18a through 18c, radiation exposure times of the radiation 16a through 16c, etc.

If the control device 24 comprises a console placed in the image capturing chamber of the radiological department, then the console (control device 24) acquires order information from the RIS or the HIS, and stores the acquired order information in the order information storage unit 132.

If the control device 24 comprises a portable terminal, which is carried to and used at a site outside of the hospital, then (1) the doctor 26 may operate the operating unit 128 at the site to provisionally register order information in the order information storage unit 132, (2) order information may be acquired from the RIS or the HIS and then stored in the order information storage unit 132 in the hospital before the control device 24 is carried to the site, or (3) order information may be received from the hospital through a wireless link established between the control device 24 at the site and the hospital after the control device 24 has been carried to the site, and then stored in the order information storage unit 132.

The control processor 124 includes a database retriever 150 for retrieving desired data corresponding to the region to be imaged of the subject 14 from the database 134, an image capturing condition setting unit 152 for setting image capturing conditions based on the data received by the database retriever 150 and the order information, and a control signal generator 154 for generating an exposure control signal for starting emission of radiation 16a through 16c from the radiation sources 18a through 18c when the doctor 26 turns on the exposure switch 130.

Figure 11:
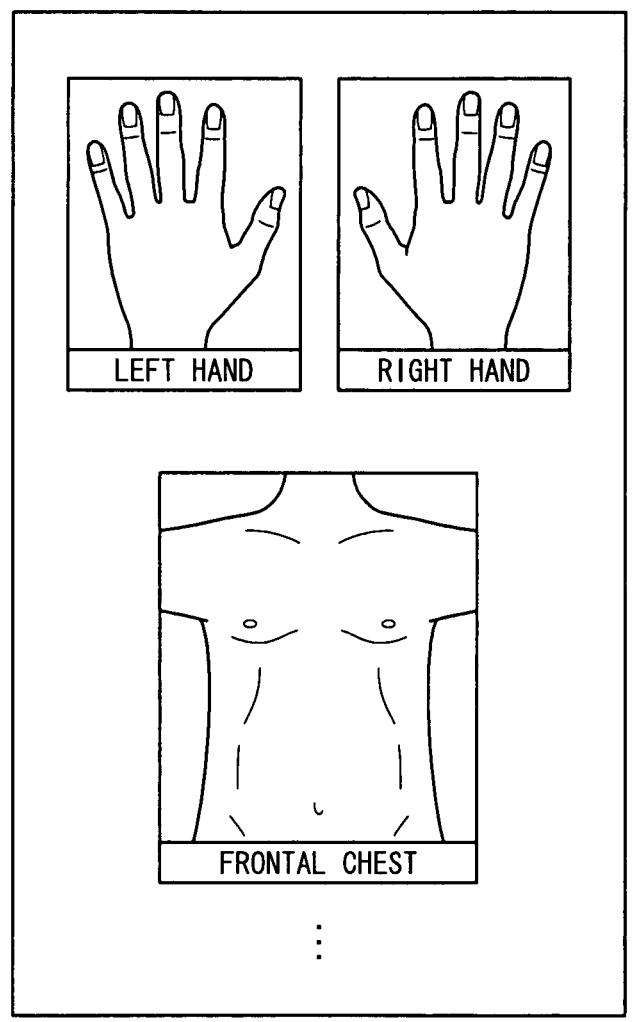
FIG. 11 is a diagram showing, by way of example, object data that is stored in a database shown in FIG. 9.

FIGS. 11 through 13 show object data representative of a plurality of regions to be imaged, and tables of various data concerning weighting of the doses of radiation 16a through 16c.

FIG. 11 shows object data representative of camera images of a plurality of regions. The object data shown in FIG. 11 includes object data of a chest, as a relatively large region to be imaged, and object data of right and left hands, as relatively small regions to be imaged.

FIG. 12 shows a table that stores therein a plurality of regions to be imaged, thicknesses of the respective regions to be imaged, image capturing techniques for the respective regions to be imaged, and optimum radiation doses (optimum radiation dose data) therefor. The image capturing techniques refer to information representative of orientations of the regions to be imaged with respect to the radiation detecting device 22, and directions along which the regions to be imaged are irradiated with radiation 16a through 16c. More specifically, FIG. 12 shows by way of example data representing a chest, as a relatively large region to be imaged, data representing a hand, as a relatively small region to be imaged, image capturing techniques (a process for capturing a radiographic image of a frontal chest region, and a process for capturing a radiographic image of the back of the hand), thicknesses of the regions to be imaged, and optimum radiation dose data therefor.

FIG. 13 shows a table storing a plurality of regions to be imaged and image capturing techniques for the respective regions to be imaged, the numbers of radiation sources housed in the radiation output device 20, and weighting data for doses of radiation to be emitted from the respective radiation sources. More specifically, FIG. 13 shows by way of example data representing a chest and a hand, which serve as regions to be imaged, two and three radiation sources used to emit radiation, and weighting data for doses of radiation to be emitted from the respective radiation sources. If the number of radiation sources used is three, then the weighting data "A" corresponds to the radiation source 18a, the weighting data "B" corresponds to the radiation source 18b, and the weighting data "C" corresponds to the radiation source 18c. If the number of radiation sources used is greater than three, then the number of weighting data in the table shown in FIG. 13 increases depending on the number of radiation sources.

The database 134 is capable of storing various data concerning image capturing processes that can be carried out by the radiographic image capturing system 10. Data stored in the database 134 can be used even if the subject 14 to be imaged is changed, the region to be imaged of the subject 14 is changed, or a plurality of subjects 14 are imaged sequentially.

A region to be imaged of the subject 14, the thickness of the region to be imaged, and an image capturing technique are manually entered by the doctor 26 through the operating unit 128, or alternatively may be included in the order information. When the region to be imaged, the thickness thereof, and the image capturing technique, which are manually entered by the doctor 26 through the operating unit 128, are stored as part of the order information in the order information storage unit 132, the order information is edited.

For capturing a radiographic image of the region to be imaged of the subject 14 (image capturing technique), which is represented by the order information, the database retriever 150 performs the following processes:

First, the database retriever 150 automatically retrieves, from the database 134, object data that agree with the region to be imaged of the subject 14 in the camera image, which is received via the antenna 120 and the communication unit 122, and identifies a region to be imaged, which is represented by the object data that agree with the region to be imaged, as a region to be imaged of the subject 14 during a process of capturing a radiographic image (main exposure mode). More specifically, the database retriever 150 matches the region to be imaged in the camera image and each object data according to a known pattern matching process, for example, and if a correlation (degree of coincidence) between the two images exceeds a predetermined threshold value, identifies a region to be imaged, which is represented by object data the degree of coincidence of which has exceeded the threshold value, as a region to be imaged of the subject 14 in the main exposure mode.

In a case where the database retriever 150 retrieves, from the database 134, a plurality of object data, which are highly likely to agree with the region to be imaged in the camera image, i.e., a plurality of object data the degree of coincidence of which has exceeded the threshold value, then the database retriever 150 may display the camera image and the plural object data on the display unit 126. The doctor 26 may confirm the camera image and the object data displayed on the display unit 126, and operate the operating unit 128 in order to select object data that appear to agree most closely with the region to be imaged in the camera image. The database retriever 150 may then identify the region to be imaged, which is represented by the selected object data, as a region to be imaged of the subject 14.

The database retriever 150 also identifies the thickness of the region to be imaged of the subject 14, and an image capturing technique therefor. More specifically, if the region to be imaged of the subject 14, which is included in the order information, and the identified region to be imaged of the subject 14 are in agreement with each other, then the database retriever 150 identifies the thickness of the region to be imaged of the subject 14 and the image capturing technique therefor, which are included in the order information, as the thickness of the region to be imaged of the subject 14 and the image capturing technique therefor in the main exposure mode.

If the identified region to be imaged of the subject 14 is not in agreement with the region to be imaged of the subject 14, which is included in the order information, or if a thickness of the region to be imaged of the subject 14 and an image capturing technique therefor are yet to be set, then the database retriever 150 displays the identified region to be imaged of the subject 14 and the identified image capturing technique on the display unit 126. The doctor 26 confirms the identified region to be imaged of the subject 14 and the identified image capturing technique, which are displayed, and operates the operating unit 128 in order to enter a thickness of the region to be imaged of the subject 14 and an image capturing technique therefor. The database retriever 150 identifies the entered thickness of the region to be imaged of the subject 14 and the entered image capturing technique therefor, as the thickness of the region to be imaged of the subject 14 and the image capturing technique therefor in the main exposure mode. The database retriever 150 also stores the entered thickness of the region to be imaged of the subject 14 and the entered image capturing technique therefor, as part of the order information in the order information storage unit 132.

The database retriever 150 also automatically retrieves, from the table shown in FIG. 12, optimum radiation dose data based on the identified region to be imaged of the subject 14, the thickness thereof, and the image capturing technique therefor. The database retriever 150 also automatically retrieves, from the table shown in FIG. 13, optimum weighting data based on the region to be imaged of the subject 14, the image capturing technique therefor, and the number of radiation sources used in the radiation output device 20. Then, the database retriever 150 outputs to the image capturing condition setting unit 152 the retrieved optimum radiation dose data and the retrieved optimum weighting data, and the order information, which includes the region to be imaged of the subject 14, the thickness thereof, and the image capturing technique therefor, which have been used to retrieve the optimum radiation dose data and the optimum weighting data.

If the database retriever 150 retrieves, from the database 134, a plurality of candidates as optimum radiation dose data and optimum weighting data, then the database retriever 150 may display a plurality of candidates and the order information on the display unit 126. The doctor 26 may confirm the plural candidates and the order information displayed on the display unit 126, and operate the operating unit 128 in order to select data that appears to be optimum for the main exposure mode. The database retriever 150 may then output the optimum radiation dose data and the optimum weighting data, which the doctor 26 has selected from among the plural candidates, and the order information to the image capturing condition setting unit 152.

The database retriever 150 may determine whether or not the region to be imaged of the subject 14 is included within, but exceeds, the camera image, based on a comparison between the region to be imaged, which is represented by the order information, and the region to be imaged, which is represented by the camera image. If the region to be imaged of the subject 14 is not included within the camera image, then the database retriever 150 may judge that optimum radiation dose data and optimum weighting data cannot be retrieved, so as not to carry out the above processes.

The image capturing condition setting unit 152 automatically sets image capturing conditions (main exposure conditions) for the region to be imaged of the subject 14 in the main exposure mode, based on optimum radiation dose data and optimum weighting data retrieved by the database retriever 150 and the order information, and stores the set image capturing conditions in the image capturing condition storage unit 136.

In the main exposure mode, the image capturing condition setting unit 152 may display the order information, the optimum radiation dose data, and the optimum weighting data retrieved by the database retriever 150 on the display unit 126. The doctor 26 may then confirm the order information, the optimum radiation dose data, and the optimum weighting data, which have been displayed, and operate the operating unit 128 in order to change details of the optimum radiation dose data and the optimum weighting data depending on the order information, the state of the subject 14, or the image capturing technique. The image capturing condition setting unit 152 may set main exposure conditions based on the optimum radiation dose data and the optimum weighting data, which have been changed.

[Operations of the Present Embodiment (Radiographic Image Capturing Method)]

The radiographic image capturing system 10 according to the present embodiment is basically constructed as described above. Next, operations (a radiographic image capturing method) of the radiographic image capturing system 10 shall be described below with reference to the flowcharts shown in FIGS. 14 and 15.

Figure 14:
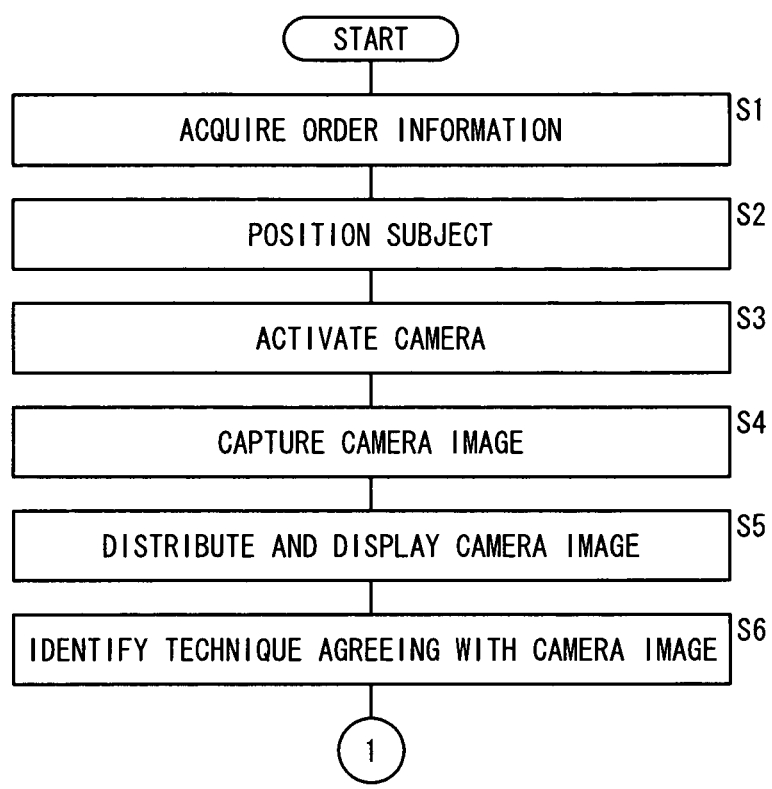
FIG. 14 is a flowchart of an operation sequence of the radiographic image capturing system shown in FIG. 1.

In step S1 shown in FIG. 14, the control processor 124 of the control device 24 acquires order information from an external source, and stores the acquired order information in the order information storage unit 132. If the control device 24 is a console, which is placed in the image capturing chamber of a radiological department, then the control device 24 may acquire order information from the RIS or the HIS. If the control device 24 is a portable terminal that can be carried to and used at a site outside of the hospital, then the doctor 26 may operate the operating unit 128 in order to register order information, or order information may be acquired from the RIS or the HIS in the hospital before the control device 24 is carried to the site. Alternatively, order information may be received from the hospital through a wireless link established between the control device 24 at the site and the hospital, after the control device 24 has been carried to the site.

If the order information does not include the thickness of the region to be imaged and the image capturing technique therefor in step S1, then the doctor 26 operates the operating unit 128 in order to enter the thickness of the region to be imaged and the image capturing technique therefor. The order information storage unit 132 stores the entered thickness of the region to be imaged and the entered image capturing technique therefor as part of the order information, thereby editing the order information.

In step S2, when the doctor 26 turns on the switch 38 of the radiation detecting device 22, the battery 76 supplies electric power to various components of the radiation detecting device 22, thereby activating the radiation detecting device 22. The cassette controller 74 sends an activation signal, which indicates that the radiation detecting device 22 has been activated in its entirety, via a wireless link to the control device 24. The battery 76 also applies a bias voltage Vb to the pixels 90 of the radiation detector 60.

In the case where the radiation output device 20 and the radiation detecting device 22 are carried to a site, the connection terminals 39, 43 are held in interfitting engagement with each other, and the connection terminals 41, 45 also are held in interfitting engagement with each other. Therefore, the radiation output device 20 is held between the holders 35, 37 of the radiation detecting device 22, and the radiation output device 20 and the radiation detecting device 22 are integrally combined with each other (see FIG. 2A). At this time, the battery 76 charges the battery 68 through the connection terminals 39, 41, 43, 45.

For positioning the region to be imaged of the subject 14, the doctor 26 releases the connection terminals 39, 43 from interfitting engagement with each other, and also releases the connection terminals 41, 45 from interfitting engagement with each other. The radiation output device 20 is separated from the radiation detecting device 22, whereby the radiation output device 20 and the radiation detecting device 22 become disconnected from each other (see FIG. 2B). At this time, the battery 76 stops charging the battery 68.

Then, the doctor 26 positions the region to be imaged of the subject 14, such that the central position of the region to be imaged of the subject 14 and the central position of the imaging area 36 become aligned with each other, and the region to be imaged of the subject 14 is included within the imaging area 36 (see FIGS. 4A and 4B). Thereafter, the doctor 26 grips the grip 28 and orients the radiation output device 20 toward the region to be imaged of the subject 14, so that the distance between the radiation output device 20 and the radiation detecting device 22 become equal to a distance depending on the SID, whereupon the touch sensor 52 outputs a detection signal to the radiation source controller 66 and the camera controller 86. The radiation source controller 66 controls the battery 68 in order to supply electric power to various components of the radiation output device 20, thereby activating the radiation output device 20. The radiation source controller 66 sends an activation signal, which indicates that the radiation output device 20 has been activated, via a wireless link to the control device 24.

The camera controller 86 controls the web camera 48 in order to start capturing a camera image of the imaging range 84. The web camera 48 starts to capture a camera image of the imaging range 84, which includes the region to be imaged of the subject 14 that has been positioned with respect to the imaging area 36 (step S3), and the web camera 48 acquires the camera image (step S4). The camera controller 86 sends the camera image of the imaging range 84, which has been captured by the web camera 48, via a wireless link to the control device 24.

In step S6, to be described later, since the database retriever 150 identifies the region to be imaged of the subject 14 using the camera image, the web camera 48 is capable of capturing at least one still image or moving image (camera image) before the main exposure mode. Since the radiation output device 20 is battery-powered, as described above, the camera controller 86 is capable of inactivating the web camera 48 immediately after the camera image has been captured, thereby reducing the electric power consumption of the radiation output device 20.

In the case that the control processor 124 of the control device 24 receives the activation signal via the antenna 120 and the communication unit 122, the control processor 124 sends a control signal for controlling the web camera 48 in order to start capturing a camera image via a wireless link to the radiation output device 20. Based on the control signal received via the antenna 62 and the communication unit 64, the camera controller 86 controls the web camera 48 in order to start capturing a camera image (step S3).

The control processor 124 of the control device 24 stores the camera image received via the antenna 120 and the communication unit 122 in the image memory 138, and displays the camera image on the display unit 126 (step S5). By viewing the camera image displayed on the display unit 126, the doctor 26 can confirm that the camera image has been obtained.

In step S6, the database retriever 150 automatically retrieves, from the database 134, object data that agree with the region to be imaged of the subject 14, which is included within the camera image. The database retriever 150 identifies for the main exposure mode a region to be imaged of the subject 14, which is represented by the object data that agree with the region to be imaged, as a region to be imaged of the subject 14.

Then, the database retriever 150 identifies the thickness of the region to be imaged of the subject 14 and the image capturing technique therefor. More specifically, if the region to be imaged of the subject 14, which is included in the order information stored in the order information storage unit 132, and the region to be imaged of the subject 14, which has been identified by the database retriever 150, are in agreement with each other, then the database retriever 150 identifies the thickness of the region to be imaged of the subject 14 and the image capturing technique therefor, which are included in the order information, as the thickness of the region to be imaged of the subject 14 and the image capturing technique therefor in the main exposure mode.

If the database retriever 150 retrieves, from the database 134, a plurality of object data, having a degree of coincidence with the region to be imaged in the camera image that has exceeded a predetermined threshold value, then the database retriever 150 displays the camera image and the plural object data on the display unit 126. The doctor 26 may confirm the camera image and the object data displayed on the display unit 126, and can operate the operating unit 128 in order to select the object data, which appear to be in agreement most closely with the region to be imaged in the camera image. The database retriever 150 then identifies the region to be imaged, which is represented by the selected object data, as a region to be imaged of the subject 14.

If, in step S6, the region to be imaged of the subject 14, which is included within the camera image, is not in agreement with the region to be imaged of the subject 14, which is included in the order information, or if a thickness of the region to be imaged of the subject 14 and an image capturing technique therefor are yet to be set, then the database retriever 150 may display on the display unit 126 the identified region to be imaged of the subject 14 and the order information. The doctor 26 can then confirm the identified region to be imaged of the subject 14 and the order information, which are displayed, and operate the operating unit 128 in order to enter a thickness of the region to be imaged of the subject 14, and an image capturing technique therefor. As a consequence, the database retriever 150 can identify the entered thickness of the region to be imaged of the subject 14 and the entered image capturing technique therefor, as the thickness of the region to be imaged of the subject 14 and the image capturing technique therefor in the main exposure mode. Further, the database retriever 150 can store the entered thickness of the region to be imaged of the subject 14 along with the entered image capturing technique therefor, as part of the order information in the order information storage unit 132, thereby editing the order information.

Figure 15:
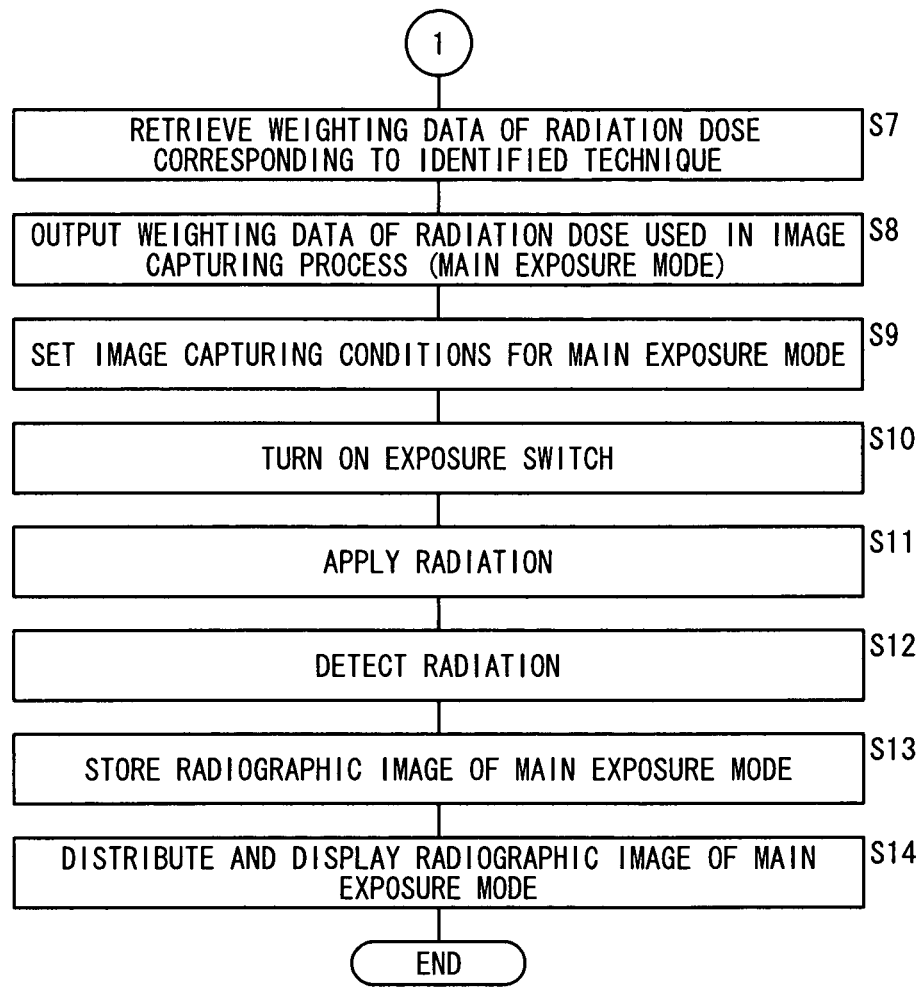
FIG. 15 is a flowchart of an operation sequence of the radiographic image capturing system shown in FIG. 1.

In step S7, as shown in FIG. 15, the database retriever 150 automatically retrieves, from the database 134, a region to be imaged of the subject 14, a thickness thereof, and an image capturing technique therefor, which correspond to the region to be imaged of the subject 14 that has been identified in step S6, the thickness thereof, and the image capturing technique therefor, along with optimum radiation dose data corresponding to such items of information. The database retriever 150 also automatically retrieves, from the database 134, weighting data corresponding to the region to be imaged of the subject 14 that has been identified in step S6, and the image capturing technique therefor. The database retriever 150 then outputs to the image capturing condition setting unit 152 the retrieved optimum radiation dose data and the retrieved weighting data, together with the order information including the region to be imaged of the subject 14, the thickness thereof, and the image capturing technique therefor, which have been used for retrieval, as various data necessary for the main exposure mode (step S8).

In step S8, if the database retriever 150 retrieves, from the database 134, a plurality of candidates for the optimum radiation dose data and the optimum weighting data, then the database retriever 150 displays the plural candidates and the order information on the display unit 126. The doctor 26 confirms the plural candidates and the order information displayed on the display unit 126, and operates the operating unit 128 in order to select a candidate (data) that appears to be most optimum for the main exposure mode. The database retriever 150 then outputs to the image capturing condition setting unit 152 the optimum radiation dose data and the optimum weighting data, which the doctor 26 has selected from among the plural candidates, and the order information, as various data necessary for the main exposure mode (step S8).

In steps S6 through S7, the database retriever 150 compares the region to be imaged of the subject 14, which is represented by the order information, and the region to be imaged of the subject 14, which is represented by the camera image, with each other. If the region to be imaged of the subject 14 is included within, but exceeds, the camera image, or if the region to be imaged of the subject 14 is not included within the camera image, then the database retriever 150 judges that the optimum radiation dose data and the optimum weighting data cannot properly be retrieved, and the above processes are not performed until a camera image including the region to be imaged of the subject 14 has been received.

In step S9, the image capturing condition setting unit 152 sets image capturing conditions (main exposure conditions) under which the region to be imaged of the subject 14 is to be irradiated with radiation 16a through 16c emitted from the radiation sources 18a through 18c, based on the entered optimum radiation dose data, the entered weighting data, and the order information.

If the region to be imaged of the subject 14 is a chest, as shown in FIG. 6B, then the image capturing condition setting unit 152 sets main exposure conditions (tube voltages, tube currents, and irradiation times) such that the doses of radiation 16a, 16c emitted from the radiation sources 18a, 18c at the ends are of a maximum dose level, and the dose of radiation 16b emitted from the radiation source 18b at the center is of a lower dose level, which is just enough to make up for any shortage of the maximum dose level, and stores the set main exposure conditions in the image capturing condition storage unit 136.

If the region to be imaged of the subject 14 is a hand (right hand), as shown in FIG. 7B, then the image capturing condition setting unit 152 sets main exposure conditions (tube voltages, tube currents, and irradiation times) such that the dose of radiation 16b emitted from the radiation source 18b at the center is of a maximum dose level, and the doses of radiation 16a, 16c emitted from the radiation sources 18a, 18c at the ends are of a lower dose level, which is just enough to make up for any shortage of the maximum dose level, and stores the set main exposure conditions in the image capturing condition storage unit 136.

The control processor 124 sends the set main exposure conditions to the radiation output device 20 and the radiation detecting device 22 wirelessly via the communication unit 122 and the antenna 120. The radiation source controller 66 of the radiation output device 20 registers the main exposure conditions received via the antenna 62 and the communication unit 64. The cassette controller 74 of the radiation detecting device 22 registers the main exposure conditions received via the antenna 70 and the communication unit 72.

In step S9, the image capturing condition setting unit 152 displays the entered optimum radiation dose data, the entered optimum weighting data, and the order information on the display unit 126. The doctor 26 may then confirm the optimum radiation dose data, the optimum weighting data, and the order information, which have been displayed, and operate the operating unit 128 in order to change details of the optimum radiation dose data and the optimum weighting data, depending on the order information, the state of the subject 14, or the image capturing technique. The image capturing condition setting unit 152 may be used to set desired main exposure conditions, based on the optimum radiation dose data and the optimum weighting data, which have been changed. In this case, the image capturing condition setting unit 152 stores the set main exposure conditions in the image capturing condition storage unit 136.

Provided that the above preparatory actions for the main exposure mode have been completed, the doctor 26 grips the grip 28 with one hand and turns on the exposure switch 130 with the other hand (step S10). The control signal generator 154 generates an exposure control signal for starting emission of radiation 16a through 16c from the radiation sources 18a through 18c, and sends the exposure control signal via a wireless link to the radiation output device 20 and the radiation detecting device 22. The exposure control signal is a synchronization control signal for capturing a main exposure image of the region to be imaged of the subject 14, as a result of synchronizing the start of emission of radiation 16a through 16c from the radiation sources 18a through 18c and the detection and conversion of such radiation 16a through 16c into a radiographic image by the radiation detector 60.

When the radiation source controller 66 receives the exposure control signal, the radiation source controller 66 controls the radiation sources 18a through 18c in order to apply prescribed doses of radiation 16a through 16c to the subject 14 according to the main exposure conditions. The radiation sources 18a through 18c respectively emit radiation 16a through 16c, which is output from the radiation output device 20 and applied to the region to be imaged of the subject 14, for a given exposure time (irradiation time) based on the main exposure conditions (step S11).

If the region to be imaged of the subject 14 is a chest region, as shown in FIGS. 4A and 6B, then the radiation sources 18a, 18c at the ends apply radiation 16a, 16c at the larger dose to the chest of the subject 14, whereas the radiation source 18b at the center applies radiation 16b at the smaller dose to the chest of the subject 14, which serves to make up for any shortage of the larger dose.

If the region to be imaged of the subject 14 is a right hand region, as shown in FIGS. 4B and 7B, then the radiation source 18b at the center applies radiation 16b at a larger dose to the right hand of the subject 14, whereas the radiation sources 18a, 18c at the ends apply radiation 16a, 16c at the smaller dose to the right hand of the subject 14, which serves to make up for any shortage of the larger dose.

In step S12, radiation 16a through 16c passes through the subject 14 and reaches the radiation detector 60 in the radiation detecting device 22. If the radiation detector 60 is of an indirect conversion type, then the scintillator of the radiation detector 60 emits visible light having an intensity depending on the intensity of the radiation 16a through 16c. The pixels 90 of the photoelectric conversion layer 96 convert the visible light into electric signals and store the electric signals as electric charges therein. The electric charges, which are stored in the pixels as representing a radiographic image (main exposure image) of the subject 14, are read by address signals, which are supplied from the address signal generator 78 of the cassette controller 74 to the line scanning driver 100 and the multiplexer 102.

More specifically, in response to the address signal supplied from the address signal generator 78, the address decoder 104 of the line scanning driver 100 outputs a selection signal to select one of the switches SW1, which supplies the control signal Von to the gates of the TFTs 98 connected to the gate line 92 that corresponds to the selected switch SW1. In response to the address signal supplied from the address signal generator 78, the address decoder 110 of the multiplexer 102 outputs a selection signal to successively turn on the switches SW2 to switch between the signal lines 94, for thereby reading through the signal lines 94 the electric charges stored in the pixels 90 connected to the selected gate line 92.

The electric charges read from the pixels 90 connected to the selected gate line 92 are amplified respectively by the amplifiers 106, sampled by the sample and hold circuits 108, and supplied to the multiplexer 102. Based on the supplied electric charges, the multiplexer 102 generates and supplies radiographic image signals to the A/D converter 112, which converts the radiographic image signals into digital signals. The digital signals, which represent the radiographic image information, are stored in the image memory 80 of the cassette controller 74 (step S13).

Similarly, the address decoder 104 of the line scanning driver 100 successively turns on the switches SW1 to switch between the gate lines 92, according to the address signal supplied from the address signal generator 78. The electric charges stored in the pixels 90 connected to the successively selected gate lines 92 are read through the signal lines 94, processed by the multiplexer 102, and converted into digital signals by the A/D converter 112. The digital signals are stored in the image memory 80 of the cassette controller 74 (step S13).

The radiographic image information (main exposure image), which is stored in the image memory 80, and the cassette ID information, which is stored in the cassette ID memory 82, are sent to the control device 24 wirelessly via the communication unit 72 and the antenna 70. The control processor 124 of the control device 24 stores the radiographic image information and the cassette ID information, which are received via the antenna 120 and the communication unit 122, in the image memory 138, and displays a main exposure image on the display unit 126 (step S14).

After having confirmed that the main exposure image has been obtained by visually checking the main exposure image displayed on the display unit 126, the doctor 26 releases the subject 14 from the position on the radiation detecting device 22, and removes the hand from the grip 28. The touch sensor 52 stops outputting the detection signal, and the radiation source controller 66 stops supplying electric power from the battery 68 to the various components of the radiation output device 20. As a result, the radiation output device 20 is brought into a sleep mode or is shut down. When the doctor 26 has turned off the switch 38, the battery 76 stops supplying electric power to the various components of the radiation detecting device 22, which is brought into a sleep mode or is shut down.

Then, the doctor 26 brings the connection terminals 39, 43 into interfitting engagement with each other, and also brings the connection terminals 41, 45 into interfitting engagement with each other, thereby holding the radiation output device 20 between the holders 35, 37 so as to integrally combine the radiation output device 20 and the radiation detecting device 22 with each other (see FIG. 2A).

[Advantages of the Present Embodiment]

As described above, with the radiographic image capturing system 10 and the radiographic image capturing method according to the present embodiment, the web camera 48 captures a camera image of the region to be imaged of the subject 14 that is disposed between the radiation detecting device 22 and the radiation output device 20, which houses at least two radiation sources (three radiation sources 18a through 18c in FIGS. 5A through 7B). Doses of radiation (radiation 16a through 16c) emitted from the at least two radiation sources for capturing a radiographic image (main exposure mode) are weighted based on the captured camera image.

According to the present embodiment, rather than simply establishing the irradiation range of radiation so as to cover the region to be imaged of the subject 14, the doses of radiation emitted from the radiation sources for capturing the main exposure image are weighted based on the camera image captured with the web camera 48 prior to carrying out the main exposure mode. Since the region to be imaged of the subject 14 is included within the camera image, the doses of radiation are weighted according to the region to be imaged of the subject 14.

According to the present embodiment, therefore, even if a radiographic image of the subject 14 is captured (main exposure mode) at a short SID using field-emission radiation sources, the irradiation range of radiation can easily be increased, and the subject 14 can be irradiated with an optimum dose of radiation. Since the subject 14 is irradiated with an optimum dose of radiation depending on the subject 14, it is possible to produce an appropriate radiographic image (main exposure image) for the doctor 26 to read, and to prevent the subject from suffering from undue radiation exposure.

The database retriever 150 identifies the region to be imaged of the subject 14, which is represented by the object data that agree with the region to be imaged of the subject 14 and which is included within the camera image, as a region to be imaged of the subject 14 for the main exposure mode. The database retriever 150 then retrieves optimum radiation dose data depending on the identified region to be imaged of the subject 14, the thickness thereof, and the image capturing technique therefor, retrieves weighting data depending on the region to be imaged of the subject 14 and the image capturing technique therefor, and thereafter outputs the retrieved optimum radiation dose data, the retrieved weighting data, and the order information to the image capturing condition setting unit 152. The image capturing condition setting unit 152 is thus capable of setting main exposure conditions accurately and efficiently.

As a result, as long as the radiation output device 20 applies radiation 16a through 16c from the respective radiation sources 18a through 18c to the region to be imaged of the subject 14 according to the main exposure conditions, a main exposure image of the region to be imaged of the subject 14 can be captured at a radiation dose that is optimum for the region to be imaged of the subject 14.

Only when the camera image, which has been captured by the web camera 48, is a camera image representing the region to be imaged of the subject 14, which is included within the Imaging range 84, the database retriever 150 retrieves weighting data, etc., corresponding to the region to be imaged of the subject 14 from the database 134. More specifically, if the database retriever 150 receives a camera image, wherein the region to be imaged of the subject 14 exceeds the imaging range 84 or the region to be imaged of the subject 14 is not included therein due to a reduced SID, the database retriever 150 does not carry out the above processes. Consequently, doses of radiation 16a through 16c can be weighted accurately.

The region to be imaged of the subject 14 is positioned centrally within the imaging area 36 (see FIGS. 4A and 4B), and the web camera 48, which is positioned near the central radiation source 18b that faces toward the center of the imaging area 36, captures a camera image of the imaging range 84, which includes the imaging area 36. Therefore, it is possible to reliably obtain a camera image that includes the region to be imaged of the subject 14.

The image capturing condition setting unit 152 may change details of the optimum radiation dose data and the weighting data retrieved by the database retriever 150, depending on the order information, the state of the subject 14, or the image capturing technique for the subject 14. Thus, more accurate main exposure conditions can be set depending on the actual image capturing technique for the subject 14.

Furthermore, if the control processor 124 acquires the order information, stores the order information in the order information storage unit 132, and then receives an activation signal from the radiation output device 20, then the control processor 124 sends a control signal to the radiation output device 20 for controlling the web camera 48 to start capturing a camera image, thereby allowing the control device 24 to control the web camera 48 to start capturing a camera image, and to reliably receive the camera image that is captured by the web camera 48.

According to the present embodiment, provided that the radiation output device 20 houses therein three radiation sources 18a through 18c, the doses of radiation 16a through 16c emitted from the respective radiation sources 18a through 18c are weighted as follows depending on the region to be imaged of the subject 14 for the main exposure mode.

As shown in FIG. 6B, if the main exposure mode is performed on a relatively large region to be imaged of the subject 14 (e.g., the chest of the subject 14), then the doses of radiation 16a through 16c emitted from the radiation sources 18a through 18c are weighted such that the doses of radiation 16a, 16c emitted from the radiation sources 18a, 18c at the ends are of a maximum dose level, whereas the dose of radiation 16b emitted from the radiation source 18b at the center is of a lower dose level.

As shown in FIG. 7B, if the main exposure mode is performed on a relatively small region to be imaged of the subject 14 (e.g., a hand of the subject 14), then the dose of radiation 16b emitted from the radiation source 18b at the center is of a maximum dose level, whereas the doses of radiation 16a, 16c emitted from the radiation sources 18a, 18c at the ends are of a lower dose level.

With the doses of radiation 16a through 16c weighted in the foregoing manner, even if a radiographic image of the subject 14 is captured at a short SID using field-emission radiation sources 18a through 18c, the irradiation range of the radiation 16a through 16c can easily be increased, and the subject 14 can be irradiated with an optimum dose of radiation 16a through 16c. Since the subject 14 is irradiated with an optimum dose of radiation depending on the subject 14, it is possible to produce an appropriate radiographic image (main exposure image) for the doctor 26 to read, and also prevent the subject from suffering from undue radiation exposure.

In the example shown in FIG. 6B, a radiographic image of a relatively large region to be imaged can be captured efficiently. In the example shown in FIG. 7B, a radiographic image of a relatively small region to be imaged can be captured efficiently.

The grip 28 is mounted on the side of the radiation output device 20, which is remote from the side where radiation 16a through 16c is emitted from the radiation sources 18a through 18c. Consequently, while holding the grip 28 with one hand, the doctor 26 can orient the radiation output device 20 toward the subject 14 and the radiation detecting device 22. Further, the doctor 26 can confirm images and data displayed on the display unit 126 (e.g., the camera image captured by the web camera 48), and operate the operating unit 128 or the exposure switch 130 with the other hand. In a case where radiation 16a through 16c is emitted from the radiation sources 18a through 18c while the doctor 26 grips the grip 28, the doctor 26 is reliably prevented from being irradiated with (exposed to) radiation 16a through 16c.

In the case that the doctor 26 brings the connection terminals 39, 43 and the connection terminals 41, 45 respectively into interfitting engagement with each other, thereby holding the radiation output device 20 between the holders 35, 37 and integrally combining the radiation output device 20 and the radiation detecting device 22 with each other, the doctor 26 can easily carry the radiation output device 20 and the radiation detecting device 22 together. At this time, since the connection terminals 39, 43 and the connection terminals 41, 45 are electrically connected respectively to each other, the battery 76 of the radiation detecting device 22 can charge the battery 68 of the radiation output device 20.

While the radiation output device 20 and the radiation detecting device 22 are integrally combined with each other, the radiation source controller 66 can inhibit the battery 68 from supplying electric power to the radiation sources 18a through 18c, for thereby preventing radiation 16a through 16c from being emitted while the radiation output device 20 and the radiation detecting device 22 are being carried. Since the side of the radiation output device 20 where radiation 16a through 16c is emitted from the radiation sources 18a through 18c faces toward the side of the housing 30 of the radiation detecting device 22 while the radiation output device 20 and the radiation detecting device 22 are integrally combined with each other, the doctor 26 is reliably prevented from being exposed to radiation 16a through 16c, even if such radiation 16a through 16c is emitted in error.

The control device 24 sends signals to and receives signals from the radiation output device 20 and the radiation detecting device 22 via a wireless link. Inasmuch as the radiation output device 20, the radiation detecting device 22, and the control device 24 are connected wirelessly via the same wireless link, and since no cables (USB cables) are required for signals to be sent and received therebetween, the doctor 26 can carry out work free from obstacles. Therefore, the doctor 26 can efficiently work on the radiographic image capturing system 10 in an obstacle-free environment. In addition, the radiographic image capturing system 10 is made up of a relatively small number of parts, since no cables are required for connection between the radiation output device 20, the radiation detecting device 22, and the control device 24. According to the present embodiment, signals may be sent and received via optical wireless communications using infrared rays or the like, rather than by means of conventional wireless communications.

According to the present embodiment, the control device 24 may also send signals to and receives signals from the radiation output device 20 and the radiation detecting device 22 via a wired link. For example, the radiation output device 20, the radiation detecting device 22, and the control device 24 may be electrically connected by USB cables (not shown), so that the power supply 140 of the control device 26 can charge the battery 68 of the radiation output device 20 and the battery 76 of the radiation detecting device 22. In addition, the control device 24 can reliably send an exposure control signal and image capturing conditions to the radiation output device 20 and the radiation detecting device 22, and the radiation detecting device 22 can reliably send radiographic images to the control device 24. Such a wired link enables signals to be sent and received reliably, and also allows the batteries 68, 76 to be charged reliably.

The batteries 68, 76 may be charged to a power level, which depends on at least the number of radiographic images to be captured of the subject 14. Consequently, the number of radiographic images to be captured of the subject 14 can reliably be captured during the radiographic image capturing process.

The batteries 68, 76 may be charged within a time zone in which the radiographic image capturing process is not being carried out. In this manner, the batteries 68, 76 are not charged during the radiographic image capturing process, and the captured radiographic images are transmitted after completion of the radiographic image capturing process. Accordingly, during the radiographic image capturing process, noise due to charging of the batteries 68, 76 is prevented from being added to the generated electric charges (analog signal), or from being added to radiographic images while the radiographic images are transmitted.

More specifically, the batteries 68, 76 may be charged within a time zone, except for a period (storage period) during which radiation 16a through 16c having passed through the subject 14 is converted into an electric signal by the radiation detector 60 and the electric signal is stored as electric charges in the pixels 90, a period (readout period) during which the electric charges stored in the pixels 90 are read, or a period (conversion period) during which the read electric charges (analog signals) are converted into digital signals by the A/C converter 112, or a period covering two or more of the storage, readout, and conversion periods, or a period covering all of the storage, readout, and conversion periods.

In the above three periods, i.e., in the storage, readout, and conversion periods, the image signal (radiographic image) is highly susceptible to noise. Particularly during the storage and readout periods, the electric charges generated by the pixels 90 are so small that they will be adversely affected by noise. During the conversion period, the analog signals representing the electric charges are less resistant to noise than digital signals, and any noise added to the analog signals tends to be converted into digital signals and appear in the image data.

The storage period includes a time during which the radiation sources 18a through 18c apply radiation 16a through 16c respectively to the subject 14. After the storage period has started, radiation 16a through 16c should start being applied as quickly as possible, and after radiation 16a through 16c has stopped being applied, the readout period should start immediately thereafter. Any time lag between these events should be minimized, so as to reduce dark current and to increase the quality of the generated radiographic image. The readout period is a period during which the TFTs 98 are turned on to supply signals through the amplifiers 106, etc., and to the A/D converter 112. Although the readout period and the conversion period occur substantially at the same time, the readout period actually starts slightly earlier than the conversion period.

Since the batteries 68, 76 are inhibited from being charged while a radiographic image of the subject 14 is being captured and transmitted, the radiation detector 60 can detect radiation 16a through 16c accurately.

The amount of electric power supplied to the batteries 68, 76 within a time zone during which the radiographic image capturing process is not carried out may be predicted as described below. The batteries 68, 76 may be charged with a predicted amount of electric power, in order to allow a required number of radiographic images to be captured reliably.

Amounts of electric power that are consumed by the radiation output device 20 and the radiation detecting device 22 are calculated from charging conditions for the batteries 68, 76, and from previous and present image capturing conditions (the numbers of captured radiographic images, mAs values, etc.). Amounts of electric power that are consumed by the radiation output device 20 and the radiation detecting device 22 in the present image capturing process, or amounts of electric power that are consumed by the radiation output device 20 and the radiation detecting device 22 in the previous image capturing process are predicted from the calculated amounts of electric power.

By charging the batteries 68, 76 to respective power levels, which are commensurate with amounts of electric power expected to be consumed during the present image capturing process, or with amounts of electric power consumed during the previous image capturing process, the present image capturing process can reliably be carried out.

If the batteries 68, 76 are to be charged during intervals between a plurality of radiographic image capturing events, then the amounts of electric power to be consumed by the radiation output device 20 and the radiation detecting device 22 are calculated from charging conditions and image capturing conditions (for radiographic images to be captured at the present time), from among the present image capturing conditions (numbers of captured radiographic images, mAs values, etc.), except for radiographic images that have already been captured, and amounts of electric power to be consumed for radiographic images to be captured at the present time are predicted based on the calculated image capturing conditions.

Since the batteries 68, 76 are charged to a power level commensurate with the amounts of electric power to be consumed for radiographic images to be captured at the present time, any remaining radiographic images to be captured can reliably be captured.

In the present embodiment, signals are sent and received by way of wireless communications and/or wired communications. However, if the subject 14 is held in contact with the radiation output device 20 and the radiation detecting device 22 at a short SID, then signals may be sent and received between the radiation output device 20 and the radiation detecting device 22 by way of human body communications via the subject 14. If the doctor 26 is held in contact with both the radiation output device 20 and the control device 24, then signals may be sent and received between the radiation output device 20 and the control device 24 by way of human body communications via the doctor 26.

In the present embodiment, the control signal generator 154 generates an exposure control signal for synchronizing emission of radiation 16a through 16c from the radiation sources 18a through 18c and conversion of such radiation 16a through 16c into a radiographic image (main exposure image) by the radiation detector 60, and the communication unit 122 sends the exposure control signal to the radiation output device 20 and the radiation detecting device 22. Therefore, the radiation sources 18a through 18c and the radiation detector 60 can reliably be synchronized with each other during the radiographic image capturing process (main exposure mode).

In the present embodiment, the radiation detecting device 22 includes the rectangular housing 30. However, the radiation detecting device 22 may be in the form of a flexible sheet including at least the radiation detector 60. Since such a flexible sheet is capable of being wound into a roll, the radiation detecting device 22 in the form of a flexible sheet can be made compact.

The present embodiment is applicable to acquisition of radiographic images using a light-reading-type radiation detector. Such a light-reading-type radiation detector operates as follows. When radiation is applied to a matrix of solid-state detecting devices, the solid-state detecting devices store an electrostatic latent image, which is dependent on the dose of applied radiation. For reading the stored electrostatic latent image, reading light is applied to the solid-state detecting devices in order to cause the solid-state detecting devices to generate an electric current representing radiation image information. When erasing light is applied to the radiation detector, radiographic image information representing a residual electrostatic latent image is erased from the radiation detector, whereby the radiation detector can be reused (see Japanese Laid-Open Patent Publication No. 2000-105297).

To prevent the radiographic image capturing system 10 from being contaminated with blood and bacteria, the radiation output device 20 and the radiation detecting device 22 may have a water-resistant and hermetically sealed structure, and may be sterilized and cleaned as necessary so that the radiographic image capturing system 10 can be used repeatedly.

The present embodiment is not limited to capturing of radiographic images in the art of medicine, but also may be applied to the capture of radiographic images in various non-destructive tests.

[Modifications of the Present Embodiment]

Modifications (first through tenth modifications) of the present embodiment will be described below with reference to FIGS. 16A through 29B. Further, while explanations are given with respect to these modifications, reference may also be made, as necessary, to FIGS. 1 through 15.

Those parts of the modifications, which are identical to those shown in FIGS. 1 through 15, are denoted by identical reference characters, and such features will not be described in detail below.

Figure 16A:
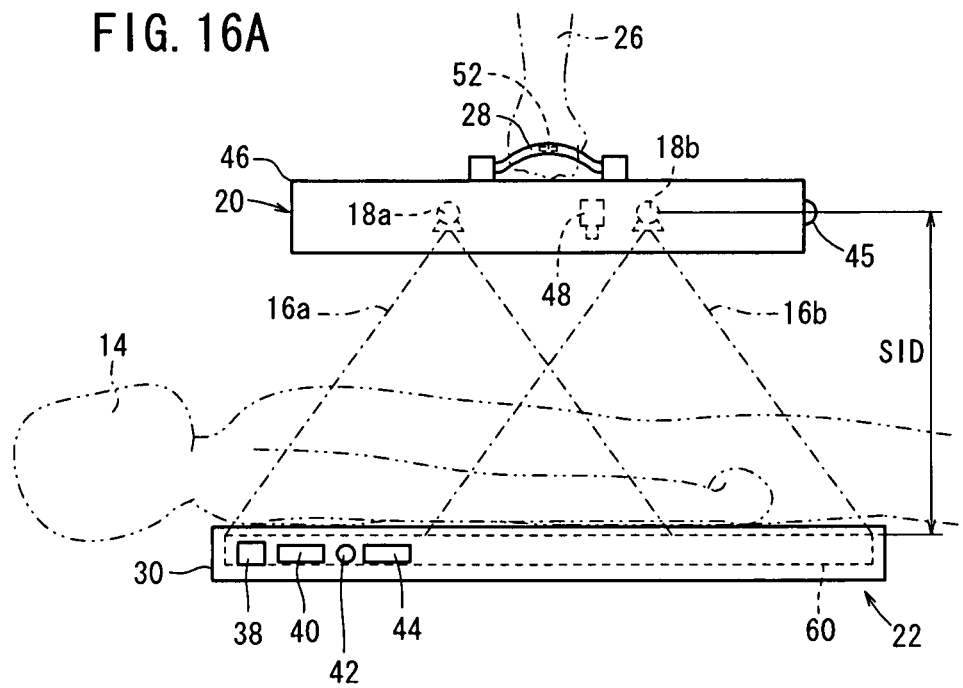
FIGS. 16A and 16B are side elevational views of a radiographic image capturing system according to a first modification.
Figure 16B:
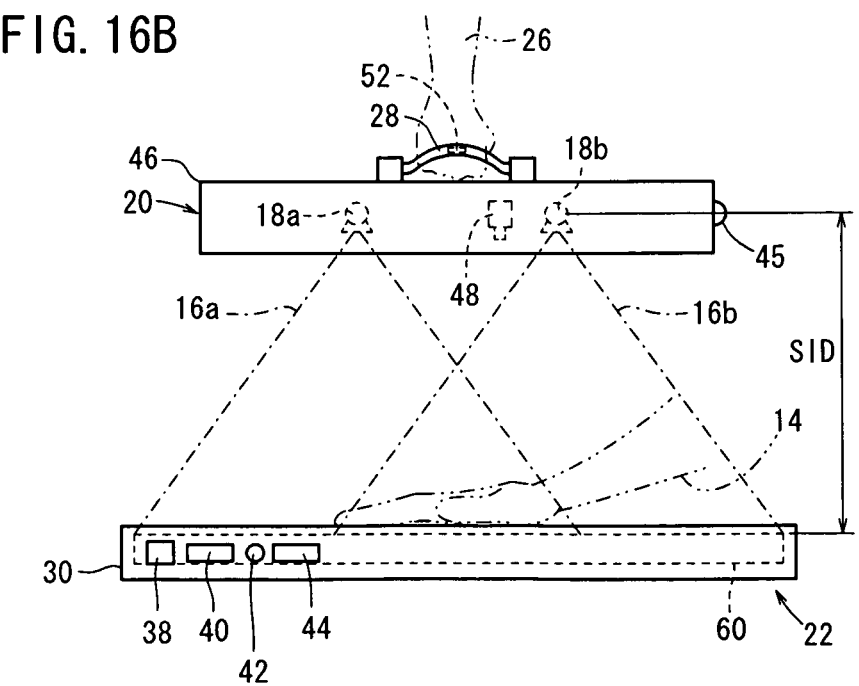

According to a first modification, as shown in FIGS. 16A and 16B, a radiation output device 20 houses two radiation sources 18a, 18b therein.

For capturing a radiographic image of a chest, as shown in FIG. 16A, and a radiographic image of a hand, as shown in FIG. 16B, the radiation sources 18a, 18b apply radiation 16a, 16b respectively to the subject 14. The doses of radiation 16a, 16b are weighted based on an optical camera image captured by a web camera 48, which also is housed in the radiation output device 20.

The first modification, in which two radiation sources 18a, 18b are housed in the radiation output device 20, offers the same advantages of those of the present embodiment.

According to the present embodiment and the first modification, doses of radiation emitted from two radiation sources 18a, 18b or three radiation sources 18a, 18b, 18c are weighted. However, doses of radiation emitted from four or more radiation sources may be weighted based on the principles of the present embodiment and the first modification, thereby offering the same advantages as those of the present embodiment and the first modification.

Figure 17A:
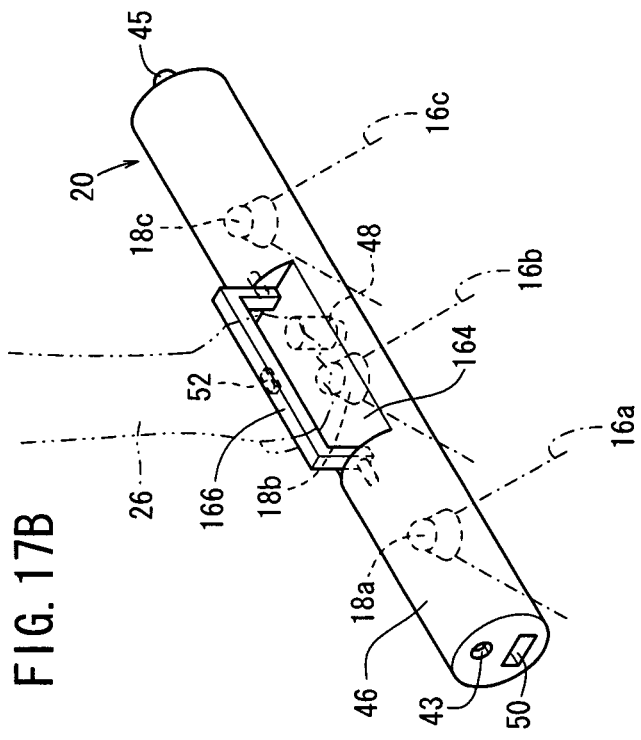
FIGS. 17A and 17B are perspective views of a radiographic image capturing system according to a second modification.
Figure 17B:
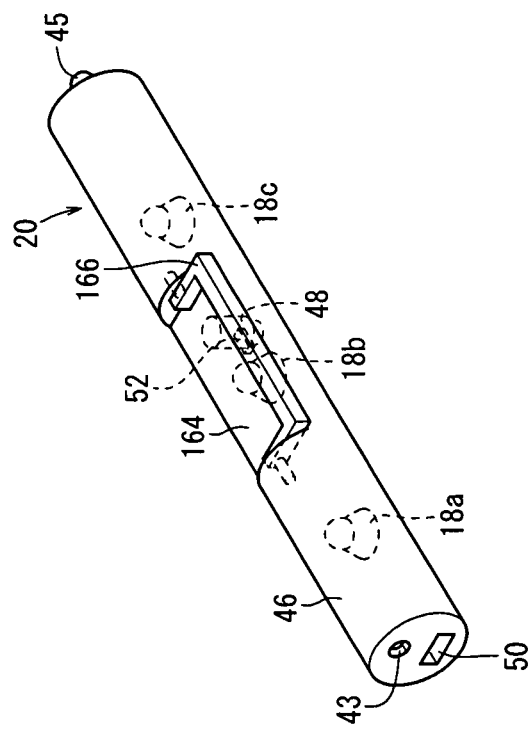
Figure 18:
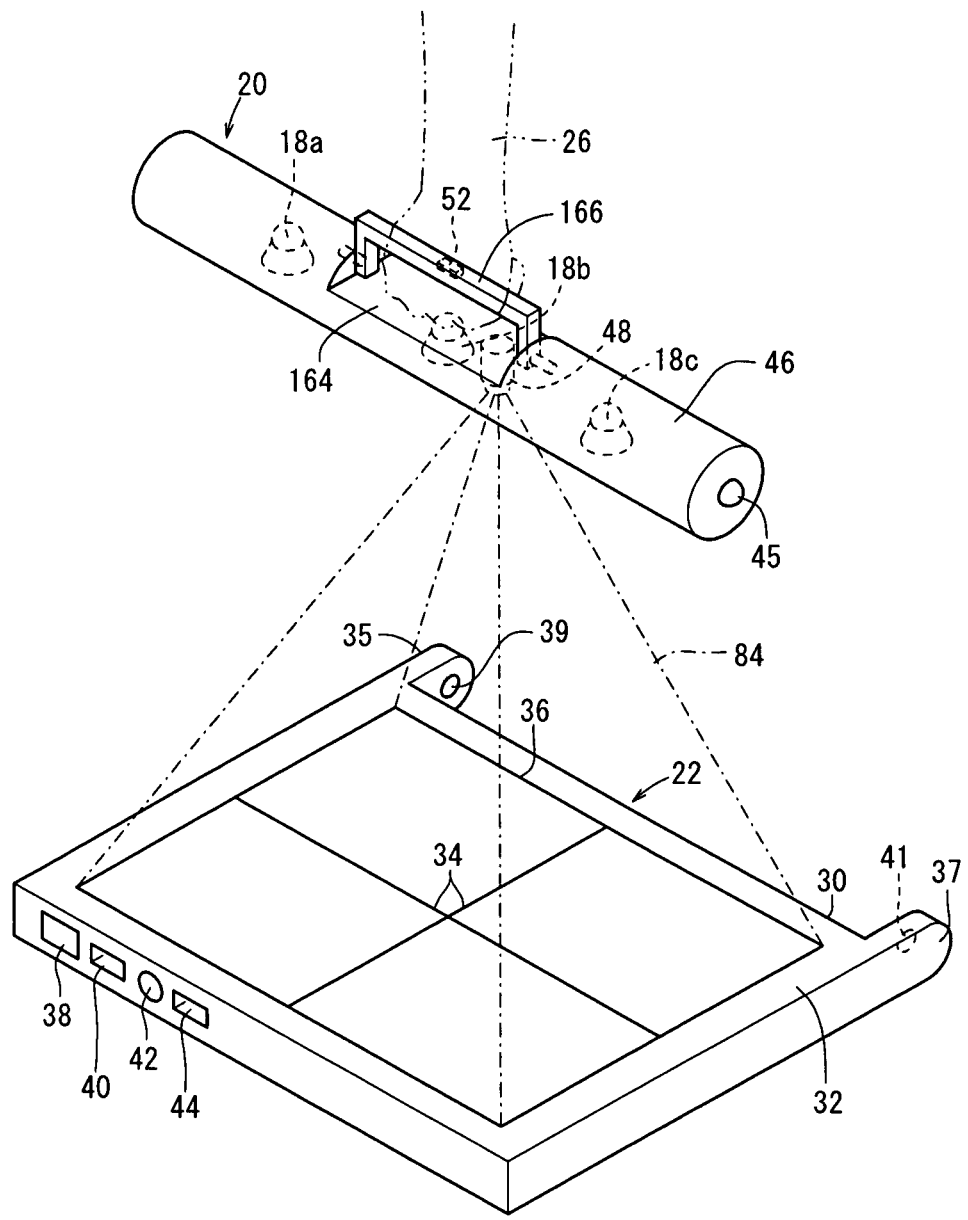
FIG. 18 is a perspective view of the radiographic image capturing system according to the second modification.

According to a second modification, as shown in FIG. 17A through 18, a casing 46 of the radiation output device 20 has a recess 164 defined in a side thereof remote from the side at which radiation 16a through 16c is emitted from the radiation sources 18a through 18c. A collapsible grip 166 is pivotally movably disposed in the recess 164. A touch sensor 52 is incorporated in the grip 166.

When the doctor 26 is not carrying the radiation output device 20, the grip 166 is accommodated flatwise in the recess 164, as shown in FIG. 17A. When the doctor 26 turns the grip 166 about the pivoted end, the grip 166 is raised out from the recess 164, so that the doctor 26 can grip the grip 166 (see FIGS. 17B and 18). The grip 166 and the touch sensor 52 offer the same advantages as those of the grip 28 and the touch sensor 52 according to the present embodiment. When the grip 166 is turned about the pivoted end back into the recess 164, the grip 166 is placed flatwise in the recess 164, thereby keeping the electrodes of the touch sensor 52 out of contact with the hand of the doctor 26. Therefore, the radiation output device 20 is prevented from being activated, and hence the radiation sources 18a through 18c are prevented from emitting radiation 16a through 16c in error.

Figure 19:
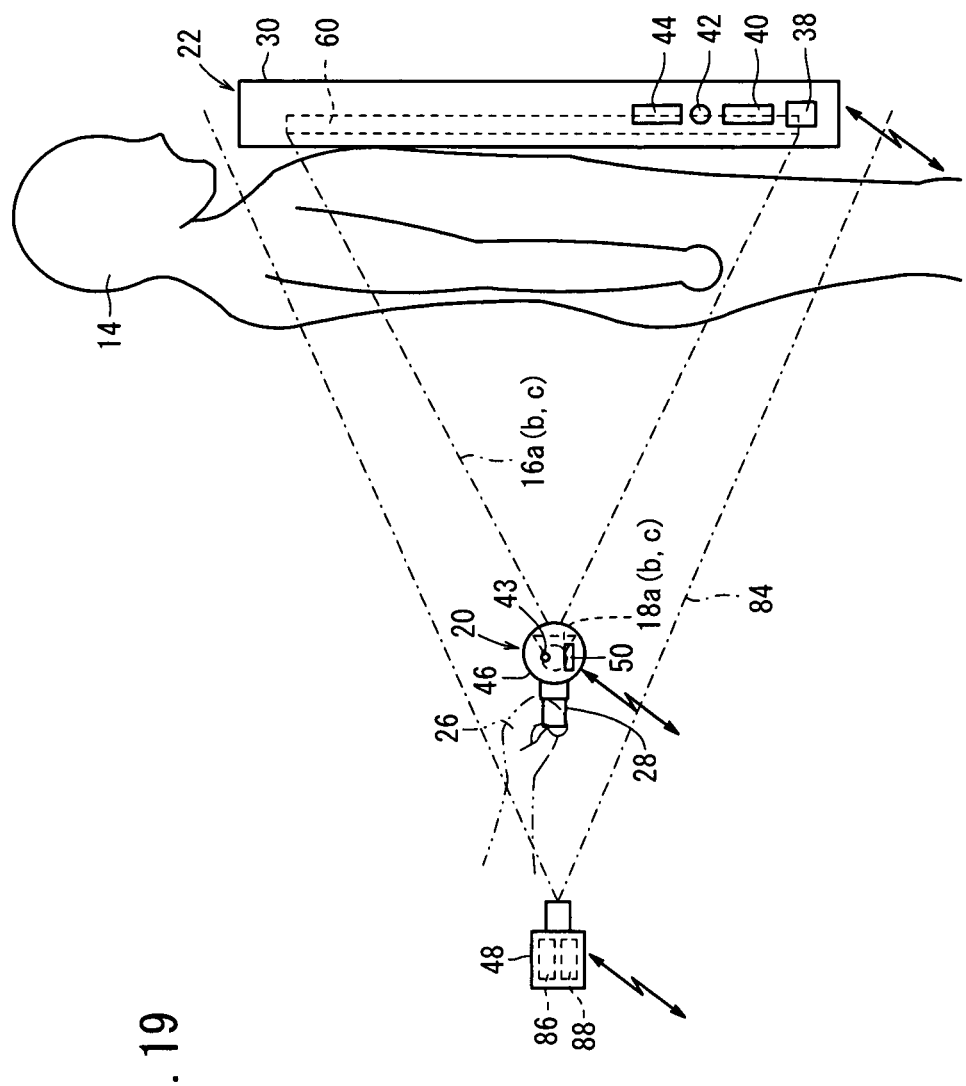
FIG. 19 is a side elevational view of a radiographic image capturing system according to a third modification.

According to a third modification, as shown in FIG. 19, the web camera 48 is separate from the radiation output device 20 and the radiation detecting device 22. The web camera 48 according to the third modification captures a camera image of the radiation output device 20, the region to be imaged of the subject 14, and the radiation detecting device 22. The web camera 48 includes a camera controller 86 and a communication unit 88 for sending signals to and receiving signals from an external circuit. When the control processor 124 of the control device 24 (see FIG. 9) receives an activation signal from the radiation output device 20, the control processor 124 sends a control signal to the communication unit 88 via a wireless link. The camera controller 86 controls the web camera 48 in order to start capturing the imaging range 84, based on the control signal received via the communication unit 88. According to the third modification, inasmuch as the radiation output device 20, the radiation detecting device 22, the control device 24, and the web camera 48 are connected wirelessly over the same wireless link, no cables are required in order for such devices to send and receive signals.

The third modification thus offers the same advantages as those of the present embodiment, the first modification, and the second modification.

Figure 20:
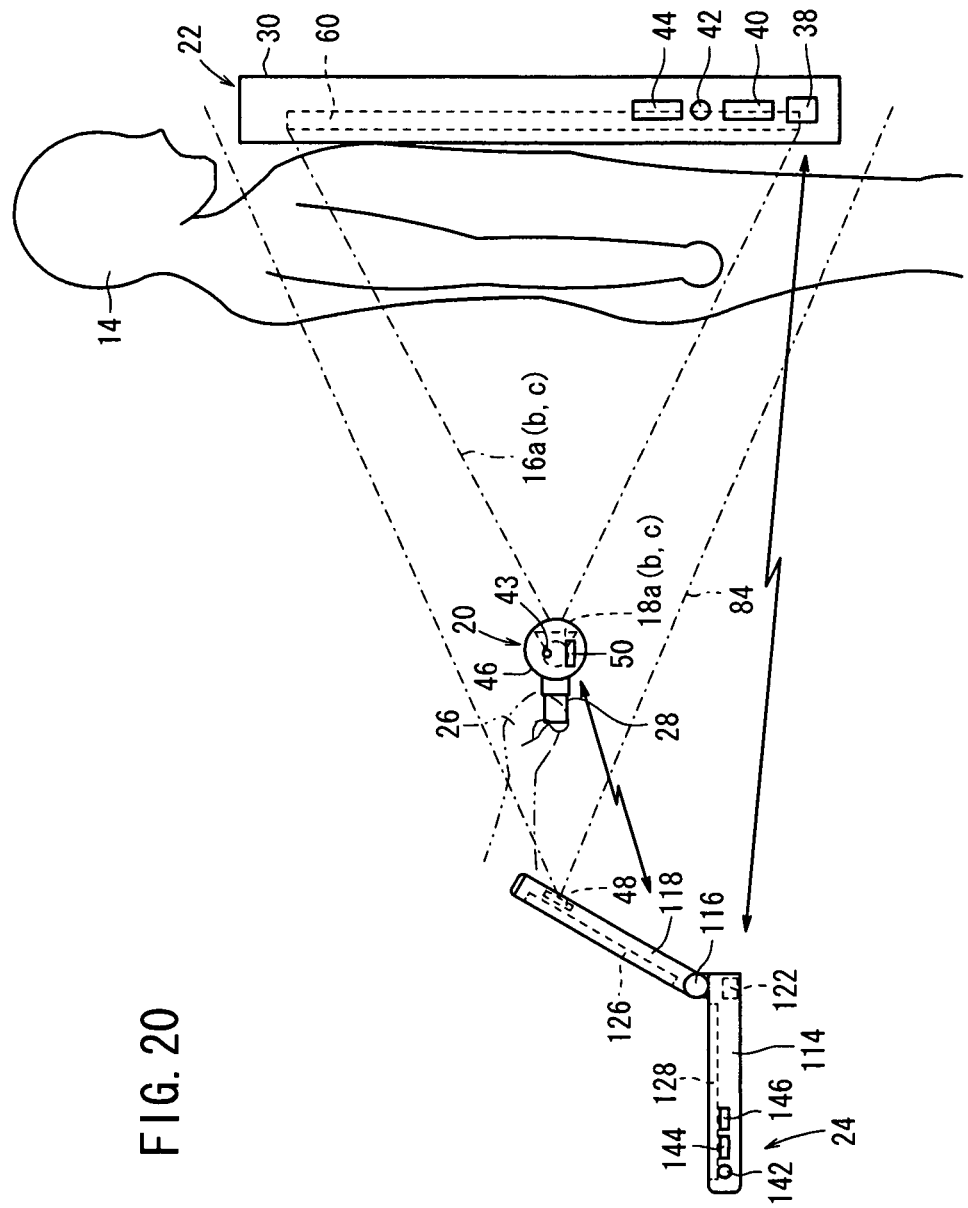
FIG. 20 is a side elevational view of a radiographic image capturing system according to a fourth modification.

According to a fourth modification, as shown in FIG. 20, the web camera 48 is incorporated in a control device 24 in the form of a portable terminal, so that the web camera 48 and the control device 24 are integrally combined with each other.

As shown in FIG. 20, the control device 24 comprises a laptop personal computer (PC) including a main body 114, which incorporates an operating unit 128 and a communication unit 122, a cover body 118 incorporating therein a display unit 126 and the web camera 48, and a hinge 116 interconnecting the main body 114 and the cover body 118. Therefore, the control device 24 and the web camera 48 are integrally combined with each other.

Integral combination of the control device 24 and the web camera 48 is not limited to an arrangement in which the web camera 48 is housed in the control device 24, but refers to any arrangement in which the web camera 48 is integrally joined (connected) to the control device 24, at least when the radiographic image capturing system 10 is in use. For example, integral combination of the control device 24 and the web camera 48 includes (1) an arrangement in which the web camera 48 and the control device 24 are connected to each other by a cable provided by the radiographic image capturing system 10, (2) an arrangement in which the web camera 48 and the control device 24 are connected to each other by a cable provided by the doctor 26, and (3) an arrangement in which the control device 24 and the web camera 48 are joined to each other when the radiographic image capturing system 10 is in use, and wherein the control device 24 and the web camera 48 can be disconnected (separated) from each other when the radiographic image capturing system 10 is undergoing maintenance or is not in use.

To make the web camera 48 disconnectable from the control device 24 when the radiographic image capturing system 10 is undergoing maintenance or is not in use, the web camera 48 may be joined to the control device 24 by a joining means such as a clip or the like. The web camera 48 may be joined to the control device 24 by such a joining means only when the radiographic image capturing system 10 is in use. The joining means may incorporate a ball joint for freely changing the orientation of the web camera 48 that is joined to the control device 24. If the web camera 48 is joined to the control device 24 by such a joining means, then it is necessary for the web camera 48 and the control device 24 to be electrically connected to each other by a wired link (e.g., a USB cable) or a wireless link.

If the control device 24 and the web camera 48 are connected to each other by a cable, then since the web camera 48 can independently be placed at a desired position within a range defined by the length of the cable, the web camera 48 can be positioned with greater freedom than if the web camera 48 were housed in the control device 24.

One side of the main body 114 has an input terminal 142 for connection to an AC adapter, a card slot 144 for receiving a memory card (not shown) therein, and a USB terminal 146 for connection to a USB cable (not shown).

In use, the cover body 118 is turned away from the main body 114 about the hinge 116 in order to orient the web camera 48 toward the radiation output device 20, the region to be imaged of the subject 14, and the radiation detecting device 22. When the control processor 124 (see FIG. 9) receives an activation signal from the radiation output device 20, the control processor 124 sends a control signal to the camera controller 86. Based on the control signal, the camera controller 86 controls the web camera 48 in order to start capturing a camera image of the imaging range 84.

The camera controller 86 then outputs the camera image captured by the web camera 48 to the control processor 124.

Since the web camera 48 is incorporated in the control device 24, the control device 24 can reliably acquire a camera image captured by the web camera 48. If the control processor 124 incorporates therein the function of the camera controller 86, then the control processor 124 can directly control the web camera 48. According to the fourth modification, inasmuch as the radiation output device 20, the radiation detecting device 22, and the control device 24 are connected wirelessly over the same wireless link, no cables are required for such devices to send and receive signals therebetween.

The fourth modification thus offers the same advantages as those of the present embodiment, as well as those of the first through third modifications.

Figure 21A:
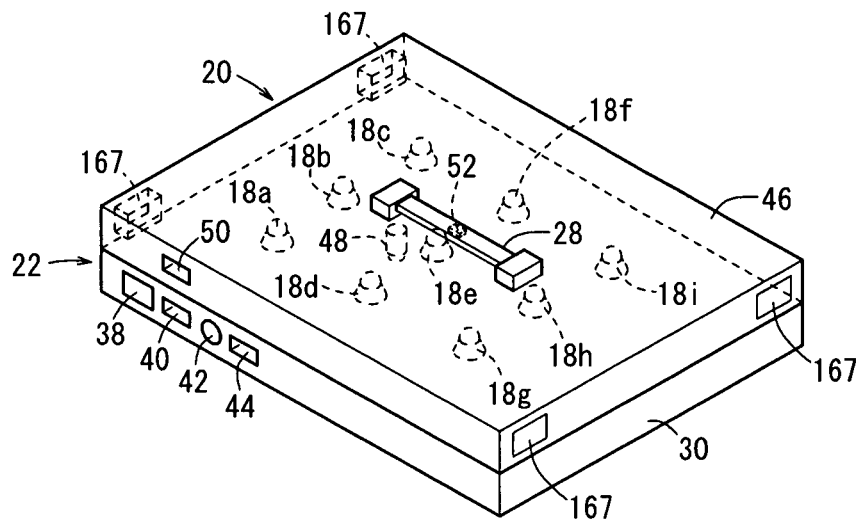
FIGS. 21A and 21B are perspective views of a radiographic image capturing system according to a fifth modification.
Figure 21B:
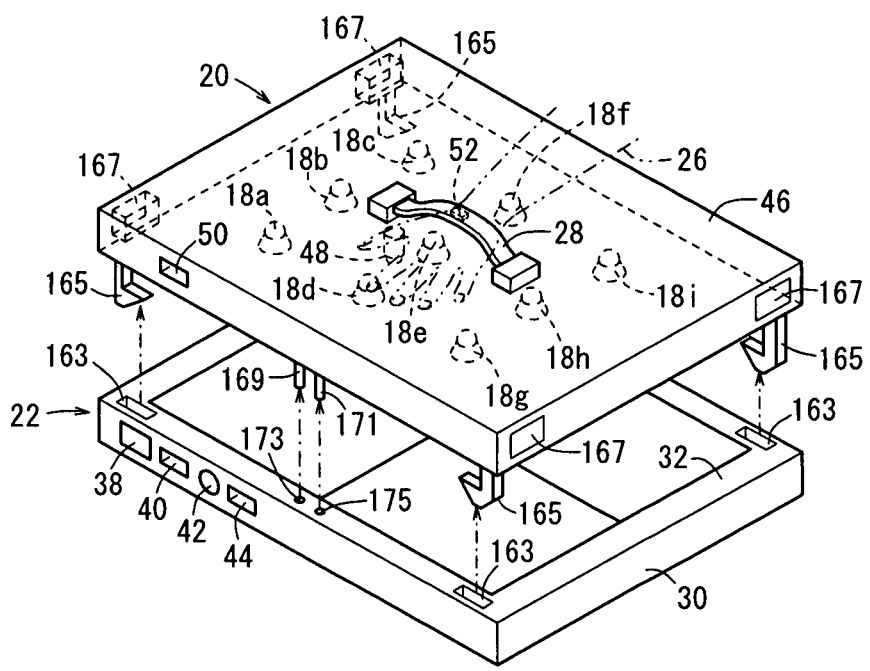

According to a fifth modification, as shown in FIGS. 21A and 21B, the casing 46 of the radiation output device 20 is of a rectangular shape, the planar area of which is substantially the same as the radiation detecting device 22. The casing 46 houses therein nine radiation sources 18a through 18i. The casing 46 is not required to house all of the nine radiation sources 18a through 18i, but may house at least three radiation sources.

The radiation sources 18a through 18i are arranged in a two-dimensional matrix facing toward the irradiated surface 32, which differs from the above-described linear array of radiation sources 18a through 18c that face toward the irradiated surface 32 (see FIGS. 1, 6A through 7B, and 16A, 16B).

The casing 46 has a grip 28 disposed on an upper surface, and also has unlocking buttons 167 on opposite side surfaces thereof for releasing hooks 165, which are mounted on the bottom surface of the casing 46, from openings 163 that are defined respectively in the four corners of the housing 30 of the radiation detecting device 22.

The housing 30 has connection terminals 173, 175 disposed on the upper surface thereof outside of the imaging area 36, which serve as jacks for interfitting engagement with respective pin-shaped connection terminals 169, 171 mounted on the bottom surface of the casing 46.

In FIG. 21A, the hooks 165 engage respectively in the openings 163, and the connection terminals 169, 171 are held in interfitting engagement with the respective connection terminals 173, 175, thereby holding the radiation output device 20 and the radiation detecting device 22 integrally with each other. The doctor 26 grips the grip 28, or inserts his or her hand between the grip 28 and the upper surface of the casing 46, in order to carry the radiation output device 20 and the radiation detecting device 22, which are integrally combined with each other. The battery 76 of the radiation detecting device 22 is capable of charging the battery 68 of the radiation output device 20 via the connection terminals 169, 171, 173, 175.

When the doctor 26 presses the unlocking buttons 167 in order to release the hooks 165 from the respective openings 163, and grips the grip 28 or inserts his or her hand between the grip 28 and the upper surface of the casing 46 so as to separate (lift) the radiation output device 20 from the radiation detecting device 22, the connection terminals 169, 171 are released from the connection terminals 173, 175, thereby separating the radiation output device 20 from the radiation detecting device 22. The battery 76 stops charging the battery 68, and the radiation sources 18a through 18i are made capable of emitting radiation respectively.

According to the fifth modification, since the radiation sources 18a through 18i are arranged in a two-dimensional matrix, radiographic images of any regions to be imaged of the subject 14 can be captured efficiently. As the casing 46 of the radiation output device 20 is essentially of the same rectangular shape as the housing 30 of the radiation detecting device 22, the radiation output device 20 and the radiation detecting device 22 that are integrally combined with each other are rendered highly portable, and the radiation output device 20 can easily be positioned with respect to the radiation detecting device 22.

The fifth modification thus offers the same advantages as those of the present embodiment, and the first through fourth modifications.

Figure 22:
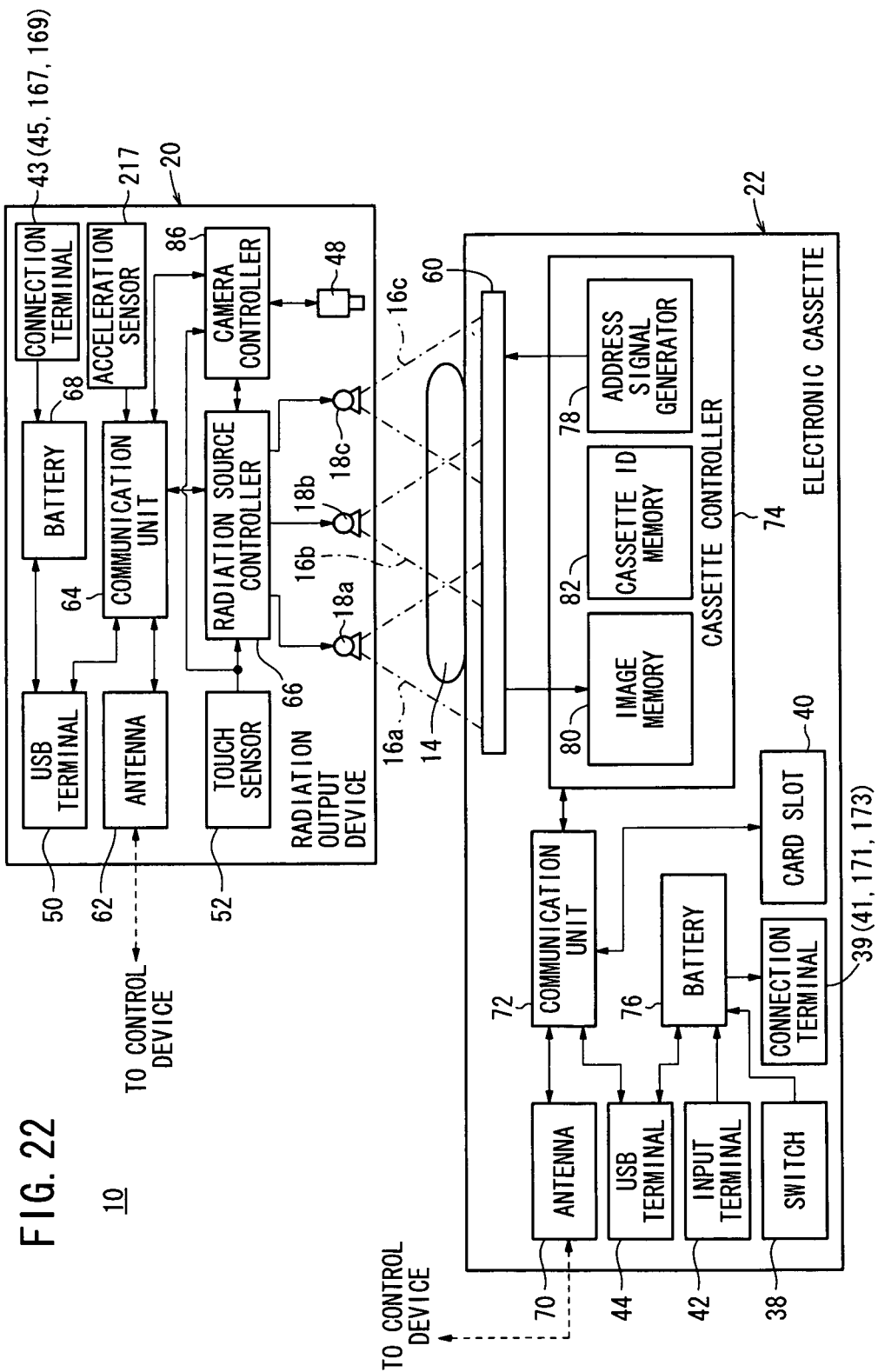
FIG. 22 is a block diagram of a radiographic image capturing system according to a sixth modification.
Figure 23:
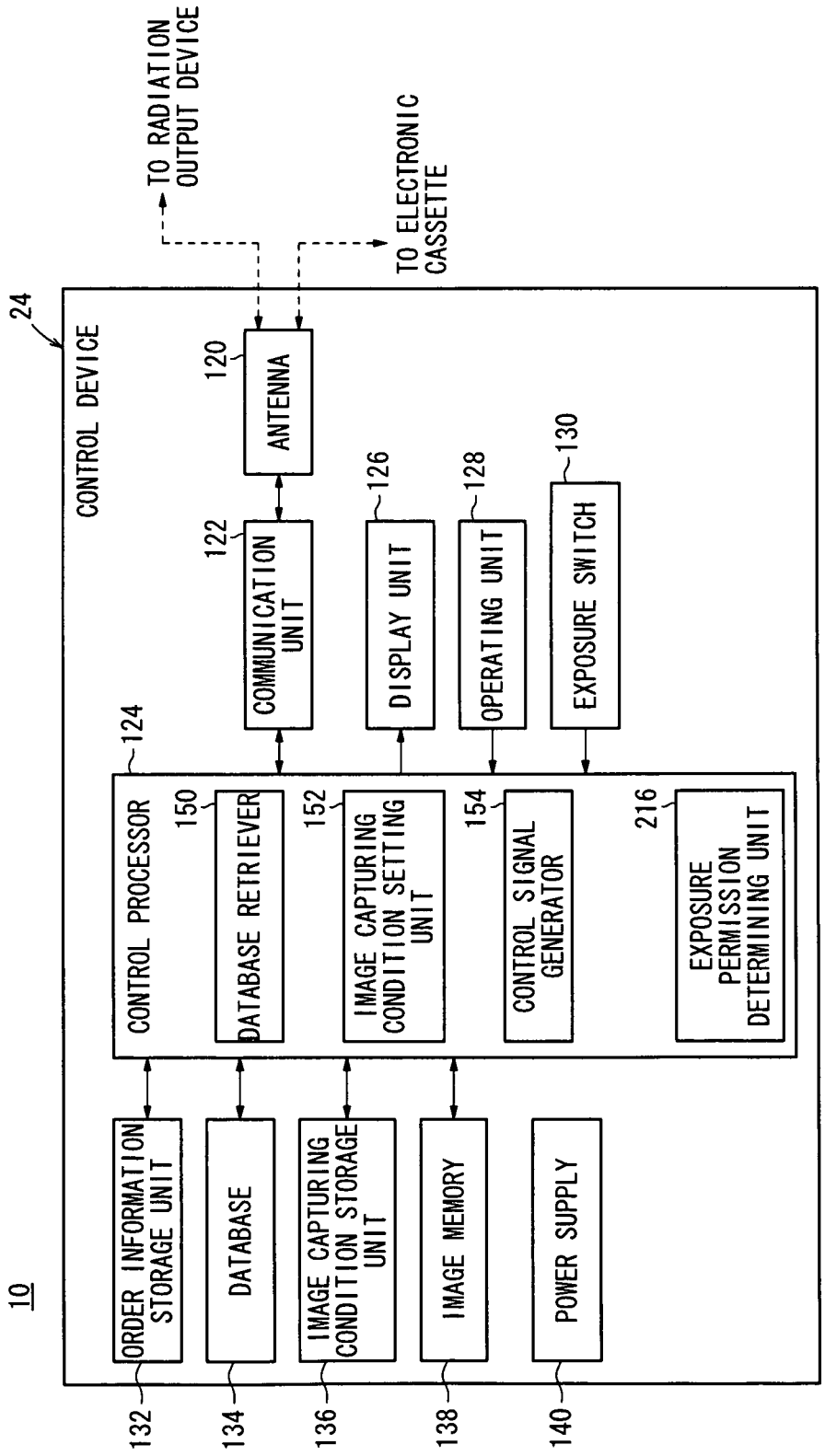
FIG. 23 is a block diagram of the radiographic image capturing system according to the sixth modification.

According to a sixth modification, as shown in FIGS. 22 and 23, a radiographic image capturing system 10 is different from the radiographic image capturing system 10 according to the present embodiment except that the radiation output device 20 additionally incorporates an acceleration sensor 217 therein, and the control processor 124 of the control device 24 further includes an exposure permission determining unit 216.

While the doctor 26 is holding the radiation output device 20 by gripping the grip 28, the acceleration sensor 217 sequentially detects the acceleration of the radiation output device 20 and sends a detection signal representative of the detected acceleration to the control device 24 wirelessly via the communication unit 64 and the antenna 62. The acceleration detected by the acceleration sensor 217 refers to a physical quantity representative of wobbling movement of the radiation output device 20 that is held by the doctor 26.

The exposure permission determining unit 216 determines whether capturing of a camera image and emission of radiation 16a through 16c from the radiation sources 18a through 18c (main exposure mode) are permitted or interrupted, based on the acceleration of the radiation output device 20, which is represented by the detection signal sent to the control device 24. If the exposure permission determining unit 216 judges that the acceleration represented by the detection signal received via the antenna 120 and the communication unit 122 has exceeded a prescribed threshold value, then the exposure permission determining unit 216 decides that capturing of a camera image and the main exposure mode should be interrupted, and indicates such interruption of capturing of the camera image and the main exposure mode to the doctor 26 via the display unit 126. The threshold value represents the magnitude of an acceleration, at a time when the radiation output device 20 wobbles to such an extent that a camera image cannot be captured accurately or the main exposure mode cannot be performed accurately.

The exposure permission determining unit 216 also is capable of calculating an amount of wobbling movement of the region to be imaged of the subject 14 in a camera image. If the exposure permission determining unit 216 judges that the calculated amount of wobbling movement of the region to be imaged of the subject 14 has exceeded a prescribed threshold value, then the exposure permission determining unit 216 reports (indicates) that the main exposure mode should be interrupted and that the camera image should be recaptured. The threshold value represents an amount of wobbling movement, which indicates that the region to be imaged of the subject 14 included within the camera image has wobbled to such an extent that the region to be imaged of the subject 14 cannot be identified, or to such an extent that the doses of radiation 16a through 16c cannot be weighted accurately. Wobbling movement of the region to be imaged of the subject 14 included within the camera image refers not only to wobbling movement of the region to be imaged of the subject 14 per se, but also may be caused by wobbling movement of the radiation output device 20 during capturing of the camera image.

Operations of the sixth modification will be described below with reference to the flowcharts shown in FIGS. 24 and 25.

Figure 24:
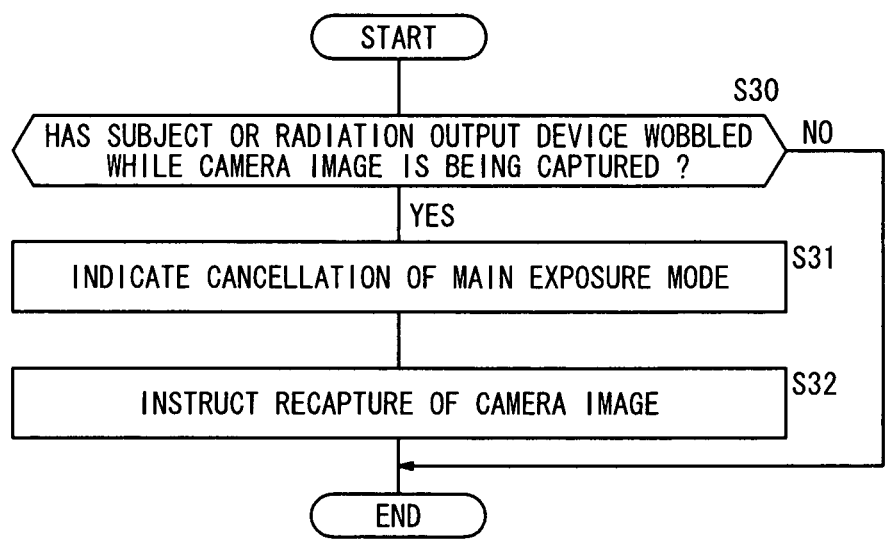
FIG. 24 is a flowchart of an operation sequence of the radiographic image capturing system according to the sixth modification.

FIG. 24 shows an operation sequence for the exposure permission determining unit 216, which carries out a procedure to judge that the main exposure mode should be interrupted and that a camera image should be recaptured, based on acceleration of the radiation output device 20 during capturing of a camera image, or based on an amount of wobbling movement of the region to be imaged of the subject 14, which is included within the camera image.

While a camera image is being captured, the acceleration sensor 217 sequentially detects the acceleration of the radiation output device 20, and sequentially sends a detection signal representing the detected acceleration to the control device 24 via a wireless link. The exposure permission determining unit 216 sequentially records data of the acceleration, which is represented by the received detection signal.

In step S30, after a camera image has been captured, the exposure permission determining unit 216 determines whether the recorded acceleration data includes acceleration data in excess of a prescribed threshold value or not. The exposure permission determining unit 216 also calculates an amount of wobbling movement of the region to be imaged of the subject 14 in the camera image, and determines whether or not the calculated amount of wobbling movement exceeds a prescribed threshold value.

If the exposure permission determining unit 216 finds acceleration data in excess of the threshold value, or if the exposure permission determining unit 216 judges that the calculated amount of wobbling movement of the region to be imaged of the subject 14 exceeds the prescribed threshold value (step S30: YES), then the exposure permission determining unit 216 judges that the radiation output device 20 has wobbled, or that the region to be imaged of the subject 14 has wobbled to such an extent that the camera image would be adversely affected during capturing of the camera image.

In step S31, the exposure permission determining unit 216 indicates cancellation of the main exposure mode to the doctor 26 via the display unit 126. The exposure permission determining unit 216 instructs the doctor 26 to recapture the camera image via the display unit 126 (step S32). By observing the information displayed on the display unit 126, the doctor 26 can recognize that a failure has occurred in capturing of the camera image, and the doctor undertakes preparatory actions for recapturing the camera image.

If the acceleration data recorded in the exposure permission determining unit 216 does not include acceleration data in excess of the threshold value, or if the calculated amount of wobbling movement of the region to be imaged of the subject 14 does not exceed the prescribed threshold value (step S30: NO), then the exposure permission determining unit 216 judges that the radiation output device 20 has not wobbled, or that the region to be imaged of the subject 14 has not wobbled to such an extent so as to adversely affect the camera image. As a result, the control device 24 can perform step S6 (see FIG. 14) and undertakes preparatory actions for the main exposure mode.

According to the operation sequence shown in FIG. 24, therefore, if the acceleration of the radiation output device 20 or wobbling movement of the region to be imaged of the subject 14 during capturing of a camera image is large enough to adversely affect the camera image, then the exposure permission determining unit 216 reports (indicates) that the main exposure mode should be interrupted and that the camera image should be recaptured. Consequently, a main exposure image can reliably be acquired.

Figure 25:
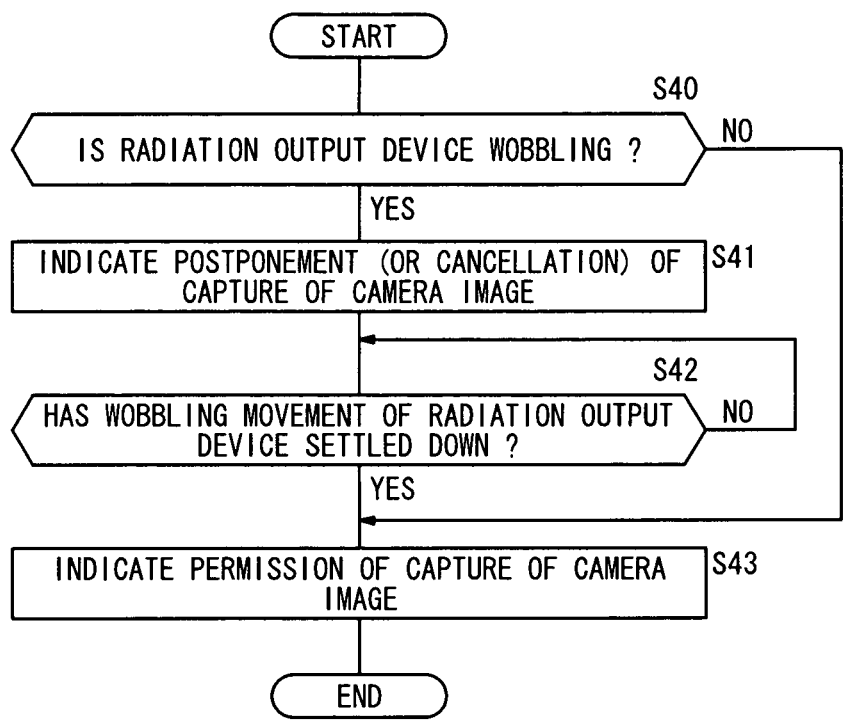
FIG. 25 is a flowchart of another operation sequence of the radiographic image capturing system according to the sixth modification.

FIG. 25 shows an operation sequence for the exposure permission determining unit 216 in order to postpone or cancel capturing of a camera image if the radiation output device 20 has already wobbled while a camera image is being captured or during preparatory actions that are taken to capture the camera image, and then to permit a camera image to be captured when such wobbling movements subsequently settle down.

While a camera image is being captured, or when preparatory actions are undertaken to capture a camera image, the acceleration sensor 217 sequentially detects the acceleration of the radiation output device 20, and sequentially sends a detection signal representing the detected acceleration to the control device 24 via a wireless link. In step S40, the exposure permission determining unit 216 determines whether or not the acceleration represented by the received detection signal exceeds a prescribed threshold value.

If the acceleration exceeds the threshold value, then the exposure permission determining unit 216 judges that the radiation output device 20 has wobbled to such an extent that the camera image will be adversely affected (step S40: YES), and decides to postpone or cancel capturing of the camera image.

In step S41, the exposure permission determining unit 216 indicates postponement or cancellation of capturing of the camera image to the doctor 26 via the display unit 126.

Even after step S42, the acceleration sensor 217 sequentially detects acceleration, and continues to send the detection signal representing the detected acceleration wirelessly to the control device 24.

In step S42, the exposure permission determining unit 216 determines whether or not the acceleration, which is represented by the received detection signal, has become smaller than the threshold value, i.e., whether or not wobbling movements of the radiation output device 20 held by the doctor 26 have settled down. If the acceleration becomes smaller than the threshold value, thus indicating that wobbling movements have settled down (step S42: YES), then the exposure permission determining unit 216 refrains from postponing or canceling capturing of the camera image, and displays a message indicating that capturing of a camera image is permitted on the display unit 126 (step S43). By seeing the message displayed on the display unit 126, the doctor 26 recognizes that capturing of a camera image is permitted, and the doctor 26 can perform step S3 or step S4 (see FIG. 14).

If the radiation output device 20 does not wobble in step S40, then since wobbling movements which could adversely affect the camera image do not occur, the exposure permission determining unit 216 judges that no problem will arise during capturing of the camera image (step S40: NO), and step S43 is carried out.

According to the operation sequence shown in FIG. 25, therefore, since a camera image can be acquired reliably, a main exposure image can also be acquired in a reliable manner.

In the above embodiment, the photoelectric conversion layer 96, which serves as one of the components of the radiation detector 60, is made of amorphous silicon (a-Si) or the like. According to the present invention, the photoelectric conversion layer may include an organic photoelectric conversion material.

A radiation detector including a photoelectric conversion layer, which includes an organic photoelectric conversion material according to a seventh modification, will be described below with reference to FIGS. 26 and 27.

Figure 26:
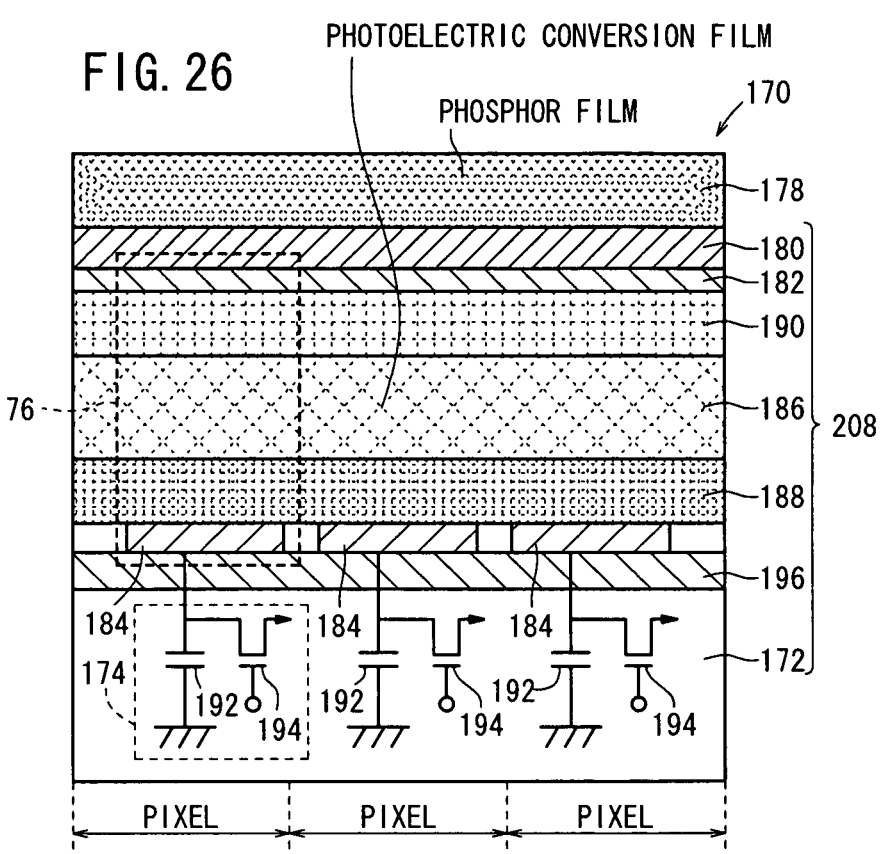
FIG. 26 is a cross-sectional view of a radiation detector according to a seventh modification.

As shown in FIG. 26, a radiation detector 170 according to the seventh modification includes a signal output section 174, a sensor 176, and a scintillator 178, which are successively deposited on an insulating substrate 172. The signal output section 174 and the sensor 176 jointly make up a pixel. The radiation detector 170 includes a matrix of pixels arrayed on the substrate 172. In each of the pixels, the signal output section 174 is superposed on the sensor 176.

Figure 27:
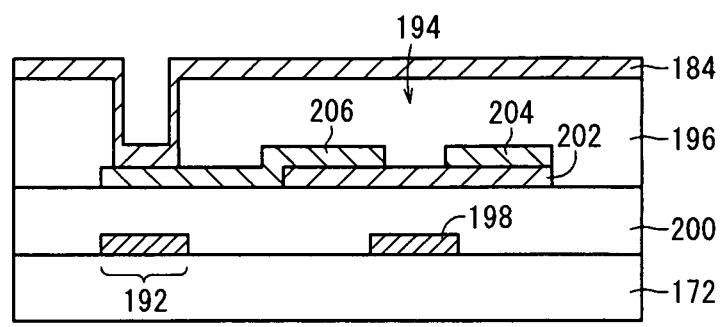
FIG. 27 is a cross-sectional view of a signal output per unit pixel of the radiation detector shown in FIG. 26.

More specifically, the radiation detector 170 shown in FIGS. 26 and 27 is a rear surface reading type, i.e., a penetration side sample (PSS) type, of radiation detector, in which the scintillator 178, the sensor 176 and the signal output section 174 are arranged in this order along the direction in which radiation 16a through 16c is applied. Explanations concerning a front surface reading type, i.e., an irradiation side sampling (ISS) type, of radiation detector, in which the signal output section 174, the sensor 176 and the scintillator 178 are arranged in this order along the direction in which radiation 16a through 16c is applied, shall be given below.

The scintillator 178 is disposed over the sensor 176 with a transparent insulating film 180 interposed therebetween. The scintillator 178 is in the form of a film made of phosphor, for emitting light converted from radiation 16a through 16c (see FIGS. 1 and 5B through 7B) that is applied from above, at a location remote from the substrate 172. The scintillator 178 can absorb radiation 16a through 16c that has passed through the subject 14 and emit light converted therefrom.

Light emitted by the scintillator 178 should preferably have a visible wavelength range from 360 nm to 830 nm. If the radiation detector 170 is used to capture a monochromatic image, then light emitted by the scintillator 178 should preferably include a green wavelength range.

If X-rays are used as the radiation 16a through 16c, then the phosphor used in the scintillator 178 should preferably include cesium iodide (CsI), and particularly preferably, should include CsI(Tl) (thallium-added cesium iodide) which, when irradiated with X-rays, emits light in a wavelength spectrum ranging from 420 nm to 700 nm. Light emitted from CsI(Tl) has a peak wavelength of 565 nm in the visible range. Further, such a phosphor is not limited to CsI (Tl), and other materials such as CsI(Na) (sodium-activated cesium iodide) or GOS ($Gd_2O_2S$:Tb) may also be used.

The sensor 176 includes an upper electrode 182, a lower electrode 184, and a photoelectric conversion film 186 disposed between the upper electrode 182 and the lower electrode 184. The photoelectric conversion film 186 is made of an organic photoelectric conversion material for generating electric charges by absorbing light emitted by the scintillator 178.

Since the light emitted by the scintillator 178 must be applied to the photoelectric conversion film 186, the upper electrode 182 should preferably be made of an electrically conductive material, which is transparent to at least the wavelength of the light emitted by the scintillator 178. More specifically, the upper electrode 182 should preferably be made of a transparent conducting oxide (TCO), which is of a high transmittance with respect to visible light and has a small resistance value. Although the upper electrode 182 may be made of a thin metal film such as of Au or the like, TCO is preferable thereto because Au tends to have an increased resistance value at transmittances of 90% or higher. For example, ITO (Indium Tin Oxide), IZO (Indium Zinc Oxide), AZO (Aluminum doped Zinc Oxide), FTO (Fluorine doped Tin Oxide), $SnO_2$, $TiO_2$, $ZnO_2$, or the like should preferably be used as the material of the upper electrode 182. Among these materials, ITO is the most preferable from the standpoints of process simplification, low resistance, and transparency. The upper electrode 182 may be a single electrode shared by all of the pixels, or may be a plurality of electrodes assigned to the respective pixels.

The photoelectric conversion film 186 may be made of a material that absorbs visible light and generates electrical charges, and may utilize the aforementioned amorphous silicon (a-Si) or an organic photoelectric conversion (OPC) material, which absorbs light emitted by the scintillator 178 and generates electric charges depending on the absorbed light.

In the case that the photoelectric conversion film 186 is constituted by amorphous silicon, a structure can be provided so as to absorb over a wide wavelength range visible light that is emitted from the scintillator 178. However, vapor deposition must be carried out in order to form the photoelectric conversion film 186 from amorphous silicon, and in the event that the substrate 172 is a synthetic resin, special consideration must be given to heat resistance of the substrate 172.

On the other hand, in the case that a photoelectric conversion film 186 including an organic photoelectric conversion material is used, the photoelectric conversion film 186 has a sharp absorption spectrum in the visible range and does not absorb electromagnetic waves other than light emitted by the scintillator 178. Therefore, any noise, which would be produced if radiation 16a through 16c such as X-rays were absorbed by the photoelectric conversion film 186, is effectively minimized.

Further, since a photoelectric conversion film 186 made from an organic photoelectric conversion material can be formed using a liquid droplet discharge head such as an inkjet head or the like, in which the organic photoelectric conversion material is made to adhere to a formed body, the formed body is not necessarily resistant to heat.

In order for the organic photoelectric conversion material of the photoelectric conversion film 186 to absorb light emitted by the scintillator 178 most efficiently, the absorption peak wavelength thereof should preferably be as close as possible to the light emission peak wavelength of the scintillator 178. Although the absorption peak wavelength of the organic photoelectric conversion material and the light emission peak wavelength of the scintillator 178 should ideally be in agreement with each other, it is possible to sufficiently absorb light emitted by the scintillator 178 if the difference between the absorption peak wavelength and the light emission peak wavelength is sufficiently small. More specifically, the difference between the absorption peak wavelength of the organic photoelectric conversion material and the light emission peak wavelength of the scintillator 178 with respect to the radiation 16a through 16c should preferably be 10 nm or smaller, and more preferably, 5 nm or smaller.

Organic photoelectric conversion materials that meet the above requirements include quinacridone-based organic compounds and phthalocyanine-based organic compounds. Since quinacridone has an absorption peak wavelength of 560 nm in the visible range, if quinacridone is used as the organic photoelectric conversion material and CsI(Tl) as the material of the scintillator 178, the difference between the above peak wavelengths can be reduced to 5 nm or smaller, thus making it possible to substantially maximize the amount of electric charges generated by the photoelectric conversion film 186.

The photoelectric conversion film 186, which is applicable to the radiation detector 170, will be described in specific detail below.

The radiation detector 170 includes an electromagnetic wave absorption/photoelectric conversion region, which is provided by an organic layer including the electrodes 182, 184 and the photoelectric conversion film 186 sandwiched between the electrodes 182, 184. The organic layer may be formed by the superposition or mixture of an electromagnetic wave absorption region, a photoelectric conversion region, an electron transport region, a hole transport region, an electron blocking region, a hole blocking region, a crystallization preventing region, an electrode, and an interlayer contact improving region, etc.

The organic layer should preferably include an organic p-type compound or an organic n-type compound.

An organic p-type semiconductor (compound) is a donor organic compound mainly typified by a hole transport organic compound, and refers to an organic compound that tends to donate electrons. More specifically, when two organic materials are used in contact with each other, one of the organic materials, which has a lower ionization potential, is referred to as a donor organic compound. Any organic compounds that are capable of donating electrons can be used as the donor organic compound.

An organic n-type semiconductor (compound) is an acceptor organic compound mainly typified by an electron transport organic compound, and refers to an organic compound that tends to accept electrons. More specifically, when two organic materials are used in contact with each other, one of the organic materials, which has a larger electron affinity, is referred to as an acceptor organic compound. Any organic compounds that are capable of accepting electrons can be used as the acceptor organic compound.

Materials that can be used as the organic p-type semiconductor and the organic n-type semiconductor, and arrangements of the photoelectric conversion film 186 are disclosed in detail in Japanese Laid-Open Patent Publication No. 2009-032854, and such features will not be described in detail below.

The sensor 176 of each pixel may include at least the lower electrode 184, the photoelectric conversion film 186, and the upper electrode 182. For preventing an increase in dark current, the sensor 176 should preferably additionally include either an electron blocking film 188 or a hole blocking film 190, and more preferably, should include both the electron blocking film 188 and the hole blocking film 190.

The electron blocking film 188 may be disposed between the lower electrode 184 and the photoelectric conversion film 186. When a bias voltage is applied between the lower electrode 184 and the upper electrode 182, the electron blocking film 188 is capable of preventing electrons from being injected from the lower electrode 184 into the photoelectric conversion film 186, thereby preventing dark current from increasing.

The electron blocking film 188 may be made of an organic material capable of donating electrons.

The electron blocking film 188 is actually made of a material that is selected depending on the material of the lower electrode 184 and the material of the photoelectric conversion film 186, which lie adjacent thereto. Preferably, the material should have an electron affinity (Ea) that is at least 1.3 eV greater than the work function (Wf) of the material of the adjacent lower electrode 184, and an ionization potential (Ip) that is equal to or smaller than the Ip of the material of the adjacent photoelectric conversion film 186. Materials that can be used as an organic material, and which are capable of donating electrons, are disclosed in detail in Japanese Laid-Open Patent Publication No. 2009-032854, and such materials will not be described in detail below.

The thickness of the electron blocking film 188 should preferably be in a range from 10 nm to 200 nm, more preferably in a range from 30 nm to 150 nm, and particularly preferably in a range from 50 nm to 100 nm, in order to reliably achieve a dark current reducing capability, and to prevent the photoelectric conversion efficiency of the sensor 176 from being lowered.

The hole blocking film 190 may be disposed between the photoelectric conversion film 186 and the upper electrode 182. When a bias voltage is applied between the lower electrode 184 and the upper electrode 182, the hole blocking film 190 is capable of preventing holes from being injected from the upper electrode 182 into the photoelectric conversion film 186, thereby preventing dark current from increasing.

The hole blocking film 190 may be made of an organic material, which is capable of accepting electrons.

The thickness of the hole blocking film 190 should preferably be in a range from 10 nm to 200 nm, more preferably in a range from 30 nm to 150 nm, and particularly preferably in a range from 50 nm to 100 nm, in order to reliably achieve a dark current reducing capability, and to prevent the photoelectric conversion efficiency of the sensor 176 from being lowered.

The hole blocking film 190 is actually made of a material that is selected depending on the material of the upper electrode 182 and the material of the photoelectric conversion film 186 that lie adjacent thereto. A preferable material should have an ionization potential (Ip) that is at least 1.3 eV greater than the work function (Wf) of the material of the adjacent upper electrode 182, and an electron affinity (Ea) equal to or greater than the Ea of the material of the adjacent photoelectric conversion film 186. Materials that can be used as organic materials capable of accepting electrons are disclosed in detail in Japanese Laid-Open Patent Publication No. 2009-032854, and such materials will not be described in detail below.

In order to set a bias voltage to move holes, from among the electric charges generated in the photoelectric conversion film 186, toward the upper electrode 182, and to move electrons, from among the electric charges generated in the photoelectric conversion film 186, toward the lower electrode 184, the electron blocking film 188 and the hole blocking film 190 may be switched in position. The electron blocking film 188 and the hole blocking film 190 are not both required, but rather, either one of the electron blocking film 188 and the hole blocking film 190 may be included so as to provide a certain dark current reducing capability.

The signal output section 174 is disposed on the surface of the substrate 172 beneath the lower electrode 184 of each pixel.

FIG. 27 schematically shows structural details of the signal output section 174.

As shown in FIG. 27, the signal output section 174 includes a capacitor 192, which is aligned with the lower electrode 184, for storing electric charges that have moved to the lower electrode 184, and a field-effect thin film transistor (hereinafter also referred to simply as a "thin film transistor" or TFT) 194 for converting the electric charges stored in the capacitor 192 into electric signals, and outputting the electric signals. The capacitor 192 and the thin film transistor 194 are disposed in a region underlapping the lower electrode 184 as viewed in plan. This structure enables the signal output section 174 and the sensor 176 to be superposed in each pixel in the thickness direction. In order to minimize the planar area of the radiation detector 170 (pixels), it is desirable for the region in which the capacitor 192 and the thin film transistor 194 are disposed to be fully covered with the lower electrode 184.

The capacitor 192 is electrically connected to the lower electrode 184 by an electrically conductive interconnection, which extends through an insulating film 196 interposed between the substrate 172 and the lower electrode 184. The interconnection allows electric charges collected by the lower electrode 184 to migrate toward the capacitor 192.

As shown in FIG. 27, the thin film transistor 194 includes a stacked assembly made up of a gate electrode 198, a gate insulating film 200, and an active layer (channel layer) 202, and a source electrode 204 and a drain electrode 206 disposed on the active layer 202 and spaced from each other with a gap therebetween. In the radiation detector 170, although the active layer 202 may be formed by any of amorphous silicon, an amorphous oxide, an organic semiconductor material, carbon nanotubes or the like, materials capable of forming the active layers are not limited to the foregoing materials.

As an amorphous oxide that constitutes the active layer 202, such an amorphous oxide should preferably be an oxide (e.g., In—O oxide) including at least one of In, Ga, and Zn, more preferably, an oxide (e.g., In—Zn—O oxide, In—Ga—O oxide, or Ga—Zn—O oxide) including at least two of In, Ga, and Zn, and particularly preferably, an oxide including In, Ga, and Zn. An In—Ga—An—O amorphous oxide should preferably be an amorphous oxide, the crystalline composition of which is represented by $InGaO_3 (ZnO)_m$ where m represents a natural number smaller than 6, and more particularly, preferably should be $InGaZnO_4$. However, amorphous oxides capable of forming the active layer 202 are not limited to the foregoing.

Further, as organic semiconductor materials capable of forming the active layer 202, for example, there may be used phthalocyanine compounds, pentacene, vanadyl phthalocyanine or the like, although the present invention is not limited to such materials. Concerning phthalocyanine compounds, details thereof are described in detail in Japanese Laid-Open Patent Publication No. 2009-212389, and detailed explanations of such compounds are omitted.

If the active layer 202 of the thin film transistor 194 is made from any of an amorphous oxide, an organic semiconductor material, carbon nanotubes or the like, then since the active layer 202 does not absorb radiation 16a through 16c such as X-rays or the like, or absorbs only an extremely small amount of radiation 16a through 16c, the active layer 202 is effective to reduce noise generated in the signal output section 174.

Further, if the active layer 202 is formed from carbon nanotubes, the switching speed of the thin film transistor 194 can be increased, and absorption of light in the visible light band in the thin film transistor 194 can be lessened. Moreover, if the active layer 202 is formed from carbon nanotubes, because performance of the thin film transistor 194 is lowered remarkably as a result of being mixed with only extremely small amounts of metallic impurities, it is necessary to form the active layer 202 by separating and extracting carbon nanotubes, which are extremely high in purity, by means of centrifugal separation or the like.

Further, because films formed from organic photoelectric conversion materials and films formed from organic semiconductor materials possess sufficient flexibility, if a structure is constituted by a combination of a photoelectric conversion film 186 formed from an organic photoelectric conversion material and a thin film transistor 194 in which the active layer 202 thereof is formed from an organic semiconductor material, it becomes unnecessary for a TFT substrate 208 to have high rigidity to accommodate as a load the weight of the body of the subject 14.

The amorphous oxide of the active layer 202 of the thin film transistor 194, and the organic photoelectric conversion material of the photoelectric conversion film 186 can be deposited as films at low temperatures. Therefore, the substrate 172 is not limited to a highly heat-resistant substrate, such as a semiconductor substrate, a quartz substrate, a glass substrate, or the like, but may be a flexible substrate made of plastic, a substrate of aramid fibers, or a substrate of bionanofibers.

More specifically, the substrate 172 may be a flexible substrate of polyester, such as polyethylene terephthalate, polybutylene phthalate, polyethylene naphthalate, or the like, polystyrene, polycarbonate, polyethersulfone, polyarylate, polyimide, polycycloolefine, norbornene resin, poly(chlorotrifluoro-ethylene), or the like. A flexible substrate fabricated from plastic makes the radiation detector 170 light in weight and hence easier to carry.

The substrate 172 may include an insulating layer for thereby making the substrate 172 electrically insulative, a gas barrier layer for making the substrate 172 impermeable to water and oxygen, and an undercoat layer for making the substrate 172 flat and improving intimate contact between the substrate 172 and the electrode.

Aramid fibers for use as the substrate 172 are advantageous in that, since a high-temperature process at 200° C. is applicable thereto, aramid fibers allow a transparent electrode material to be set at a high temperature for lower resistance, and also allow driver ICs to be automatically mounted thereon by a process including a solder reflow process. Furthermore, since aramid fibers have a coefficient of thermal expansion that is close to ITO (Indium Tin Oxide) and glass, an insulating substrate made of aramid fibers is less likely to suffer from warpage and cracking after fabrication thereof. In addition, an insulating substrate made of aramid fibers may be fabricated thinner than a glass substrate or the like. The substrate 172 may be in the form of a stacked assembly of an ultrathin glass substrate and aramid fibers.

Bionanofibers are made by compounding a bundle of cellulose microfibrils (bacteria cellulose) produced by bacteria (acetic acid bacteria, *Acetobacter* xylinum) and a transparent resin. The bundle of cellulose microfibrils has a width of 50 nm, which is 1/10 of the wavelength of visible light, is highly strong and highly resilient, and is subject to low thermal expansion. Bionanofibers, which contain 60% to 70% fibers and exhibit a light transmittance of about 90% at a wavelength of 500 nm, can be produced by impregnating bacteria cellulose with a transparent resin such as an acrylic resin, an epoxy rein, or the like, and setting the transparent resin. Bionanofibers are flexible, and have a low coefficient of thermal expansion ranging from 3 ppm to 7 ppm, which is comparable to silicon crystals, a high strength of 460 MPa that matches the strength of steel, and a high resiliency of 30 GPa. Therefore, an insulating substrate 172, which is made of bionanofibers, can be thinner than glass substrates or the like.

Since the photoelectric conversion film 186 of the radiation detector 170 is made of an organic photoelectric conversion material, the photoelectric conversion film 186 absorbs almost none of the radiation 16a through 16c. Therefore, in a PSS type of radiation detector 170, even if the radiation 16a through 16c passes through the TFT substrate 208, since the photoelectric conversion film 186 absorbs only a small amount of radiation 16a through 16c, any reduction in sensitivity to the radiation 16a through 16c is minimized. With a PSS type of radiation detector 170, radiation 16a through 16c passes through the TFT substrate 208 and reaches the scintillator 178. However, since the photoelectric conversion film 186 is made of an organic photoelectric conversion material, the photoelectric conversion film 186 essentially does not absorb radiation 16a through 16c, and any attenuation in radiation 16a through 16c is minimized. Therefore, a photoelectric conversion film 186, which is made of an organic photoelectric conversion material, is suitable for use in a PSS type radiation detector.

The amorphous oxide of the active layer 202 of the thin film transistor 194 and the organic photoelectric conversion material of the photoelectric conversion film 186 can be deposited as films at low temperatures. Therefore, the substrate 172 may be made of plastic, aramid fibers, or bionanofibers, which absorb only small amounts of radiation 16a through 16c. Since the substrate 172 thus made of plastic, aramid fibers, or bionanofibers absorbs only a small amount of radiation 16a through 16c, the substrate 172 is effective to prevent the sensitivity to radiation 16a through 16c from being lowered, even if radiation 16a through 16c passes through the TFT substrate 208 due to being used in a PSS type radiation detector.

According to the seventh modification, the radiation detector may be constituted in the following manner.

(1) The sensor 176 including the photoelectric conversion film 186 made of an organic photoelectric conversion material may be constructed so as to constitute the signal output section 174 using a CMOS sensor. In this case, since only the sensor 176 is made up from an organic photoelectric conversion material, the signal output section 174 including the CMOS sensor does not need to be flexible. Concerning the sensor 176, which is constructed to include an organic photoelectric conversion material, as well as the CMOS sensor, details thereof have been described in Japanese Laid-Open Patent Publication No. 2009-212377, and thus detailed explanations of such features are omitted.

(2) The sensor 176 including the photoelectric conversion film 186 made of an organic photoelectric conversion material may be constructed so as to realize the signal output section 174, which possesses flexibility, by a CMOS circuit equipped with a thin film transistor (TFT) 194 made up from an organic material. In this case, pentacene may be adopted as a material of a p-type organic semiconductor, and fluorinated copper phthalocyanine ($F_{16}CuPc$) may be adopted as an n-type organic semiconductor used by the CMOS circuit. In accordance therewith, a TFT substrate 208 having a certain flexibility with a smaller radius of curvature can be realized. Further, by constructing the TFT substrate 208 in this manner, the gate insulating film 200 can be made quite thin, thus enabling the drive voltage to be lowered. Furthermore, the gate insulating film 200, the semiconductor body, and each of the electrodes can be manufactured at room temperature or at a temperature of 100° C. or less. Still further, the CMOS circuit may be manufactured directly on such a flexible insulating substrate 172. Additionally, the thin film transistor 194 made from an organic material can be miniaturized by a manufacturing process in accordance with scaling rules. For the substrate 172, if a polyimide precursor is coated on a polyimide substrate and heated using a spin coat method, because the polyimide precursor is converted into a polyimide, a flat substrate free of concave-convex irregularities can be realized.

(3) A self-assembly technique (fluidic self-assembly method) in which a plurality of micron-order device blocks are arranged in specified positions on a substrate may be applied, and the sensor 176 and the signal output section 174 may be arranged on an insulating substrate 172 made up from a resin substrate. In this case, the sensor 176 and the signal output section 174, which are micron-order miniature device blocks, are manufactured on another substrate and thereafter are separated from the substrate. Then, the sensor 176 and the signal output section 174 are dispersed in a liquid and arranged statistically on the substrate 172, which serves as a target substrate. A process may be implemented on the substrate 172 in advance for adapting the substrate 172 to the device blocks, and the device blocks can be selectively arranged on the substrate 172. Accordingly, optimum device blocks (i.e., the sensor 176 and the signal output section 174) made up from optimal materials can be integrated on an optimal substrate (insulating substrate 172), and the sensor 176 and the signal output section 174 can be integrated on a non-crystalline insulating substrate 172 (resin substrate).

Figure 28A:
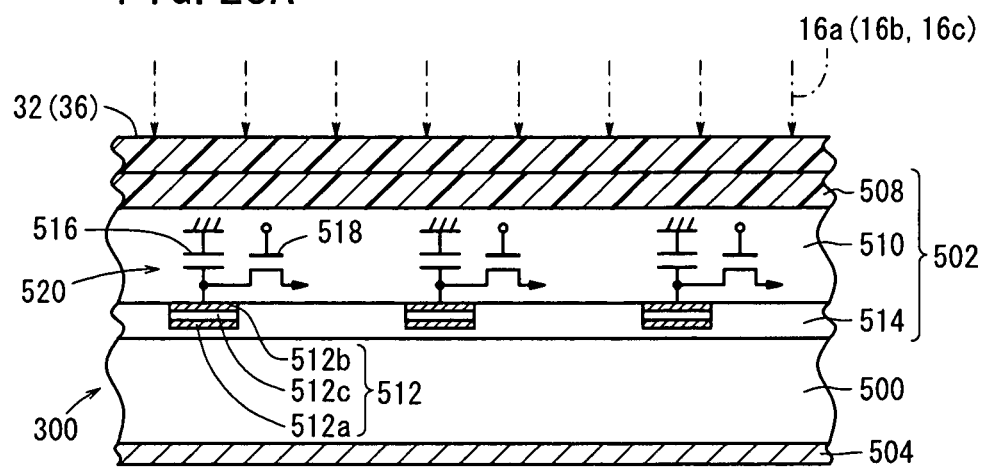
FIG. 28A is an outline explanatory diagram showing schematically an example of a radiographic image capturing system according to an eighth modification.

Next, as an eighth modification of the present invention, an example of an irradiation side sampling (ISS) type of radiation detector 300 including a CsI(Tl) scintillator 500 shall be described with reference to FIGS. 28A and 28B.

The radiation detector 300 comprises an ISS type radiation detector, in which a radiation detecting unit 502, which offers substantially the same functions as the TFT substrate 208 including the signal output section 174 and the sensor 176, and a CsI(Tl) scintillator 500 are arranged in this order with respect to an irradiated surface 32, which is irradiated with radiation 16a through 16c (i.e., along a direction in which radiation 16a through 16c is applied).

In the scintillator 500, the irradiated surface 32 side that is irradiated with radiation 16a through 16c generates and emits light more intensively. In this case, because the radiation detecting unit 502 and the scintillator 500 are arranged in a state of close proximity, compared to a PSS type, an ISS type of radiation detector has a higher ability to resolve the radiographic image, which is obtained through image capturing. Further, the emitted amount of visible light by the radiation detecting unit 502 is increased. Accordingly, more so than a PSS type, an ISS type of radiation detector can enhance the sensitivity of the radiation detector 300 (radiation detecting device 22).

Figure 28B:
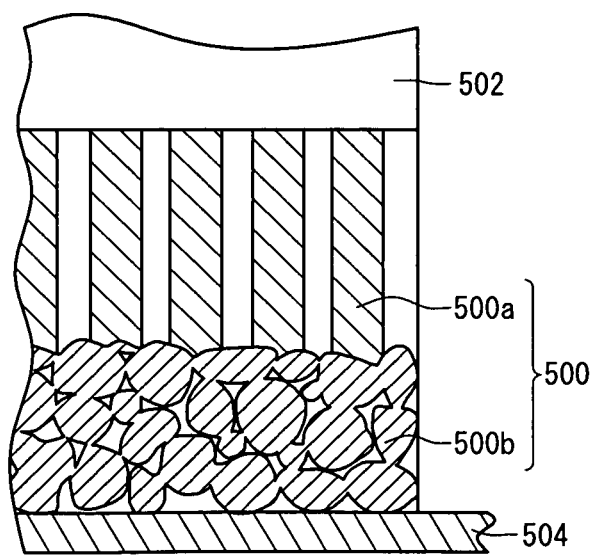
FIG. 28B is an outline explanatory diagram showing an example of a scintillator illustrated in FIG. 28A.

As one example thereof, FIG. 28B shows a case in which a scintillator 500 including a columnar crystalline domain is formed by vapor depositing a material including CsI on a vapor deposition substrate 504.

More specifically, in the scintillator 500 of FIG. 28B, a structure is provided in which a columnar crystalline domain is formed from columnar crystals 500a on the side of the irradiated surface 32 (side of the radiation detecting unit 502), which is irradiated with radiation 16a through 16c, and a non-columnar crystalline domain is formed from non-columnar crystals 500b on a side opposite from the irradiated surface 32. A material of high heat resistance preferably is used as the vapor deposition substrate 504. For example, from the standpoint of lowering costs, aluminum (Al) is preferable. Further, in the scintillator 500, the average diameter of the columnar crystals 500a is substantially uniform over the longitudinal dimension of the columnar crystals 500a.

In the above manner, the scintillator 500 is a structure that is formed by a columnar crystalline domain (columnar crystals 500a) and a non-columnar crystalline domain (non-columnar crystals 500b), and together therewith, the columnar crystalline domain, which is made up from columnar crystals 500a from which light is emitted with high efficiency, are arranged on the side of the radiation detecting unit 502. Owing thereto, visible light emitted by the scintillator 500 progresses within the columnar crystals 500a and is irradiated toward the radiation detecting unit 502. As a result, dispersion of the visible light, which is irradiated toward the side of the radiation detecting unit 502, is suppressed, and blurring of the radiographic image, which is detected by the radiation detecting device 22, also is suppressed. Further, since the visible light that reaches the deep portion (i.e., the non-columnar crystalline domain) of the scintillator 500 also is reflected toward the side of the radiation detecting unit 502 by the non-columnar crystals 500b, the emitted amount of visible light incident on the radiation detecting unit 502 (and the detection efficiency of visible light emitted by the scintillator 500) can be enhanced.

If the thickness of the columnar crystalline domain positioned on the side of the irradiated surface 32 of the scintillator 500 is set at t1, and the thickness of the non-columnar crystalline domain positioned on the side of the vapor deposition substrate 504 of the scintillator 500 is set at t2, then preferably, between t1 and t2, the relationship $0.01 \leq (t2/t1) \leq 0.25$ is satisfied.

In this manner, by satisfying the foregoing relationship between the thickness t1 of the columnar crystalline domain and the thickness t2 of the non-columnar crystalline domain, the ratio along the thickness direction of the scintillator 500 between a domain (columnar crystalline domain) of high light emission efficiency for preventing diffusion of visible light and a domain (non-columnar crystalline domain) for reflecting visible light lies within a suitable range, whereby the light emission efficiency of the scintillator 500, the detection efficiency of visible light emitted by the scintillator 500, and the resolution of the radiographic image are improved.

If the thickness t2 of the non-columnar crystalline domain is excessive, a domain is increased in which the light emission efficiency is low, and the sensitivity of the radiation detecting device 22 also is lowered. Therefore, a range in which the quantity t2/t1 is greater than or equal to 0.02 and less than or equal to 0.1 is particularly preferable.

Further, an explanation has been given above concerning a scintillator 500 having a structure in which the columnar crystalline domain and the non-columnar crystalline domain are formed continuously. However, a structure may be provided in which, in place of the aforementioned non-columnar crystalline domain, a light reflective layer is formed from aluminum (Al) or the like, and only the columnar crystalline domain is formed. Other structures apart therefrom may also be provided.

The radiation detecting unit 502 serves to detect visible light that is radiated out from the light-emitting side (columnar crystals 500a) of the scintillator 500. As viewed from the side in FIG. 28A, an insulating substrate 508, a TFT layer 510, and photoelectric conversion devices 512 are stacked in this order with respect to the irradiated surface 32, along the direction in which radiation 16a through 16c is irradiated. A planarization layer 514 is formed on the bottom surface of the TFT layer 510 so as to cover the photoelectric conversion devices 512.

Further, the radiation detecting unit 502 is constituted as a TFT active matrix substrate (hereinafter referred to as a TFT substrate), in which a plurality of pixels 520, each comprising a photoelectric conversion device 512 made from a photodiode (PD) or the like, a storage capacitor 516, and a thin film transistor (TFT) 518, are formed in a matrix as viewed in plan on the insulating substrate 508.

Furthermore, the photoelectric conversion device 512 is constituted by arranging a photoelectric conversion film 512c between a lower electrode 512a on the side of the scintillator 500, and an upper electrode 512b on the side of the TFT layer 510.

Still further, the TFT 518 of the TFT layer 510 includes a stacked assembly made up of a gate electrode, a gate insulating film, and an active layer (channel layer), and a source electrode and a drain electrode disposed on the active layer are spaced from each other with a gap therebetween.

Further, in the radiation detecting unit 502 that makes up the TFT substrate, a planarization layer 514 for making the radiation detecting unit 502 planar in shape is formed on a side opposite to the arrival direction of the radiation 16a through 16c (on the side of the scintillator 500).

In the following descriptions, in the case that the radiation detector 300 of the eighth modification is contrasted with the radiation detector 170 of the seventh modification, respective constituent elements of the radiation detector 300 correspond respectively with each of the constituent elements of the radiation detector 170.

First, the insulating substrate 508 corresponds with the substrate 172. However, the insulating substrate 508 is not limited as long as it is light transmissive, and is made of a material that absorbs only a small amount of radiation 16a through 16c.

In the case that a glass substrate is used as the insulating substrate 508, the thickness of the radiation detecting unit 502 (TFT substrate) overall is on the order of, for example, 0.7 mm. However, according to the eighth modification, considering making the radiation detecting device 22 thinner in profile, a thin profile substrate made from a light transmissive synthetic resin is used as the insulating substrate 508. As a result, the thickness of the radiation detecting unit 502 overall can be made thinner in profile on the order, for example, of 0.1 mm, whereby the radiation detecting unit 502 can be made to possess flexibility. Further, by making the radiation detection unit 502 flexible, resistance to shocks of the radiation detecting device 22 is improved, and it is more difficult for the radiation detecting device 22 to suffer damage if shocks are applied thereto. Further, plastic resins, aramid, bionanofibers and the like tend not to absorb radiation 16a through 16c, and in the case that the insulating substrate 508 is formed from such materials, since only a small amount of radiation 16a through 16c is absorbed by the insulating substrate 508, even with a structure in which radiation 16a through 16c passes through the insulating substrate 508 as a result of being an ISS type of radiation detector, lowering in sensitivity with respect to radiation 16a through 16c can be suppressed.

With the radiation detecting device 22, it is not essential to utilize a synthetic resin as the insulating substrate 508, and although the thickness of the radiation detecting device 22 will be increased, other materials such as a glass substrate or the like may be used as the insulating substrate 508.

The pixel 520 corresponds to the signal output section 174, and the photoelectric conversion device 512 corresponds to the sensor 176. Owing thereto, the storage capacitor 516 of the pixel 520 corresponds to the capacitor 192 of the signal output section 174, and the TFT 518 corresponds to the thin film transistor 194. Further, the lower electrode 512a of the photoelectric conversion device 512 corresponds to the upper electrode 182 of the sensor 176, the photoelectric conversion film 512c corresponds to the photoelectric conversion film 186, and the upper electrode 512b corresponds to the lower electrode 184.

Stated otherwise, each of the constituent elements of the ISS type radiation detector 300 shown in the eighth modification corresponds in general with each of the constituent elements of the PSS type radiation detector 170 shown in the seventh modification. Accordingly, if the materials used for the constituent elements of the radiation detector 170, which have been described in relation to FIGS. 26 and 27, are applied as materials for the constituent elements corresponding to the radiation detector 300 of the eighth modification, then the same effects according to each of the materials explained with reference to FIGS. 26 and 27 can easily be obtained.

However, different from a PSS type, in an ISS type of radiation detector, because radiation 16a through 16c passes through the radiation detecting unit 502 to arrive at the CsI (Tl) scintillator 500, it is necessary that the radiation detecting unit 502 overall, including the insulating substrate 508, the pixels 520 and the photoelectric conversion devices 512, be constituted from materials that absorb only a slight amount of radiation 16a through 16c.

Accordingly, in the eighth modification, in the case that the photoelectric conversion film 512c is constituted from an organic photoelectric conversion material, since the photoelectric conversion film 512c absorbs almost no radiation 16a through 16c, in an ISS type of radiation detector in which the radiation detecting unit 502 thereof is arranged so as to permit radiation 16a through 16c to pass therethrough, attenuation of radiation 16a through 16c that passes through the radiation detecting unit 502 can be suppressed, and lowering in sensitivity with respect to the radiation 16a through 16c can also be suppressed. Accordingly, constituting the photoelectric conversion film 512c from an organic photoelectric conversion material is favorable, particularly for an ISS type of radiation detector.

Figure 29A:
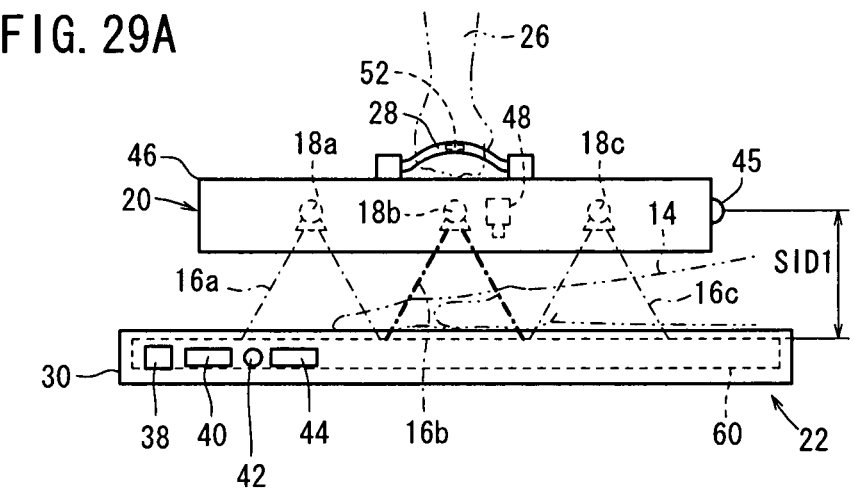
FIG. 29A and FIG. 29B are side views showing cases in which radiation is applied with respect to an image capturing region of a subject, to which a radiographic image capturing system according to a ninth modification is applied.
Figure 29B:
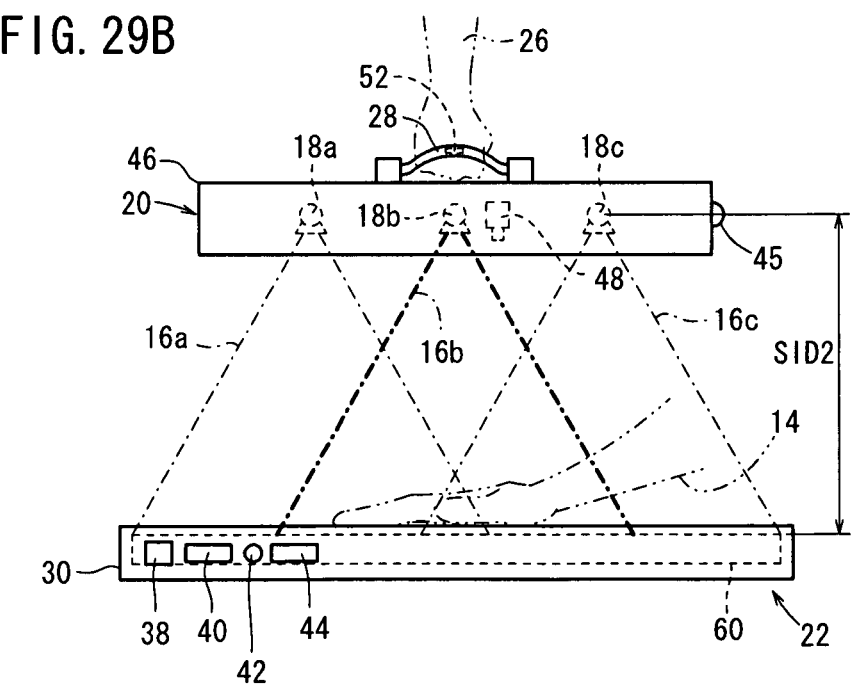

Incidentally, in the present embodiment, in the case that the SID is set by moving the radiation output device 20 while the grip 28 is being gripped by the doctor 26, if the radiation output device 20 is made to approach the subject 14 too closely, then as shown in FIG. 29A, the SID (the distance SID1 shown in FIG. 29A) becomes too short, and cases occur in which image capturing cannot be carried out with respect to the subject 14 except within a comparatively narrow range. Further, if the SID is too short, then the respective irradiation ranges of the radiation 16a through 16c will not be overlapped on the irradiated surface 32, resulting in the possibility that image capturing with respect to the subject 14 will fail.

Consequently, according to the ninth modification, the structure of the sixth modification (see FIGS. 22 and 23) is utilized, whereby based on the acceleration of the radiation output device 20 detected by the acceleration sensor 217, an amount of movement of the radiation output device 20 is calculated, and it is judged whether or not the SID is set at an appropriate distance based on the calculated amount of movement. Then, application of radiation 16a through 16c is permitted, or application of radiation 16a through 16c is started at a point in time that the SID becomes set at the appropriate distance.

More specifically, in the case that the doctor 26 grips the grip 28 and thereby adjusts the SID, the acceleration sensor 217 detects the acceleration of the radiation output device 20 successively, and the control processor 124 calculates the amount of movement of the radiation output device 20 based on the acceleration detected by the acceleration sensor 217. In the exposure permission determining unit 216, in the event that the amount of movement calculated by the control processor 124 reaches a movement amount corresponding to an appropriate SID (e.g., the source-to-image distance SID2 shown in FIG. 29B) for capturing an image of the subject 14, output of radiation (exposure) from each of the radiation sources 18a through 18c is permitted. Consequently, image capturing over a comparatively wide range can be carried out with respect to the subject 14, and image capturing failures with respect to the subject 14 can be avoided.

According to the ninth modification, (1) output of radiation 16a through 16c from the respective radiation sources 18a through 18c may be started by the doctor 26 pressing the exposure switch 130 after exposure has been permitted by the exposure permission determining unit 216, or (2), since the SID2 is set at a point in time when exposure is permitted, output of radiation 16a through 16c from the respective radiation sources 18a through 18c may be started automatically once permission has been granted.

Further, until the source-to-image distance (SID) reaches the SID2, the doctor 26 may be notified and prompted by the display unit 126 or the like to move the radiation output device 20, and may be notified and prompted to stop movement of the radiation output device 20 at a point in time that the SID2 is reached. As a result, in accordance with the notification content to stop movement, at a point in time that the doctor 26 stops moving the radiation output device 20 (i.e., when the acceleration detected by the acceleration sensor 217 is of a zero level), the exposure permission determining unit 216 can grant permission to initiate exposure, and thus capturing of images with respect to the subject 14 can be carried out immediately.

Incidentally, during image capturing with respect to the subject 14, because the center position of the image capturing region of the subject 14 substantially matches the center position of the imaging area 36, and further, since the image capturing region is positioned so as to fit within the imaging area 36, a large number of cases occur in which the region of interest (ROI) is positioned at the center of the imaging area 36. Owing thereto, cases are frequent in which, during actual image capturing, the dose of radiation 16b from the radiation source 18b in the center of the radiation output device 20 is large, whereas the doses of radiation 16a, 16c from both of the radiation sources 18a, 18c are set at smaller doses, of a degree sufficient to compensate the radiation 16b, and image capturing is carried out with respect to the subject 14.

Stated otherwise, during actual image capturing, the control processor 124 performs weighting on each of the radiation doses, such that the dose of radiation 16b from the radiation source 18b in the center of the radiation output device 20 is made maximum, whereas the doses of radiation 16a, 16c from both of the radiation sources 18a, 18c are set at smaller doses, of a degree sufficient to compensate the maximum radiation dose, and in accordance with such weighting, radiation 16a through 16c from each of the radiation sources 18a through 18c is applied simultaneously or sequentially.

In accordance with the aforementioned weighting, upon driving of the respective radiation sources 18a through 18c, only the center radiation source 18b is subject to degradation. Accordingly, from the standpoint of service life management of the radiation output device 20, it is desirable that dosage management is carried out, so that the cumulative doses (cumulative exposure doses) from each of the radiation sources 18a through 18c are respectively the same, and prolonged usage life of the radiation output device 20 including the respective radiation sources 18a through 18c can be realized.

Consequently, according to the tenth modification, for example, in step S8 and step S14 of FIG. 15, data of the doses of radiation 16a through 16c (dose data on which weighting has been carried out) corresponding to optimal radiation dosage data retrieved by the database retriever 150 is stored in the database 134, and the stored data of the respective radiation doses serves to assist radiation dosage management and management of service life.

As a result, concerning the cumulative exposure dose of radiation 16a through 16c, which is output from the respective radiation sources 18a through 18c, in the event that the cumulative exposure dose of the radiation 16b is more prominent than the cumulative exposure dose of the radiation 16a and 16b, there is a possibility that the radiation source 18b may degrade more rapidly than the radiation sources 18a and 18c. Consequently, based on comparing each of the cumulative exposure doses, weighting of the respective radiation doses is changed, such that the doses of radiation 16a, 16c output from each of the radiation sources 18a, 18c at both ends are made maximum with respect to capturing of images having a large SID, whereas the dose of radiation 16b output from the central radiation source 18b is of a smaller dose, of a degree for supplementing the aforementioned maximum dose.

In this manner, as a material for determining the respective cumulative exposure doses, by changing the weighting of the doses of radiation 16a through 16c output from each of the radiation sources 18a through 18c, degradation of only the radiation source 18b can be avoided, and prolonged usage life of the radiation output device 20 including the respective radiation sources 18a through 18c can be realized.

Although a certain preferred embodiment of the present invention has been shown and described in detail, it should be understood that various changes and modifications may be made to the embodiment without departing from the scope of the invention as set forth in the appended claims.

What is claimed is:

1. A radiographic image capturing system comprising:
    a radiation output device housing therein radiation sources for emitting radiation;
    a radiation detecting device for detecting radiation that has passed through a subject and converting the detected radiation into a radiographic image;
    a camera for acquiring an optical image of the subject; and
    a control device for controlling the radiation output device and the radiation detecting device,
    wherein the control device weights doses of the radiation emitted from the radiation sources based on the optical image, and controls the radiation output device to apply the weighted doses of the radiation from the radiation sources to the subject, and
    wherein the radiation output device houses therein three radiation sources, and the control device weights, based on the optical image, the doses of the radiation to be emitted from the three radiation sources, such that the dose of the radiation emitted from a central one of the radiation sources is of a maximum dose level, and the doses of the radiation emitted from the radiation sources at opposite ends are of a lower dose level, or the doses of the radiation emitted from the radiation sources at opposite ends are of a maximum dose level, and the dose of the radiation emitted from a central one of the radiation sources is of a lower dose level.

2. The radiographic image capturing system according to claim 1, wherein the control device comprises:
    a database storing weighting data for weighting of the doses of the radiation emitted from the three radiation sources;
    a database retriever for identifying a region to be imaged of the subject, which is indicated by the optical image, and for retrieving the weighting data corresponding to the identified region to be imaged of the subject from the database;
    an image capturing condition setting unit for setting image capturing conditions for irradiating the subject with the radiation based on the region to be imaged of the subject and the weighting data retrieved by the database retriever; and
    a control processor for controlling the radiation output device and the radiation detecting device according to the image capturing conditions.

3. The radiographic image capturing system according to claim 2, wherein the database further stores optimum radiation dose data representative of optimum radiation doses depending on a plurality of regions to be imaged of the subject and respective thicknesses of the regions;
    after having identified the region to be imaged of the subject, which is indicated by the optical image, the database retriever retrieves, from the database, the optimum radiation dose data of a region to be imaged of the subject and a thickness thereof, which agree with the identified region to be imaged of the subject and the thickness thereof, and the weighting data of the region to be imaged of the subject, which agrees with the identified region to be imaged of the subject; and
    the image capturing condition setting unit sets image capturing conditions based on the region to be imaged of the subject and the thickness thereof, and the optimum radiation dose data and the weighting data, which are retrieved by the database retriever.

4. The radiographic image capturing system according to claim 3, wherein the optimum radiation dose data are stored in the database in association with the regions to be imaged of the subject, the thicknesses thereof, and image capturing techniques representing orientations of the regions to be imaged of the subject with respect to the radiation detecting device, and directions in which the radiation is applied to the regions to be imaged of the subject;
    the weighting data are stored in the database in association with the regions to be imaged of the subject and the respective image capturing techniques depending on the regions to be imaged of the subject;
    the database retriever retrieves, from the database, optimum radiation dose data of a region to be imaged of the subject, a thickness thereof, and an image capturing technique therefor, which correspond to the identified region to be imaged of the subject, the thickness thereof, and the image capturing technique therefor, and weighting data of a region to be imaged of the subject and an image capturing technique therefor, which correspond to the identified region to be imaged of the subject and the image capturing technique therefor; and
    the image capturing condition setting unit sets image capturing conditions based on the region to be imaged of the subject, the thickness thereof, and the image capturing technique therefor, and the optimum radiation dose data and the weighting data, which are retrieved by the database retriever.

5. The radiographic image capturing system according to claim 4, wherein the database further stores object data representing respective optical images of the regions to be imaged of the subject; and
    the database retriever retrieves, from the database, object data corresponding to the optical image acquired by the camera, and identifies a region to be imaged, which is represented by the retrieved object data as the region to be imaged of the subject.

6. The radiographic image capturing system according to claim 5, wherein the control processor controls the camera to start capturing the optical image after having acquired, from an external source, order information for requesting a radiographic image of the subject to be captured.

7. The radiographic image capturing system according to claim 5, wherein the image capturing condition setting unit is capable of changing the optimum radiation dose data and the weighting data, which are retrieved by the database retriever, depending on order information for requesting a radiographic image of the subject to be captured, the subject, or the image capturing technique for the subject.

8. The radiographic image capturing system according to claim 2, wherein the database retriever retrieves the weighting data corresponding to the region to be imaged of the subject from the database, if the optical image acquired by the camera is an optical image that includes the region to be imaged of the subject in an imaging range of the camera.

9. The radiographic image capturing system according to claim 1, wherein if a region to be imaged of the subject represents a hand, then the control device weights the doses of the radiation to be emitted from the three radiation sources, such that the dose of the radiation emitted from the central one of the radiation sources is of the maximum dose level, and the doses of the radiation emitted from the radiation sources at the opposite ends are of the lower dose level, and if the region to be imaged of the subject represents a chest, then the control device weights the doses of the radiation to be emitted from the three radiation sources, such that the doses of the radiation emitted from the radiation sources at the opposite ends are of the maximum dose level and the dose of the radiation emitted from the central one of the radiation sources is of the lower dose level.

10. The radiographic image capturing system according to claim 1, wherein the radiation output device simultaneously or sequentially applies the radiation from the three radiation sources to the subject.

11. The radiographic image capturing system according to claim 1, wherein the radiation output device and the radiation detecting device face each other, and the radiation output device houses therein the three radiation sources arranged in a linear array, or at least three radiation sources arranged in a two-dimensional matrix over an irradiated surface of the radiation detecting device, which is irradiated with the radiation.

12. The radiographic image capturing system according to claim 1, wherein the radiation output device and the radiation detecting device comprise portable devices; and
the control device comprises a portable terminal or a console installed in a medical organization.

13. The radiographic image capturing system according to claim 1, wherein the radiation output device includes a grip on a side thereof remote from a side on which the radiation is emitted;
the grip incorporates therein a gripped state sensor for outputting a detection signal indicating that the grip is gripped; and
the radiation output device permits the three radiation sources to emit the radiation when the gripped state sensor outputs the detection signal.

14. The radiographic image capturing system according to claim 1, wherein the camera is integrally combined with the radiation output device, or the camera is integrally combined with the control device, or the camera is separate from the radiation output device and the control device.

15. The radiographic image capturing system according to claim 1, wherein the radiation sources are battery-powered field-emission radiation sources.

16. A radiographic image capturing method comprising:
capturing an optical image of a subject with a camera while the subject is disposed between a radiation output device housing therein radiation sources and a radiation detecting device;
weighting doses of radiation to be emitted from the radiation sources based on the optical image, and applying the weighted doses of the radiation from the radiation sources to the subject; and
acquiring a radiographic image of the subject by detecting the radiation that has passed through the subject with the radiation detecting device,
wherein the radiation output device houses therein three radiation sources, and a control device weights, based on the optical image, the doses of the radiation to be emitted from the three radiation sources, such that the dose of the radiation emitted from a central one of the radiation sources is of a maximum dose level, and the doses of the radiation emitted from the radiation sources at opposite ends are of a lower dose level, or the doses of the radiation emitted from the radiation sources at opposite ends are of a maximum dose level, and the dose of the radiation emitted from a central one of the radiation sources is of a lower dose level.

* * * * *